(12) United States Patent
Jacobson et al.

(10) Patent No.: US 6,258,751 B1
(45) Date of Patent: Jul. 10, 2001

(54) SUBSTITUTED TRIAZOLES IMIDAZOLES AND PYRAZOLES AS HERBICIDES

(75) Inventors: Richard Martin Jacobson, Chalfont; Mark Joseph Mulvihill, Ambler, both of PA (US); Changling Liu; Xiaonan Liu, both of Liaoning (HK)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/593,096

(22) Filed: Jun. 13, 2000

Related U.S. Application Data
(60) Provisional application No. 60/139,152, filed on Jun. 14, 1999.

(51) Int. Cl.$^7$ .................. A01N 43/653; C07D 213/02; C07D 237/06; C07D 249/08; C07D 249/10
(52) U.S. Cl. ............. 504/227; 504/229; 504/235; 504/237; 504/238; 504/243; 544/182; 544/220; 544/239; 544/241; 544/310; 548/131; 548/132; 548/133; 548/138; 548/143; 548/144; 548/262.4; 548/263.4; 548/263.8
(58) Field of Search .................. 548/262.2, 131, 548/132, 133, 138, 143, 144, 262.4, 263.4, 263.8; 504/272, 273, 227, 229, 235, 237, 238, 243; 544/182, 220, 239, 241, 310

(56) References Cited

U.S. PATENT DOCUMENTS
4,917,721 * 4/1990 Pissiotas et al. .................. 548/476

FOREIGN PATENT DOCUMENTS
0 083 055 A2   12/1982   (EP).
0 273 417 A1   12/1987   (EP).

* cited by examiner

*Primary Examiner*—Richard L. Raymond
*Assistant Examiner*—Venkataraman Balasubramanian
(74) *Attorney, Agent, or Firm*—Clark R. Carpenter

(57) ABSTRACT

The present invention relates to novel heterocyclic compounds and their agronomically suitable salts, methods for the use of these compounds in controlling unwanted plant species, and the use of herbicidal compositions containing these compounds. In particular, the present invention pertains to substituted and unsubstituted triazoles, imidazoles and pyrazoles linked to a heterocyclic substituted benzene group. Such compounds are useful as pre-emergent and post-emergent herbicides.

8 Claims, No Drawings

SUBSTITUTED TRIAZOLES IMIDAZOLES AND PYRAZOLES AS HERBICIDES

This application claims benefit of provisional application 60/139,152 filed Jun. 14, 1999.

The present invention relates to novel heterocyclic compounds and their agronomically suitable salts, methods for the use of these compounds in controlling unwanted plant species, and the use of herbicidal compositions containing these compounds.

The presence of unwanted plant species causes substantial damage to useful crops, especially agricultural products that satisfy the human being's basic food and fiber needs, such as cotton, rice, corn, wheat, soybean. The current population explosion and concomitant world food and fiber shortage demand improvements in efficiency of producing these crops. Prevention or minimizing loss of a portion of such valuable crops by killing, or inhibiting the growth of unwanted plant species is one way of improving this efficiency. Though many herbicides are available, the need still exists for more effective herbicides.

The compounds of the present invention in general show a usefully improved level of crop safety on soybean, corn or wheat than the known compounds.

EP 0 083 055 A2, published Jul. 6, 1983, discloses herbicidal compounds of the following formula (i)

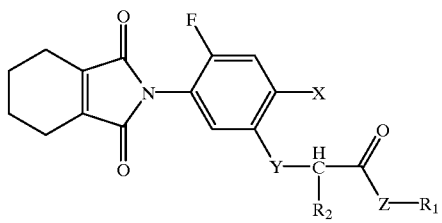

(i)

wherein $R_1$ is hydrogen, alkyl, lower cycloalkyl, lower alkyl (lower)cycloalkyl, lowercycloalkyl(lower)alkyl, lower alkoxyl(lower)alkyl, lower alkenyl, lower cycloalkenyl, lower cycloalkenyl(lower)alkyl, phenyl, cyano(lower)alkyl, lower alkynyl, lower alkylideneamino, lower alkylthio (lower)alkyl, benzyl, halo(lower)alkyl or lower cycloalkylideneamino;

$R_2$ is hydrogen, lower alkyl, lower alkoxyl;

X is chlorine or bromine;

Y is oxygen or imino; and

Z is oxygen or sulfur.

EP 0 273 417 A1 published Jul. 6, 1988 discloses the herbicidal compounds having the formula (ii)

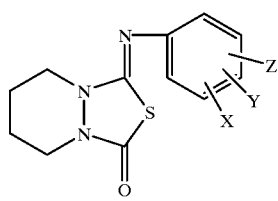

(ii)

wherein each of X and Y is hydrogen or halogen;

Z is —SCH(R)COOR$^1$;

R is hydrogen, alkyl, and R$^1$ is alkyl, cycloalkyl, or alkoxyalkyl, or COOQ wherein Q is alkyl, or Y and Z together form

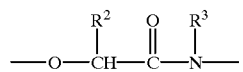

bonded to phenyl ring, wherein R$^2$ is H or alkyl, and R$^3$ is alkyl, alkenyl, or alkynyl.

The present invention relates to novel herbicidal compounds and methods for their use in controlling unwanted plant species and their use in herbicidal compositions in agriculture. In particular, the present invention pertains to substituted and unsubstituted triazoles, imidazoles and pyrazoles linked to a heterocyclic substituted benzene group.

It has now been found that certain triazoles, imidazoles and pyrazoles linked to a heterocyclic substituted benzene group are useful as pre-emergent and post-emergent herbicides. These novel compounds are represented by formula I

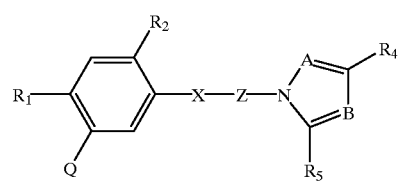

I wherein $R_1$ is selected from H, F, Br, Cl, NO$_2$ and CN;

$R_2$ is selected from F, Cl, Br, H and CN;

$R_3$ is selected from H and CN; and alkyl, alkenyl, alkynyl, haloalkyl, cycloalkyl, cycloalkenyl, haloalkenyl, haloalkynyl, alkoxy, alkylthio, alkylsulfonylalkyl, alkylsulfinylalkyl, alkylsulfonylcycloalkyl, alkylsulfinylcycloalkyl, aryl, arylalkyl, heteroaryl and heteroarylalkyl, all of which may be further substituted;

$R_4$ and $R_5$ are each independently selected from H, halo and CN; and alkyl, cycloalkyl, haloalkyl, alkoxy, alkylthio, alkylsulfonylalkyl, alkylsulfinylalkyl, alkylsulfonylcycloalkyl, alkylsulfinylcycloalkyl, CO$_2$R$_6$, CONR$_6$R$_{13}$, OR$_6$, SR$_6$, SO$_2$R$_6$, NR$_6$R$_{13}$, SO$_2$NR$_6$R$_{13}$, aryl, arylalkyl, heteroaryl and heteroarylalkyl, all of which may be further substituted;

$R_6$ is selected from H, alkyl, cycloalkyl, alkoxy, alkylthio, alkylsulfonylalkyl, alkylsulfinylalkyl, alkylsulfonylcycloalkyl, alkylsulfinylcycloalkyl, aryl and arylalkyl, all of which may be further substituted;

$R_7$ is selected from H, alkyl, alkenyl, alkynyl, haloalkyl, cycloalkyl, alkylsulfonylalkyl, alkylsulfinylalkyl, alkylsulfonylcycloalkyl, alkylsulfinylcycloalkyl and COR$_9$, all of which may be further substituted;

$R_8$ is selected from alkyl, haloalkyl, cycloalkyl, cycloalkenyl, alkylsulfonylalkyl, alkylsulfinylalkyl, alkylsulfonylcycloalkyl, alkylsulfinylcycloalkyl, aryl and arylalkyl, all of which may be further substituted;

$R_9$ is selected from H, alkyl, alkylsulfonylalkyl, alkylsulfinylalkyl, alkylsulfonylcycloalkyl, alkylsulfinylcycloalkyl, alkenyl, alkynyl, haloalkyl and cycloalkyl, all of which may be further substituted;

$R_{10}$ is selected from H, halo, NH$_2$, alkyl, alkylsulfonylalkyl, alkylsulfinylalkyl, alkylsulfonylcycloalkyl, alkylsulfinylcycloalkyl, haloalkyl, CN, CO$_2$(alkyl), CONH(alkyl), CON(alkyl)$_2$ wherein each alkyl may be the same or different, $CH_2CN$, $CH_2CH=CH_2$, $CH_2C\equiv CH$, $CH_2CO_2$(alkyl), $CH_2OCH_3$ and $CH_2$-1,2,4-triazole, all of which may be further substituted;

$R_{11}$ is selected from H, CN, alkyl, haloalkyl and $CO_2$ (alkyl);

$R_{12}$ is selected from H, alkyl, $CO_2R_6$, $CONR_6R_{13}$, $OR_6$, $SR_6$, $SO_2R_6$, $SO_2NR_6R_{13}$ and $NR_6R_{13}$;

$R_{13}$ is H, alkyl, aryl or arylalkyl;

A is N or CH;

B is N or $CR_{10}$;

Z is O, $CH(R_3)$, CO, CS, $CONR_{12}$ or $CSNR_{12}$;

X is selected from O, S, $NR_{12}$, $CO_2$, $OCH(R_6)CO_2$, $SCH(R_6)CO_2$, $CH=C(halo)CO_2$, $CH_2CH(halo)CO_2$, CONH, $OCH(R_6)CONH$, $SCH(R_6)CONH$, $CH=C(halo)CONH$ and $CH_2CH(halo)CONH$ when Z is $CH(R_3)$;

X is selected from CO, $OCH(R_6)CO$, $SCH(R_6)CO$, $CH=C(halo)CO$ and $CH_2CH(halo)CO$ when Z is O;

X is selected from O, S, CO, $OCH(R_6)$, $CH=C(halo)$, $CH_2CH(halo)$, CONH, $OCH(R_6)CONH$, $SCH(R_6)CONH$, $CH=C(halo)CONH$, $CH_2CH(halo)CONH$ and $NR_{12}$ when Z is CO, CS, $CONR_{12}$ or $CSNR_{12}$; and Q is selected from $NR_7COR_8$, Q1, Q2, Q3, Q4, Q5, Q6, Q7, Q8, Q9, Q10, Q11, Q12, Q13, Q14, Q15 and Q16 wherein Q1 is 4,5,6,7-tetrahydrophthalimid-2-yl, Q2 is 5,6,7,8-tetrahydro-1,2,4-triazolo[4, 3-a]pyridin-3 (2H)-one-1-yl, Q3 is 5,6,7,8-tetrahydro-1H,3H-[1,3,4]thiadiazolo[3,5-a] pyridazineimin-1-yl, Q4 is 4,5,6,7-tetrahydroimidazo[1,5-a]pyridine-1,3(2H, 5H)-dione-2-yl, Q5 is 1,6,8-triazabicyclo[4,3,0]-nonane-7,9-dion-8-yl, Q6 is 5-(1-methyethylidene)-2,4-oxazolidinedione-3-yl, Q7 is 5-(1,1-dimethylethyl)-1,3,4-oxadiazol-2(3H)-one-3-yl, Q8 is 4-difluoromethyl-4, 5-dihydro-3-methyl- 1,2,4-triazol-5(1H)-one-1-yl, Q9 is 2-methyl-1,2,4-oxadiazolidine-3,5-dione-4-yl, Q10 is 4-chloro-1-methyl-5-difluoromethoxy-1H-pyrazol-3-yl, Q11 is 4-bromo-1-methyl-5-trifluoromethyl-1H-pyrazol-3-yl, Q12 is 1-substituted-6-trifluoromethyl-2,4-pyrimidione-3-yl, Q13 is 1-substituted-6-trifluoromethyl-1,3,5-triazine-2,4-dione-1-yl, Q14 is 4,5-disubstituted-4,5-dihydro-1,2,4-triazine-3 (2H)-one-2-yl, Q15 is 4-substituted-1,2,4-triazine-3,5(2H,4H)-dione-2-yl and Q16 is 5-methyl-6-oxo-4-(trifluoromethyl)-6H-pyridazin-1-yl;

or the agronomically acceptable salts thereof

As used in the present invention, the term "aryl" is defined as a monocyclic or polycyclic ring selected from benzene, naphthalene, indene, anthracene, indacene, fluorene, acenaphthalene, phenanthrene and azulene.

"Heteroaryl" is defined as a monocyclic or polycyclic ring selected from furan, thiophene, pyrrole, isoxazole, oxazole, isothiazole, thiazole, pyrazole, imidazole, 1,2,3-triazole, 1,2,4-triazole, tetrazole, 1,2,3-thiadiazole, 1,2,4-thiadiazole, 1,3,4-thiadiazole, 1,2,3-thiadiazole, 1,2,4-thiadiazole, 1,3,4-thiadiazole, pyridine, pyridazine, pyrimidine, pyrazine, 1,3,5-triazine, 1,2,4-triazine, 1,2,4,5-tetrazine, benzofuran, benzothiophene, indole, benzisoxazole, benzoxazole, benzisothiazole, benzothiazole, benzopyrazole, benzimidazole, benzotriazole, 1,2-methylenedioxybenzene, 1,2-ethylenedioxybenzene, quinoline and isoquinoline.

The structures of the "Q" heterocyclic groups previously named are

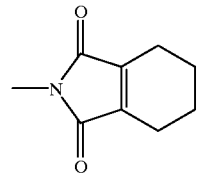

Q1

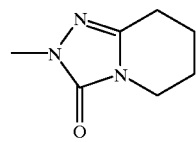

Q2

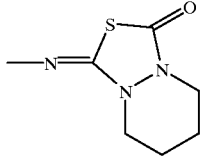

Q3

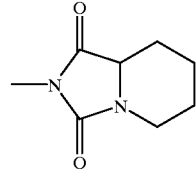

Q4

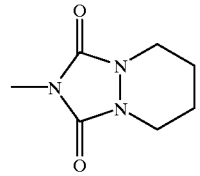

Q5

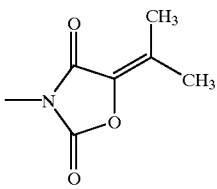

Q6

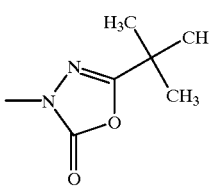

Q7

-continued

Q8 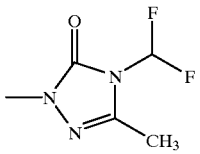

Q9 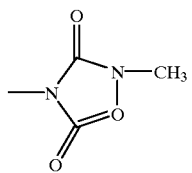

Q10 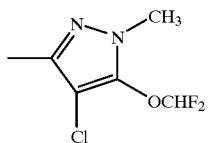

Q11 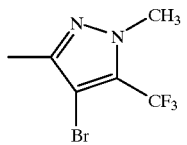

Q12 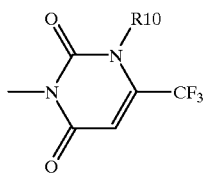

Q13 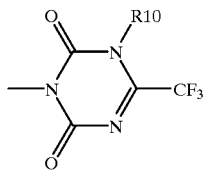

Q14 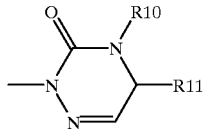

Q15 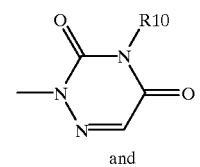

and

Q16 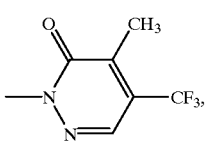

where $R_{10}$ and $R_{11}$ are as previously defined.

The term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl and the like.

The term "cycloalkyl" refers to a cyclic aliphatic ring structure such as cyclopropane, cyclobutane, cyclopentane, cyclohexane, cycloheptane, cyclooctane and the like.

The term "haloalkyl" refers to an alkyl group substituted with one or more halo groups.

The term "halo" refers to fluoro, chloro, bromo or iodo.

The term "alkylsulfonylalkyl" refers to an alkyl group substituted with an alkylsulfonyl (alkyl-$SO_2$) group, for example methylsulfonylmethyl.

The term "alkylsulfinylalkyl" refers to an alkyl group substituted with an alkylsulfinyl (alkyl-SO) group, for example methylsulfinylmethyl.

The term "alkenyl" refers to an ethylenically unsaturated hydrocarbon group, straight or branched, having 1 or 2 ethylenic bonds.

The term "cycloalkenyl" refers to a cyclic aliphatic ring structure having 1 or 2 ethylenic bonds such as cyclopentene, cyclohexene, 1,4-cyclohexadiene and the like.

The term "haloalkenyl" refers to an alkenyl group substituted with one or more halo groups.

The term "alkynyl" refers to an unsaturated hydrocarbon group, straight or branched, having 1 or 2 acetylenic bonds.

The term "arylalkyl" is used to describe a group wherein the alkyl chain can be branched or straight chain with the aryl portion, as defined above, forming a terminal portion of the arylalkyl moiety.

The term "heteroarylalkyl" is used to describe a group wherein the alkyl chain can be branched or straight chain with the heteroaryl portion, as defined above, forming a terminal portion of the heteroarylalkyl moiety.

The term "alkoxy" includes both branched and straight chain alkyl groups attached to a terminal oxygen atom. Typical alkoxy groups include methoxy, ethoxy, n-propoxy, isopropoxy, tert-butoxy and the like.

The term "haloalkoxy" refers to an alkoxy group substituted with one or more halo groups.

The term "alkylthio" includes both branched and straight chain alkyl groups attached to a terminal sulfur atom.

The term "haloalkylthio" refers to an alkylthio group substituted with one or more halo groups.

Acceptable acids that may form salts of the compounds of the present invention can be selected from hydrochloric acid, hydrobromic acid, hydroiodic acid, sulfuric acid, nitric acid, phosphoric acid, oxalic acid, acetic acid, propionic acid, glycolic acid, methanesulfonic acid, toluenesulfonic acid, benzenesulfonic acid, ($C_2$–$C_{20}$)alkylbenzenesulfonic acid, sodium hydrogen sulfate and methyl hydrogen sulfate.

Other agronomically acceptable salts may be formed by complexation of the compounds of the current invention with metal salts such as zinc chloride or iron chloride.

A preferred embodiment of this invention are the compounds of formula I wherein $R_1$ is selected from H, F, Br, Cl, $NO_2$ and CN;

$R_2$ is selected from F, Cl, Br, H and CN;

$R_3$ is selected from H, CN and halo; and ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$)alkylsulfonyl($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl, aryl, heteroaryl, aryl($C_1$–$C_{12}$)alkyl and heteroaryl($C_2$–$C_{12}$)alkyl, all of which may be further substituted with from one to three substituents independently selected from bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$)alkylsulfonyl, ($C_1$–$C_{12}$)alkylsulfinyl, phenyl, phen($C_1$–$C_{12}$)alkyl, phen($C_2$–$C_{12}$)alkenyl, phen($C_2$–$C_{12}$)alkynyl, cyano, halo($C_1$–$C_{12}$)alkoxy, 1,3-dioxalan-2-yl and nitro;

$R_4$ and $R_5$ are each independently selected from H, halo and CN; and ($C_1$–$C_{12}$)alkyl, cyclo($C_3$–$C_8$)alkyl, halo($C_1$–$C_{12}$)alkyl, ($C_1$–$C_{12}$)alkoxy, ($C_1$–$C_{12}$)alkylthio, ($C_1$–$C_{12}$)alkylsulfonyl ($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl, $CO_2R_6$, $CONHR_6$, $CON((C_1$–$C_{12})alkyl)R_6$, $OR_6$, $SR_6$, $SO_2R_6$, $NHR_6$, $N((C_1$–$C_{12})alkyl)R_6$, $SO_2N((C_1$–$C_{12})alkyl)R_6$, aryl, heteroaryl, aryl($C_1$–$C_{12}$)alkyl and heteroaryl($C_2$–$C_{12}$)alkyl, all of which may be further substituted with from one to three substituents independently selected from bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$)alkylsulfonyl, ($C_1$–$C_{12}$)alkylsulfinyl, phenyl, phen($C_1$–$C_{12}$)alkyl, phen($C_2$–$C_{12}$)alkenyl, phen($C_2$–$C_{12}$)alkynyl, cyano, halo($C_1$–$C_{12}$)alkoxy, 1,3-dioxalan-2-yl and nitro;

$R_6$ is selected from H, ($C_1$–$C_{12}$)alkyl, ($C_1$–$C_{12}$)alkylsulfonyl($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl, aryl and aryl($C_1$–$C_{12}$)alkyl;

$R_7$ is selected from H, ($C_1$–$C_{12}$)alkyl, cyclo($C_3$–$C_8$)alkyl, halo($C_1$–$C_{12}$)alkyl, ($C_1$–$C_{12}$)alkylsulfonyl($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl and $COR_9$;

$R_8$ is selected from ($C_1$–$C_{12}$)alkyl, cyclo($C_3$–$C_8$)alkyl, cyclo($C_3$–$C_8$)alkenyl, halo($C_1$–$C_{12}$)alkyl, ($C_1$–$C_{12}$)alkylsulfonyl ($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl, aryl and aryl($C_1$–$C_{12}$)alkyl;

$R_9$ is selected from H, ($C_1$–$C_{12}$)alkyl, ($C_2$–$C_{12}$)alkenyl, cyclo($C_3$–$C_8$)alkyl, halo($C_1$–$C_{12}$)alkyl, ($C_1$–$C_{12}$)alkylsulfonyl($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio and halocyclo($C_3$–$C_8$)alkyl;

$R_{10}$ is selected from H, chloro, $NH_2$, ($C_1$–$C_{12}$)alkyl, halo($C_1$–$C_{12}$)alkyl, CN, ($C_1$–$C_{12}$)alkylsulfonyl ($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3C_8$)alkyl, ($C_1$–$C_{12}$)alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo($C_1$–$C_{12}$)alkoxy, halo($C_1$–$C_{12}$)alkylthio, halocyclo($C_3$–$C_8$)alkyl, $CO_2(C_1$–$C_{12})$alkyl, $CONH(C_1$–$C_{12})$alkyl, $CON((C_1$–$C_{12})$alkyl$)_2$, $CH_2CN$, $CH_2CH=CH_2$, $CH_2C\equiv CH$, $CH_2CO_2(C_1$–$C_{12})$alkyl, $CH_2OCH_3$, $CH_2$-1,2,4-triazole;

$R_{11}$ is selected from H, CN, ($C_1$–$C_{12}$)alkyl, halo($C_1$-$C_{,2}$)alkyl and $CO_2(C_1$–$C_{12})$alkyl;

$R_{12}$ is selected from H, ($C_1$–$C_{12}$)alkyl, $CO_2R_6$, $CON((C_1$–$C_{12})alkyl)R_6$, $OR_6$, $SR_6$, $SO_2R_6$, $SO_2N((C_1$–$C_{12})alkyl)R_{13}$ and $N((C_1$–$C_{12})alkyl)R_{13}$;

$R_{13}$ is H, ($C_1$–$C_{12}$)alkyl, aryl or aryl($C_1$–$C_{12}$)alkyl;

A is N or CH;

B is N or $CR_{10}$;

Z is O, $CH(R_3)$, CO, CS, $CONR_{12}$ or $CSNR_{12}$;

X is selected from O, S, $NR_{12}$, $CO_2$, $OCH(R_6)CO_2$, $SCH(R_6)CO_2$, $CH=C(Cl)CO_2$, $CH_2CH(Cl)CO_2$, CONH, $OCH(R_6)CONH$, $SCH(R_6)CONH$, $CH=C(Cl)CONH$ and $CH_2CH(Cl)CONH$ when Z is $CH(R_3)$;

X is selected from CO, $OCH(R_6)CO$, $SCH(R_6)CO$, $CH=C(Cl)CO$, $CH_2CH(Cl)CO$ when Z is O;

X is selected from O, S, CO, $OCH(R_6)$, $CH=C(Cl)$, $CH_2CH(Cl)$, CONH, $OCH(R_6)CONH$, $SCH(R_6)$ CONH, $CH=C(Cl)CONH$, $CH_2CH(Cl)CONH$ and $NR_{12}$ when Z is CO, CS, $CONR_{12}$ or $CSNR_{12}$;

Q is selected from $NR_7COR_8$, Q1, Q2, Q3, Q4, Q5, Q6, Q7, Q8, Q9, Q10, Q11, Q12, Q13, Q14, Q15 and Q16;

or the agronomically acceptable salts thereof.

A more preferred embodiment of this invention are the compounds of formula I wherein $R_1$ is H, F or Cl;

$R_2$ is Cl;

$R_3$ is selected from H, bromo, chloro, fluoro, ($C_1$–$C_6$)alkyl, cyclo($C_5$–$C_6$)alkyl, ($C_2$–$C_6$)alkenyl, cyclo($C_3$–$C_8$)alkenyl, ($C_2$–$C_6$)alkynyl, halo($C_1$–$C_6$)alkyl, halo($C_2$–$C_6$)alkenyl, halo($C_2$–$C_6$)alkynyl, ($C_1$–$C_6$)alkoxy, ($C_1$–$C_6$)alkylthio, aryl, heteroaryl, aryl($C_1$–$C_{12}$)alkyl and heteroaryl($C_2$–$C_{12}$)alkyl wherein the aryl or heteroaryl group is selected from furan, naphthalene, phenyl, pyrazole, pyridine, pyrimidine, thiophene and triazole, said aryl and heteroaryl group may be further substituted with from one to three substituents independently selected from bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$)alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$)alkylsulfonyl, ($C_1$–$C_{12}$)alkylsulfinyl, phenyl, phen($C_1$–$C_{12}$)alkyl, phen($C_2$–$C_{12}$)alkenyl, phen($C_2$–$C_{12}$)alkynyl, cyano, halo($C_1$–$C_{12}$)alkoxy, 1,3-dioxalan-2-yl and nitro;

$R_4$ and $R_5$ are each independently selected from H, bromo, chloro, fluoro, CN, ($C_1$–$C_6$)alkyl, cyclo($C_5$–$C_6$)alkyl, halo($C_1$–$C_6$)alkyl, ($C_1$–$C_6$)alkoxy, ($C_1$–$C_6$)alkylthio, $CO_2R_6$, $CONHR_6$, $CON((C_1$–$C_{12})alkyl)R_6$, $OR_6$, $SR_6$, $SO_2R_6$, $NHR_6$, $N((C_1-C_{12})alkyl)R_6$, $SO_2N((C_1-C_{12})alkyl)R_6$, aryl, heteroaryl, aryl($C_1-C_{12}$)alkyl and heteroaryl($C_2-C_{12}$)alkyl, wherein the aryl or heteroaryl group is selected from furan, naphthalene, phenyl, pyrazole, pyridine, pyrimidine, thiophene and triazole, said aryl and heteroaryl group may be further substituted with from one to three substituents independently selected from bromo, chloro, fluoro, ($C_1-C_{12}$)alkyl, cyclo($C_3-C_8$)alkyl, ($C_2-C_{12}$)alkenyl, cyclo($C_3-C_8$)alkenyl, ($C_2-C_{12}$)alkynyl, halo($C_1-C_{12}$)alkyl, halo($C_2-C_{12}$)alkenyl, halo($C_2-C_{12}$)alkynyl, ($C_1-C_{12}$)alkoxy, ($C_1-C_{12}$)alkylthio, ($C_1-C_{12}$)alkylsulfonyl, ($C_1-C_{12}$)alkylsulfinyl, phenyl, phen($C_1-C_{12}$)alkyl, phen($C_2-C_{12}$)alkenyl, phen($C_2-C_{12}$)alkynyl, cyano, halo($C_1-C_{12}$)alkoxy, 1,3-dioxalan-2-yl and nitro;

$R_6$ is selected from H, ($C_1-C_{12}$)alkyl, aryl and aryl($C_1-C_6$)alkyl, where the aryl group is naphthyl or phenyl;

$R_7$ is selected from H, ($C_1-C_{12}$)alkyl, cyclo($C_3-C_8$)alkyl, halo($C_1-C_{12}$)alkyl and $COR_9$;

$R_8$ is selected from ($C_1-C_{12}$)alkyl, cyclo($C_3-C_8$)alkyl, cyclo($C_3-C_8$)alkenyl, halo($C_1-C_{12}$)alkyl, aryl and aryl($C_1-C_6$)alkyl;

$R_9$ is selected from H, ($C_1-C_6$)alkyl, ($C_2-C_{12}$)alkenyl, ($C_2-C_6$)alkenyl, cyclo($C_3-C_8$)alkyl, cyclo($C_5-C_6$)alkyl, halo($C_1-C_{12}$)alkyl, halo($C_1-C_6$)alkyl;

$R_4$ is selected from H, chloro, $NH_2$, ($C_1-C_6$)alkyl, halo($C_1-C_{12}$)alkyl, halo($C_1-C_6$)alkyl, CN, $CO_2(C_1-C_{12})$alkyl, $CONH(C_1-C_{12})$alkyl, $CON((C_1-C_{12})alkyl)_2$, $CH_2CN$, $CH_2CH=CH_2$, $CH_2C\equiv CH$, $CH_2CO_2(C_1-C_{12})$alkyl, $CH_2OCH_3$, $CH_2$-1,2,4-triazole;

$R_{11}$ is selected from H, CN, ($C_1-C_6$)alkyl, halo($C_1-C_{12}$)alkyl, halo($C_1-C_6$)alkyl and $CO_2(C_1-C_{12})$alkyl;

$R_{12}$ is selected from H, ($C_1-C_8$)alkyl, $CO_2R_6$, $CON((C_1-C_8)alkyl)R_6$, $OR_6$, $SR_6$, $SO_2R_6$, $SO_2N((C_1-C_8)alkyl)R_{13}$ and $N((C_1-C_8)alkyl)R_{13}$;

$R_{13}$ is H, ($C_1-C_8$)alkyl, aryl or aryl($C_1-C_6$)alkyl where the aryl group is naphthyl or phenyl;

A is N or CH;

B is N or $CR_{10}$;

Z is O, $CH(R_3)$, CO, CS, $CONR_{12}$ or $CSNR_{12}$;

X is selected from O, S, NH, $CO_2$, $OCH(R_6)CO_2$, $SCH(R_6)CO_2$, $CH=C(Cl)CO_2$, $CH_2CH(Cl)CO_2$, CONH, $OCH(R_6)CONH$, $SCH(R_6)CONH$, $CH=C(Cl)CONH$ and $CH_2CH(Cl)CONH$ when Z is $CH(R_3)$;

X is selected from CO, $OCH(R_6)CO$, $SCH(R_6)CO$, $CH=C(Cl)CO$ and $CH_2CH(Cl)CO$ when Z is O;

X is selected from O, S, CO, $OCH(R_6)$, $CH=C(Cl)$, $CH_2CH(Cl)$, CONH, $OCH(R_6)CONH$, $SCH(R_6)CONH$, $CH=C(Cl)CONH$, $CH_2CH(Cl)CONH$ and $NR_{12}$ when Z is CO, CS, $CONR_{12}$ or $CSNR_{12}$;

Q is $NR_7COR_8$, or selected from Q1, Q2, Q3, Q4, Q5, Q6, Q7, Q8, Q9, Q10, Q11, Q12, Q13, Q14, Q15 and Q16;

or the agronomically acceptable salts thereof selected from those formed from hydrochloric acid, sulfuric acid, acetic acid, propionic acid, phosphoric acid and oxalic acid.

An even more preferred embodiment of this invention are the compounds of formula I wherein $R_1$ is H, F or Cl;

$R_2$ is Cl;

$R_3$ is selected from H, bromo, chloro, fluoro, ($C_1-C_6$)alkyl, cyclo($C_5-C_6$)alkyl, ($C_2-C_6$)alkenyl, cyclo($C_3-C_8$)alkenyl, ($C_2-C_6$)alkynyl, halo($C_1-C_6$)alkyl, halo($C_2-C_6$)alkenyl, halo($C_2-C_6$)alkynyl, ($C_1-C_6$)alkoxy, ($C_1-C_6$)alkylthio, 3-furyl, 4-chloro-2-furyl, 5-chloro-2-furyl, 5-chloro-3-furyl, 2,5-dichloro-3-furyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-thienyl, 3-thienyl, 4-chloro-2-thienyl, 5-chloro-2-thienyl, 5-chloro-3-thienyl and 2,5-dichloro-3-thienyl;

$R_4$ and $R_5$ are each independently selected from H, bromo, chloro, fluoro, CN, ($C_1-C_6$)alkyl, cyclo($C_5-C_6$)alkyl, halo($C_1-C_6$)alkyl, ($C_1-C_6$)alkoxy, ($C_1-C_6$)alkylthio, $CO_2R_6$, $CONHR_6$, $CON((C_1-C_6)alkyl)R_6$, $OR_6$, $SR_6$, $SO_2R_6$, $NHR_6$, 3-furyl, 4-chloro-2-furyl, 5-chloro-2-furyl, 5-chloro-3-furyl, 2,5-dichloro-3-furyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl 2,6-dichloro-4-pyridyl, 2-thienyl, 3-thienyl, 4-chloro-2-thienyl, 5-chloro-2-thienyl, 5-chloro-3-thienyl and 2,5-dichloro-3-thienyl;

$R_6$ is selected from H, ($C_1-C_6$)alkyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl and 3,4,5-trifluorophenyl;

$R_7$ is selected from H, ($C_1-C_6$)alkyl, cyclo($C_5-C_6$)alkyl, halo($C_1-C_6$)alkyl and $COR_9$;

$R_8$ is ($C_1-C_6$)alkyl, cyclo($C_5-C_6$)alkyl, halo($C_1-C_{12}$)alkyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl and 3,4,5-trifluorophenyl;

$R_9$ is selected from H, $(C_1-C_6)$alkyl, $(C_2-C_6)$alkenyl, cyclo$(C_5-C_6)$alkyl and halo$(C_1-C_6)$alkyl;

$R_{10}$ is selected from H, chloro, $NH_2$, $(C_1-C_6)$alkyl, halo$(C_1-C_6)$alkyl, CN, $CO_2(C_1-C_6)$alkyl, $CONH(C_1-C_6)$alkyl, $CON((C_1-C_6)$alkyl$)_2$, $CH_2CN$, $CH_2CH=CH_2$, $CH_2C\equiv CH$, $CH_2CO_2(C_1-C_6)$alkyl, $CH_2OCH_3$ and $CH_2$-1,2,4-triazole;

$R_{11}$ is H, CN, $(C_1-C_6)$alkyl, halo$(C_1-C_6)$alkyl and $CO_2(C_1-C_6)$alkyl;

$R_{12}$ is selected from H, $(C_1-C_6)$alkyl, $CO_2(C_1-C_6)$alkyl, $CON((C_1-C_6)$alkyl$)_2$, $O(C_1-C_6)$alkyl, $S(C_1-C_6)$alkyl, $SO_2(C_1-C_6)$alkyl, $SO_2N((C_1-C_6)$alkyl$)_2$ and $N((C_1-C_6)$alkyl$)_2$;

$R_{13}$ is H, $(C_1-C_6)$alkyl, aryl or aryl$(C_1-C_4)$alkyl where the aryl group is naphthyl or phenyl;

A is N or CH;

B is N or $CR_{10}$;

Z is O, $CH(R_3)$, CO, CS, $CONR_{12}$ or $CSNR_{12}$;

X is selected from O, S, NH, $CO_2$, $OCH(R_6)CO_2$, $SCH(R_6)CO_2$, $CH=C(Cl)CO_2$, $CH_2CH(Cl)CO_2$, CONH, $OCH(R_6)CONH$, $SCH(R_6)CONH$, $CH=C(Cl)CONH$ and $CH_2CH(Cl)CONH$ when Z is $CH(R_3)$;

X is selected from CO, $OCH(R_6)CO$, $SCH(R_6)CO$, $CH=C(Cl)CO$ and $CH_2CH(Cl)CO$ when Z is O;

X is selected from O, S, CO, $OCH(R_6)$, $CH=C(Cl)$, $CH_2CH(Cl)$, CONH, $OCH(R_6)CONH$, $SCH(R_6)CONH$, $CH=C(Cl)CONH$, $CH_2CH(Cl)CONH$ and $NR_{12}$ when Z is CO, CS, $CONR_{12}$ or $CSNR_{12}$;

Q is selected from Q1, Q2, Q3, Q4, Q5, Q6, Q7, Q8, Q9, Q10, Q11, Q12, Q13, Q14, Q15 and Q16;

or the agronomically acceptable salts thereof selected from those formed from hydrochloric acid, acetic acid, phosphoric acid and oxalic acid.

A second aspect of this invention relates to herbicidal compositions comprising a compound of formula I and an agronomically acceptable carrier.

A third aspect of this invention relates to a method of controlling a weed comprising applying a herbicidally effective amount of a composition comprising a compound of formula I and an agronomically acceptable carrier to the weed, to the locus of the weed or to the growth medium of said weed.

The following examples of the compounds of formula I are presented in Tables 5–25 and are representative of the invention. In these tables, the abbreviation "Ph" is used to mean phenyl, "Ph-4-Cl" is used to mean 4-chlorophenyl, "Ph-4-F" is used to mean 4-fluorophenyl, "$CH_2Ph$" is used to mean benzyl, "$CH_2Ph$-4-Cl" is used to mean 4-chlorobenzyl, "3-Py" is used to mean 3pyridyl, "Me" is used to mean methyl and "Et" is used to mean ethyl.

TABLE 1

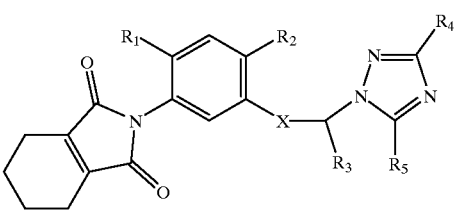

where A = B = N, Q = Q1 in a compound of formula I

| No | $R_1$ | $R_2$ | X | $R_3$ | $R_4$ | $R_5$ |
|----|----|----|----|----|----|----|
| 1 | F | Cl | $CO_2$ | H | H | H |
| 2 | F | Cl | $CO_2$ | $CH_3$ | H | H |
| 3 | F | Cl | $CO_2$ | $C_2H_5$ | H | H |
| 4 | F | Cl | $CO_2$ | $C_3H_7$ | H | H |
| 5 | F | Cl | $CO_2$ | H | $CH_3$ | $CH_3$ |
| 6 | F | Cl | $CO_2$ | $CH_3$ | Ph | $CH_3$ |
| 7 | F | Cl | $CO_2$ | $C_2H_5$ | Ph-4-Cl | H |
| 8 | F | Cl | $CO_2$ | H | H | $SCH_3$ |
| 9 | F | Cl | $CO_2$ | CN | H | H |
| 10 | F | Cl | $CO_2$ | Ph | H | H |
| 11 | F | Cl | $CO_2$ | $CH_2Ph$ | H | H |
| 12 | F | Cl | $CO_2$ | Ph-4-Cl | H | H |
| 13 | F | Cl | $CO_2$ | $CH_2Ph$-4-Cl | H | H |
| 14 | F | Cl | $CO_2$ | 3-Py | H | H |
| 15 | F | Cl | $OCH_2CO_2$ | H | H | H |
| 16 | F | Cl | $OCH_2CO_2$ | $CH_3$ | H | H |
| 17 | F | Cl | $OCH_2CO_2$ | $C_2H_5$ | H | H |
| 18 | F | Cl | $OCH_2CO_2$ | $C_3H_7$ | H | H |
| 19 | F | Cl | $OCH_2CO_2$ | H | $CH_3$ | $CH_3$ |
| 20 | F | Cl | $OCH_2CO_2$ | $CH_3$ | Ph | $CH_3$ |
| 21 | F | Cl | $OCH_2CO_2$ | $C_2H_5$ | Ph-4-Cl | H |
| 22 | F | Cl | $OCH_2CO_2$ | H | H | $SCH_3$ |
| 23 | F | Cl | $OCH_2CO_2$ | CN | H | H |
| 24 | F | Cl | $OCH_2CO_2$ | Ph | H | H |
| 25 | F | Cl | $OCH_2CO_2$ | $CH_2Ph$ | H | H |
| 26 | F | Cl | $OCH_2CO_2$ | Ph-4-Cl | H | H |
| 27 | F | Cl | $OCH_2CO_2$ | $CH_2Ph$-4-Cl | H | H |
| 28 | F | Cl | $OCH_2CO_2$ | 3-Py | H | H |
| 29 | F | Cl | $OCH(CH_3)CO_2$ | H | H | H |
| 30 | F | Cl | $OCH(CH_3)CO_2$ | $CH_3$ | H | H |
| 31 | F | Cl | $OCH(CH_3)CO_2$ | $C_2H_5$ | H | H |
| 32 | F | Cl | $OCH(CH_3)CO_2$ | $C_3H_7$ | H | H |
| 33 | F | Cl | $OCH(CH_3)CO_2$ | H | $CH_3$ | $CH_3$ |
| 34 | F | Cl | $OCH(CH_3)CO_2$ | $CH_3$ | Ph | $CH_3$ |
| 35 | F | Cl | $CH=C(Cl)CO_2$ | H | H | H |
| 36 | F | Cl | $CH_2CH(Cl)CO_2$ | H | H | H |
| 37 | F | Cl | $OCH(CH_3)CO_2$ | CN | H | H |
| 38 | F | Cl | $OCH(CH_3)CO_2$ | Ph | H | H |
| 39 | F | Cl | $OCH(CH_3)CO_2$ | $CH_2Ph$ | H | H |
| 40 | F | Cl | $OCH(CH_3)CO_2$ | Ph-4-Cl | H | H |
| 41 | F | Cl | $OCH(CH_3)CO_2$ | $CH_2Ph$-4-Cl | H | H |
| 42 | F | Cl | $OCH(CH_3)CO_2$ | 3-Py | H | H |
| 43 | F | Cl | O | H | H | H |
| 44 | F | Cl | O | $CH_3$ | H | H |
| 45 | F | Cl | O | $C_2H_5$ | H | H |
| 46 | F | Cl | O | $C_3H_7$ | H | H |
| 47 | F | Cl | O | H | $CH_3$ | $CH_3$ |
| 48 | F | Cl | O | $CH_3$ | Ph | $CH_3$ |
| 49 | F | Cl | O | $C_2H_5$ | Ph-4-Cl | H |
| 50 | F | Cl | O | H | H | $SCH_3$ |
| 51 | F | Cl | O | CN | H | H |
| 52 | F | Cl | O | Ph | H | H |
| 53 | F | Cl | O | $CH_2Ph$ | H | H |
| 54 | F | Cl | O | Ph-4-Cl | H | H |
| 55 | F | Cl | O | $CH_2Ph$-4-Cl | H | H |
| 56 | F | Cl | O | 3-Py | H | H |
| 57 | F | Cl | $SCH_2CO_2$ | H | H | H |
| 58 | F | Cl | $SCH_2CO_2$ | $CH_3$ | H | H |
| 59 | F | Cl | $SCH_2CO_2$ | $C_2H_5$ | H | H |
| 60 | F | Cl | $SCH_2CO_2$ | $C_3H_7$ | H | H |
| 61 | F | Cl | $SCH_2CO_2$ | H | $CH_3$ | $CH_3$ |
| 62 | F | Cl | $SCH_2CO_2$ | $CH_3$ | Ph | $CH_3$ |
| 63 | F | Cl | $SCH_2CO_2$ | $C_2H_5$ | Ph-4-Cl | H |

TABLE 1-continued

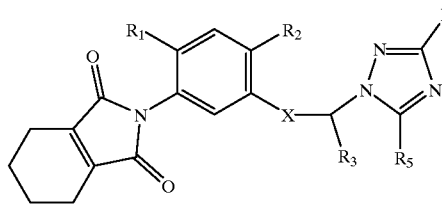

where A = B = N, Q = Q1 in a compound of formula I

| No | R₁ | R₂ | X | R₃ | R₄ | R₅ |
|----|----|----|---|----|----|----|
| 64 | F | Cl | SCH₂CO₂ | H | H | SCH₃ |
| 65 | F | Cl | SCH₂CO₂ | CN | H | H |
| 66 | F | Cl | SCH₂CO₂ | Ph | H | H |
| 67 | F | Cl | SCH₂CO₂ | CH₂Ph | H | H |
| 68 | F | Cl | SCH₂CO₂ | Ph-4-Cl | H | H |
| 69 | F | Cl | SCH₂CO₂ | CH₂Ph-4-Cl | H | H |
| 70 | F | Cl | SCH₂CO₂ | 3-Py | H | H |
| 71 | F | H | SCH(CH₃)CO₂ | H | H | H |
| 72 | F | Cl | SCH(CH₃)CO₂ | CH₃ | H | H |
| 73 | F | Cl | SCH(CH₃)CO₂ | C₂H₅ | H | H |
| 74 | F | Cl | SCH(CH₃)CO₂ | C₃H₇ | H | H |
| 75 | F | Cl | SCH(CH₃)CO₂ | H | CH₃ | CH₃ |
| 76 | F | Cl | SCH(CH₃)CO₂ | CH₃ | Ph | CH₃ |
| 77 | F | Cl | SCH(CH₃)CO₂ | C₂H₅ | Ph-4-Cl | H |
| 78 | F | Cl | SCH(CH₃)CO₂ | H | H | SCH₃ |
| 79 | F | Cl | SCH(CH₃)CO₂ | CN | H | H |
| 80 | F | Cl | SCH(CH₃)CO₂ | Ph | H | H |
| 81 | F | Cl | SCH(CH₃)CO₂ | CH₂Ph | H | H |
| 82 | F | Cl | SCH(CH₃)CO₂ | Ph-4-Cl | H | H |
| 83 | F | Cl | SCH(CH₃)CO₂ | CH₂Ph-4-Cl | H | H |
| 84 | F | Cl | SCH(CH₃)CO₂ | 3-Py | H | H |
| 85 | F | Cl | S | H | H | H |
| 86 | F | Cl | S | CH₃ | H | H |
| 87 | F | Cl | S | C₂H₅ | H | H |
| 88 | F | Cl | S | C₃H₇ | H | H |
| 89 | F | Cl | S | H | CH₃ | CH₃ |
| 90 | F | Cl | S | CH₃ | Ph | CH₃ |
| 91 | F | Cl | S | C₂H₅ | Ph-4-Cl | H |
| 92 | F | Cl | S | H | H | SCH₃ |
| 93 | F | Cl | S | CN | H | H |
| 94 | F | Cl | S | Ph | H | H |
| 95 | F | Cl | S | CH₂Ph | H | H |

TABLE 1-continued

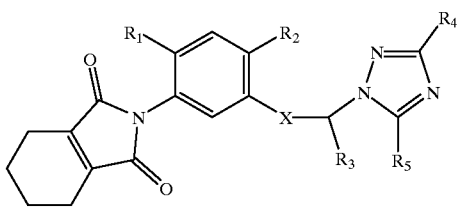

where A = B = N, Q = Q1 in a compound of formula I

| No | R₁ | R₂ | X | R₃ | R₄ | R₅ |
|----|----|----|---|----|----|----|
| 96 | F | Cl | S | Ph-4-Cl | H | H |
| 97 | F | Cl | S | CH₂Ph-4-Cl | H | H |
| 98 | F | Cl | S | 3-Py | H | H |
| 99 | F | Cl | CH=C(Cl)CO₂ | CN | H | H |
| 100 | F | Cl | CH₂CH(Cl)CO₂ | CN | H | H |
| 101 | F | Cl | CH=C(Cl)CO₂ | CH₃ | H | H |
| 102 | F | Cl | CH₂CH(Cl)CO₂ | CH₃ | H | H |
| 103 | Cl | Cl | O | H | H | H |
| 104 | Cl | Cl | OCH₂CO₂ | H | H | H |
| 105 | Cl | Cl | OCH(CH₃)CO₂ | H | H | H |
| 106 | Cl | Cl | CH=C(Cl)CO₂ | H | H | H |
| 107 | Cl | Cl | CH₂CH(Cl)CO₂ | H | H | H |
| 108 | Cl | Cl | CH₂CH(Cl)CO₂ | CH₃ | H | H |
| 109 | Cl | Cl | SCH₂CO₂ | H | H | H |
| 110 | Cl | Cl | SCH(CH₃)CO₂ | H | H | H |
| 111 | Cl | Cl | CO₂ | H | H | H |
| 112 | H | Cl | O | H | H | H |
| 113 | H | Cl | OCH₂CO₂ | H | H | H |
| 114 | H | Cl | OCH(CH₃)CO₂ | H | H | H |
| 115 | H | Cl | CH=C(Cl)CO₂ | H | H | H |
| 116 | H | Cl | CH₂CH(Cl)CO₂ | H | H | H |
| 117 | H | Cl | S | H | H | H |
| 118 | H | Cl | SCH₂CO₂ | H | H | H |
| 119 | H | Cl | SCH(CH₃)CO₂ | H | H | H |
| 120 | H | Cl | CH=C(Cl)CO₂ | H | H | H |
| 121 | H | Cl | CH₂CH(Cl)CO₂ | H | H | H |
| 122 | H | Cl | CO₂ | H | H | H |
| 123 | F | Cl | OCH₂CONH | H | H | H |
| 124 | F | Cl | SCH₂CONH | H | H | H |

TABLE 2

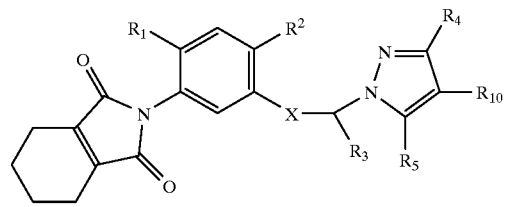

where A = N, B = CR₁₀ and Q = Q1 in a compound of formula I

| No | R₁ | R₂ | X | R₃ | R₄ | R₅ | R₁₀ |
|----|----|----|---|----|----|----|-----|
| 125 | F | Cl | CO₂ | H | H | H | H |
| 126 | F | Cl | CO₂ | CH₃ | H | H | H |
| 127 | F | Cl | CO₂ | C₂H₅ | H | H | H |
| 128 | Cl | Cl | CO₂ | H | Cl | Cl | CO₂CH₃ |
| 129 | F | Cl | CO₂ | H | CH₃ | CH₃ | H |
| 130 | F | Cl | CO₂ | CH₃ | Ph | CH₃ | H |
| 131 | F | Cl | CO₂ | C₂H₅ | Ph-4-Cl | H | H |
| 132 | F | Cl | CO₂ | H | C₂H₅ | CO₂Et | H |
| 133 | F | Cl | CO₂ | CN | H | H | H |
| 134 | F | Cl | CO₂ | Ph | H | H | H |
| 135 | F | Cl | CO₂ | CH₂Ph | H | H | H |

TABLE 2-continued

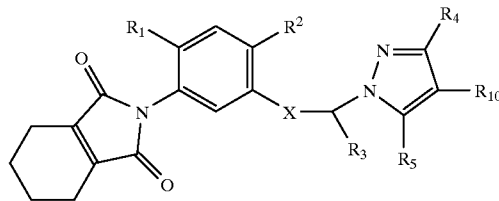

where A = N, B = $CR_{10}$ and Q = Q1 in a compound of formula I

| No | $R_1$ | $R_2$ | X | $R_3$ | $R_4$ | $R_5$ | $R_{10}$ |
|---|---|---|---|---|---|---|---|
| 136 | F | Cl | $CO_2$ | Ph-4-Cl | H | H | H |
| 137 | F | Cl | $CO_2$ | $CH_2$Ph-4-Cl | H | H | H |
| 138 | F | Cl | $CO_2$ | 3-Py | H | H | H |
| 139 | F | Cl | $OCH_2CO_2$ | H | H | H | H |
| 140 | F | Cl | $OCH_2CO_2$ | $CH_3$ | H | H | H |
| 141 | F | Cl | $OCH_2CO_2$ | $C_2H_5$ | H | H | H |
| 142 | F | Cl | $OCH_2CO_2$ | H | Cl | Cl | $CO_2CH_3$ |
| 143 | F | Cl | $OCH_2CO_2$ | H | $CH_3$ | $CH_3$ | H |
| 144 | F | Cl | $OCH_2CO_2$ | $CH_3$ | Ph | $CH_3$ | H |
| 145 | F | Cl | $OCH_2CO_2$ | $C_2H_5$ | Ph-4-Cl | H | H |
| 146 | F | Cl | $OCH_2CO_2$ | H | $C_2H_5$ | $CO_2$Et | H |
| 147 | F | Cl | $OCH_2CO_2$ | CN | H | H | H |
| 148 | F | Cl | $OCH_2CO_2$ | Ph | H | H | H |
| 149 | F | Cl | $OCH_2CO_2$ | $CH_2$Ph | H | H | H |
| 150 | F | Cl | $OCH_2CO_2$ | Ph-4-Cl | H | H | H |
| 151 | F | Cl | $OCH_2CO_2$ | $CH_2$Ph-4-Cl | H | H | H |
| 152 | F | Cl | $OCH_2CO_2$ | 3-Py | H | H | H |
| 153 | F | Cl | $OCH(CH_3)CO_2$ | H | H | H | H |
| 154 | F | Cl | $OCH(CH_3)CO_2$ | $CH_3$ | H | H | H |
| 155 | F | Cl | $OCH(CH_3)CO_2$ | $C_2H_5$ | H | H | H |
| 156 | F | Cl | $OCH(CH_3)CO_2$ | H | Cl | Cl | $CO_2CH_3$ |
| 157 | F | Cl | $OCH(CH_3)CO_2$ | H | $CH_3$ | $CH_3$ | H |
| 158 | F | Cl | $OCH(CH_3)CO_2$ | $CH_3$ | Ph | $CH_3$ | H |
| 159 | F | Cl | $OCH(CH_3)CO_2$ | $C_2H_5$ | Ph-4-Cl | H | H |
| 160 | F | Cl | $OCH(CH_3)CO_2$ | H | $C_2H_5$ | $CO_2$Et | H |
| 161 | F | Cl | $OCH(CH_3)CO_2$ | CN | H | H | H |
| 162 | F | Cl | $OCH(CH_3)CO_2$ | Ph | H | H | H |
| 163 | F | Cl | $OCH(CH_3)CO_2$ | $CH_2$Ph | H | H | H |
| 164 | F | Cl | $OCH(CH_3)CO_2$ | Ph-4-Cl | H | H | H |
| 165 | F | Cl | $OCH(CH_3)CO_2$ | $CH_2$Ph-4-Cl | H | H | H |
| 166 | F | Cl | $OCH(CH_3)CO_2$ | 3-Py | H | H | H |
| 167 | F | Cl | O | H | H | H | H |
| 168 | F | Cl | O | $CH_3$ | H | H | H |
| 169 | F | Cl | O | $C_2H_5$ | H | H | H |
| 170 | F | Cl | O | H | Cl | Cl | $CO_2CH_3$ |
| 171 | F | Cl | O | H | $CH_3$ | $CH_3$ | H |
| 172 | F | Cl | O | $CH_3$ | Ph | $CH_3$ | H |
| 173 | F | Cl | O | $C_2H_5$ | Ph-4-Cl | H | H |
| 174 | F | Cl | O | H | $C_2H_5$ | $CO_2$Et | H |
| 175 | F | Cl | O | CN | H | H | H |
| 176 | F | Cl | O | Ph | H | H | H |
| 177 | F | Cl | O | $CH_2$Ph | H | H | H |
| 178 | F | Cl | O | Ph-4-Cl | H | H | H |
| 179 | F | Cl | O | $CH_2$Ph-4-Cl | H | H | H |
| 180 | F | Cl | O | 3-Py | H | H | H |
| 181 | F | Cl | $SCH_2CO_2$ | H | H | H | H |
| 182 | F | Cl | $SCH_2CO_2$ | $CH_3$ | H | H | H |
| 183 | F | Cl | $SCH_2CO_2$ | $C_2H_5$ | H | H | H |
| 184 | F | Cl | $SCH_2CO_2$ | H | Cl | Cl | $CO_2CH_3$ |
| 185 | F | Cl | $SCH_2CO_2$ | H | $CH_3$ | $CH_3$ | H |
| 186 | F | Cl | $SCH_2CO_2$ | $CH_3$ | Ph | $CH_3$ | H |
| 187 | F | Cl | $SCH_2CO_2$ | $C_2H_5$ | Ph-4-Cl | H | H |
| 188 | F | Cl | $SCH_2CO_2$ | H | $C_2H_5$ | $CO_2$Et | H |
| 189 | F | Cl | $SCH_2CO_2$ | CN | H | H | H |
| 190 | F | Cl | $SCH_2CO_2$ | Ph | H | H | H |
| 191 | F | Cl | $SCH_2CO_2$ | $CH_2$Ph | H | H | H |
| 192 | F | Cl | $SCH_2CO_2$ | Ph-4-Cl | H | H | H |
| 193 | F | Cl | $SCH_2CO_2$ | $CH_2$Ph-4-Cl | H | H | H |
| 194 | F | Cl | $SCH_2CO_2$ | 3-Py | H | H | H |
| 195 | F | Cl | $SCH(CH_3)CO_2$ | H | H | H | H |
| 196 | F | Cl | $SCH(CH_3)CO_2$ | $CH_3$ | H | H | H |
| 197 | F | Cl | $SCH(CH_3)CO_2$ | $C_2H_5$ | H | H | H |
| 198 | F | Cl | $SCH(CH_3)CO_2$ | H | Cl | Cl | $CO_2CH_3$ |
| 199 | F | Cl | $SCH(CH_3)CO_2$ | H | $CH_3$ | $CH_3$ | H |

TABLE 2-continued

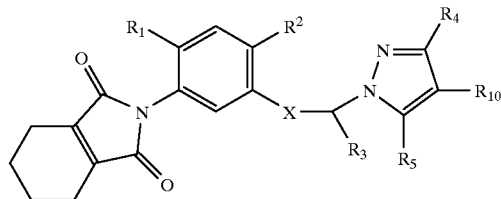

where A = N, B = CR$_{10}$ and Q = Q1 in a compound of formula I

| No | R$_1$ | R$_2$ | X | R$_3$ | R$_4$ | R$_5$ | R$_{10}$ |
|---|---|---|---|---|---|---|---|
| 200 | F | Cl | SCH(CH$_3$)CO$_2$ | CH$_3$ | Ph | CH$_3$ | H |
| 201 | F | Cl | SCH(CH$_3$)CO$_2$ | C$_2$H$_5$ | Ph-4-Cl | H | H |
| 202 | F | Cl | SCH(CH$_3$)CO$_2$ | H | C$_2$H$_5$ | CO$_2$Et | H |
| 203 | F | Cl | SCH(CH$_3$)CO$_2$ | CN | H | H | H |
| 204 | F | Cl | SCH(CH$_3$)CO$_2$ | Ph | H | H | H |
| 205 | F | Cl | SCH(CH$_3$)CO$_2$ | CH$_2$Ph | H | H | H |
| 206 | F | Cl | SCH(CH$_3$)CO$_2$ | Ph-4-Cl | H | H | H |
| 207 | F | Cl | SCH(CH$_3$)CO$_2$ | CH$_2$Ph-4-Cl | H | H | H |
| 208 | F | Cl | SCH(CH$_3$)CO$_2$ | 3-Py | H | H | H |
| 209 | F | Cl | S | H | H | H | H |
| 210 | F | Cl | S | CH$_3$ | H | H | H |
| 211 | F | Cl | S | C$_2$H$_5$ | H | H | H |
| 212 | F | Cl | S | H | Cl | Cl | CO$_2$CH$_3$ |
| 213 | F | Cl | S | H | CH$_3$ | CH$_3$ | H |
| 214 | F | Cl | S | CH$_3$ | Ph | CH$_3$ | H |
| 215 | F | Cl | S | C$_2$H$_5$ | Ph-4-Cl | H | H |
| 216 | F | Cl | S | H | C$_2$H$_5$ | CO$_2$Et | H |
| 217 | F | Cl | S | CN | H | H | H |
| 218 | F | Cl | S | Ph | H | H | H |
| 219 | F | Cl | S | CH$_2$Ph | H | H | H |
| 220 | F | Cl | S | Ph-4-Cl | H | H | H |
| 221 | F | Cl | S | CH$_2$Ph-4-Cl | H | H | H |
| 222 | F | Cl | S | 3-Py | H | H | H |
| 223 | F | Cl | CH=C(Cl)CO$_2$ | H | H | H | H |
| 224 | F | Cl | CH$_2$CH(Cl)CO$_2$ | H | H | H | H |
| 225 | Cl | Cl | O | H | H | H | H |
| 226 | Cl | Cl | OCH$_2$CO$_2$ | H | H | H | H |
| 227 | Cl | Cl | S | H | H | H | H |
| 228 | Cl | Cl | SCH$_2$CO$_2$ | H | H | H | H |
| 229 | Cl | Cl | SCH(CH$_3$)CO$_2$ | H | H | H | H |
| 230 | Cl | Cl | CO$_2$ | H | H | H | H |
| 231 | H | Cl | O | H | H | H | H |
| 232 | H | Cl | OCH$_2$CO$_2$ | H | H | H | H |
| 233 | H | Cl | S | H | H | H | H |
| 234 | H | Cl | SCH$_2$CO$_2$ | H | H | H | H |
| 235 | H | Cl | CO$_2$ | H | H | H | H |

TABLE 3

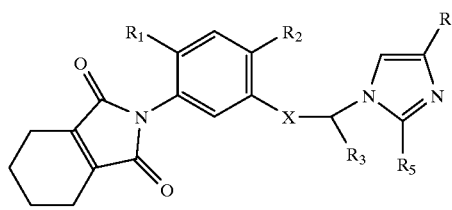

where A = CH, B = N and Q = Q1 in a compound of formula I

| No | R$_1$ | R$_2$ | X | R$_3$ | R$_4$ | R$_5$ |
|---|---|---|---|---|---|---|
| 236 | F | Cl | CO$_2$ | H | H | H |
| 237 | F | Cl | CO$_2$ | CH$_3$ | H | H |
| 238 | F | Cl | CO$_2$ | C$_2$H$_5$ | H | H |
| 239 | F | Cl | CO$_2$ | H | Cl | Cl |
| 240 | F | Cl | CO$_2$ | H | CH$_3$ | CH$_3$ |
| 241 | F | Cl | CO$_2$ | CH$_3$ | Ph | CH$_3$ |

TABLE 3-continued

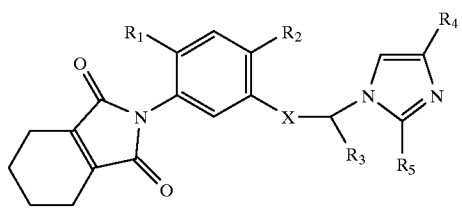

where A = CH, B = N and Q = Q1 in a compound of formula I

| No | R$_1$ | R$_2$ | X | R$_3$ | R$_4$ | R$_5$ |
|---|---|---|---|---|---|---|
| 242 | F | Cl | CO$_2$ | C$_2$H$_5$ | Ph-4-Cl | H |
| 243 | F | Cl | CO$_2$ | H | Ph-4-Cl | CH$_3$ |
| 244 | F | Cl | CO$_2$ | CN | H | H |
| 245 | F | Cl | CO$_2$ | Ph | H | H |
| 246 | F | Cl | CO$_2$ | CH$_2$Ph | H | H |
| 247 | F | Cl | CO$_2$ | Ph-4-Cl | H | H |

TABLE 3-continued

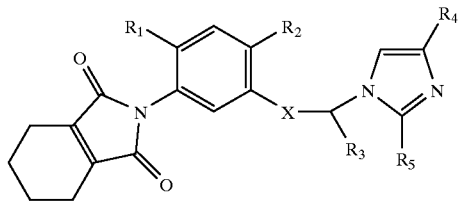

where A = CH, B = N and Q = Q1 in a compound of formula I

| No | R₁ | R₂ | X | R₃ | R₄ | R₅ |
|---|---|---|---|---|---|---|
| 248 | F | Cl | CO₂ | CH₂Ph-4-Cl | H | H |
| 249 | F | Cl | CO₂ | 3-Py | H | H |
| 250 | F | Cl | OCH₂CO₂ | H | H | H |
| 251 | F | Cl | OCH₂CO₂ | CH₃ | H | H |
| 252 | F | Cl | OCH₂CO₂ | C₂H₅ | H | H |
| 253 | F | Cl | OCH₂CO₂ | H | Cl | Cl |
| 254 | F | Cl | OCH₂CO₂ | H | CH₃ | CH₃ |
| 255 | F | Cl | OCH₂CO₂ | CH₃ | Ph | CH₃ |
| 256 | F | Cl | OCH₂CO₂ | C₂H₅ | Ph-4-Cl | H |
| 257 | F | Cl | OCH₂CO₂ | H | Ph-4-Cl | CH₃ |
| 258 | F | Cl | OCH₂CO₂ | CN | H | H |
| 259 | F | Cl | OCH₂CO₂ | Ph | H | H |
| 260 | F | Cl | OCH₂CO₂ | CH₂Ph | H | H |
| 261 | F | Cl | OCH₂CO₂ | Ph-4-Cl | H | H |
| 262 | F | Cl | OCH₂CO₂ | CH₂Ph-4-Cl | H | H |
| 263 | F | Cl | OCH₂CO₂ | 3-Py | H | H |
| 264 | F | Cl | OCH(CH₃)CO₂ | H | H | H |
| 265 | F | Cl | OCH(CH₃)CO₂ | CH₃ | H | H |
| 266 | F | Cl | OCH(CH₃)CO₂ | C₂H₅ | H | H |
| 267 | F | Cl | OCH(CH₃)CO₂ | H | Cl | Cl |
| 268 | F | Cl | OCH(CH₃)CO₂ | H | CH₃ | CH₃ |
| 269 | F | Cl | OCH(CH₃)CO₂ | CH₃ | Ph | CH₃ |
| 270 | F | Cl | OCH(CH₃)CO₂ | C₂H₅ | Ph-4-Cl | H |
| 271 | F | Cl | OCH(CH₃)CO₂ | H | Ph-4-Cl | CH₃ |
| 272 | F | Cl | OCH(CH₃)CO₂ | CN | H | H |
| 273 | F | Cl | OCH(CH₃)CO₂ | Ph | H | H |
| 274 | F | Cl | OCH(CH₃)CO₂ | CH₂Ph | H | H |
| 275 | F | Cl | OCH(CH₃)CO₂ | Ph-4-Cl | H | H |
| 276 | F | Cl | OCH(CH₃)CO₂ | CH₂Ph-4-Cl | H | H |
| 277 | F | Cl | OCH(CH₃)CO₂ | 3-Py | H | H |
| 278 | F | Cl | O | H | H | H |
| 279 | F | Cl | O | CH₃ | H | H |
| 280 | F | Cl | O | C₂H₅ | H | H |
| 281 | F | Cl | O | H | Cl | Cl |
| 282 | F | Cl | O | H | CH₃ | CH₃ |
| 283 | F | Cl | O | CH₃ | Ph | CH₃ |
| 284 | F | Cl | O | C₂H₅ | Ph-4-Cl | H |
| 285 | F | Cl | O | H | Ph-4-Cl | CH₃ |
| 286 | F | Cl | O | CN | H | H |
| 287 | F | Cl | O | Ph | H | H |
| 288 | F | Cl | O | CH₂Ph | H | H |
| 289 | F | Cl | O | Ph-4-Cl | H | H |
| 290 | F | Cl | O | CH₂Ph-4-Cl | H | H |
| 291 | F | Cl | O | 3-Py | H | H |
| 292 | F | Cl | SCH₂CO₂ | H | H | H |
| 293 | F | Cl | SCH₂CO₂ | CH₃ | H | H |
| 294 | F | Cl | SCH₂CO₂ | C₂H₅ | H | H |
| 295 | F | Cl | SCH₂CO₂ | H | Cl | Cl |
| 296 | F | Cl | SCH₂CO₂ | H | CH₃ | CH₃ |
| 297 | F | Cl | SCH₂CO₂ | CH₃ | Ph | CH₃ |
| 298 | F | Cl | SCH₂CO₂ | C₂H₅ | Ph-4-Cl | H |
| 299 | F | Cl | SCH₂CO₂ | H | Ph-4-Cl | CH₃ |
| 300 | F | Cl | SCH₂CO₂ | CN | H | H |
| 301 | F | Cl | SCH₂CO₂ | Ph | H | H |
| 302 | F | Cl | SCH₂CO₂ | CH₂Ph | H | H |
| 303 | F | Cl | SCH₂CO₂ | Ph-4-Cl | H | H |
| 304 | F | Cl | SCH₂CO₂ | CH₂Ph-4-Cl | H | H |
| 305 | F | Cl | SCH₂CO₂ | 3-Py | H | H |
| 306 | F | Cl | SCH(CH₃)CO₂ | H | H | H |
| 307 | F | Cl | SCH(CH₃)CO₂ | CH₃ | H | H |
| 308 | F | Cl | SCH(CH₃)CO₂ | C₂H₅ | H | H |
| 309 | F | Cl | SCH(CH₃)CO₂ | H | Cl | Cl |
| 310 | F | Cl | SCH(CH₃)CO₂ | H | CH₃ | CH₃ |
| 311 | F | Cl | SCH(CH₃)CO₂ | CH₃ | Ph | CH₃ |

TABLE 3-continued

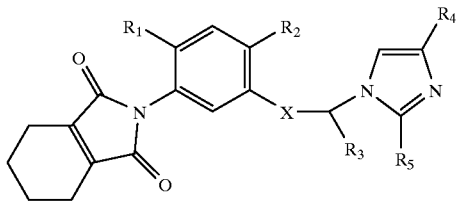

where A = CH, B = N and Q = Q1 in a compound of formula I

| No | R₁ | R₂ | X | R₃ | R₄ | R₅ |
|---|---|---|---|---|---|---|
| 312 | F | Cl | SCH(CH₃)CO₂ | C₂H₅ | Ph-4-Cl | H |
| 313 | F | Cl | SCH(CH₃)CO₂ | H | Ph-4-Cl | CH₃ |
| 314 | F | Cl | SCH(CH₃)CO₂ | CN | H | H |
| 315 | F | Cl | SCH(CH₃)CO₂ | Ph | H | H |
| 316 | F | Cl | S | H | H | H |
| 317 | F | Cl | S | CH₃ | H | H |
| 318 | F | Cl | S | C₂H₅ | H | H |
| 319 | F | Cl | S | H | Cl | Cl |
| 320 | F | Cl | S | H | CH₃ | CH₃ |
| 321 | F | Cl | S | CH₃ | Ph | CH₃ |
| 322 | F | Cl | S | C₂H₅ | Ph-4-Cl | H |
| 323 | F | Cl | CH=C(Cl)CO₂ | H | H | H |
| 324 | F | Cl | CH₂CH(Cl)CO₂ | H | H | H |
| 325 | F | Cl | S | Ph | H | H |
| 326 | F | Cl | S | CH₂Ph | CH₃ | CH₃ |
| 327 | F | Cl | S | Ph-4-Cl | H | H |
| 328 | Cl | Cl | O | H | H | H |
| 329 | Cl | Cl | OCH₂CO₂ | H | H | H |
| 330 | Cl | Cl | S | H | H | H |
| 331 | Cl | Cl | SCH₂CO₂ | H | H | H |
| 332 | Cl | Cl | SCH(CH₃)CO₂ | H | H | H |
| 333 | Cl | Cl | CO₂ | H | H | H |
| 334 | H | Cl | O | H | H | H |
| 335 | H | Cl | OCH₂CO₂ | H | H | H |
| 336 | H | Cl | S | H | H | H |
| 337 | H | Cl | SCH₂CO₂ | H | H | H |
| 338 | H | Cl | CO₂ | H | H | H |

TABLE 4 where A = B = N, R₄ = R₅ = H and Q = Q2 in a compound of formula I

| No | R₁ | R₂ | X | R₃ |
|---|---|---|---|---|
| 339 | F | Cl | CO₂ | H |
| 340 | F | Cl | CO₂ | CH₃ |
| 341 | F | Cl | CO₂ | C₂H₅ |
| 342 | F | Cl | CO₂ | Ph |
| 343 | F | Cl | CO₂ | CH₂Ph |
| 344 | F | Cl | CO₂ | Ph-4-Cl |
| 345 | F | Cl | CO₂ | CN |
| 346 | F | Cl | CO₂ | 3-Py |
| 347 | F | Cl | OCH₂CO₂ | H |
| 348 | F | Cl | OCH₂CO₂ | CH₃ |
| 349 | F | Cl | OCH₂CO₂ | C₂H₅ |
| 350 | F | Cl | OCH₂CO₂ | Ph |
| 351 | F | Cl | OCH₂CO₂ | CH₂Ph |
| 352 | F | Cl | OCH₂CO₂ | Ph-4-Cl |

TABLE 4-continued

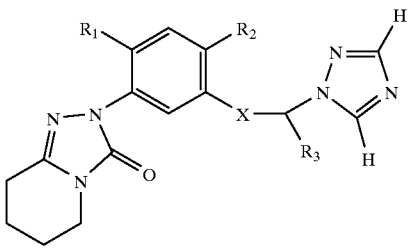

where A = B = N, R₄ = R₅ = H and Q = Q2 in a compound of formula I

| No | R₁ | R₂ | X | R₃ |
|---|---|---|---|---|
| 353 | F | Cl | OCH₂CO₂ | CN |
| 354 | F | Cl | OCH₂CO₂ | 3-Py |
| 355 | F | Cl | OCH(CH₃)CO₂ | H |
| 356 | F | Cl | OCH(CH₃)CO₂ | CH₃ |
| 357 | F | Cl | OCH(CH₃)CO₂ | C₂H₅ |
| 358 | F | Cl | OCH(CH₃)CO₂ | Ph |
| 359 | F | Cl | OCH(CH₃)CO₂ | CH₂Ph |
| 360 | F | Cl | OCH(CH₃)CO₂ | Ph-4-Cl |
| 361 | F | Cl | CH=C(Cl)CO₂ | H |
| 362 | F | Cl | CH₂CH(Cl)CO₂ | H |
| 363 | F | Cl | O | H |
| 364 | F | Cl | O | CH₃ |
| 365 | F | Cl | O | C₂H₅ |
| 366 | F | Cl | O | Ph |
| 367 | F | Cl | O | CH₂Ph |
| 368 | F | Cl | CH=C(Cl)CO₂ | CN |
| 369 | F | Cl | CH₂CH(Cl)CO₂ | CN |
| 370 | F | Cl | O | 3-Py |
| 371 | F | Cl | SCH₂CO₂ | H |
| 372 | F | Cl | SCH₂CO₂ | CH₃ |
| 373 | F | Cl | SCH₂CO₂ | C₂H₅ |
| 374 | F | Cl | SCH₂CO₂ | Ph |
| 375 | F | Cl | SCH₂CO₂ | CH₂Ph |
| 376 | F | Cl | SCH₂CO₂ | Ph-4-Cl |
| 377 | F | Cl | SCH₂CO₂ | CN |
| 378 | F | Cl | SCH₂CO₂ | 3-Py |
| 379 | F | H | SCH(CH₃)CO₂ | H |
| 380 | F | Cl | SCH(CH₃)CO₂ | CH₃ |
| 381 | F | Cl | SCH(CH₃)CO₂ | C₂H₅ |
| 382 | F | Cl | SCH(CH₃)CO₂ | Ph |
| 383 | F | Cl | SCH(CH₃)CO₂ | CH₂Ph |
| 384 | F | Cl | SCH(CH₃)CO₂ | Ph-4-Cl |
| 385 | F | Cl | SCH(CH₃)CO₂ | CH₂Ph-4-Cl |
| 386 | F | Cl | SCH(CH₃)CO₂ | 3-Py |
| 387 | F | Cl | S | H |
| 388 | F | Cl | S | CH₃ |
| 389 | F | Cl | S | C₂H₅ |
| 390 | F | Cl | S | Ph |
| 391 | F | Cl | S | CH₂Ph |
| 392 | F | Cl | S | Ph-4-Cl |
| 393 | F | Cl | S | CH₂Ph-4-Cl |
| 394 | F | Cl | S | 3-Py |
| 395 | Cl | Cl | O | H |
| 396 | Cl | Cl | OCH₂CO₂ | H |
| 397 | Cl | Cl | OCH(CH₃)CO₂ | H |
| 398 | Cl | Cl | CH=C(Cl)CO₂ | H |
| 399 | Cl | Cl | CH₂CH(Cl)CO₂ | H |
| 400 | Cl | Cl | S | H |
| 401 | Cl | Cl | SCH₂CO₂ | H |
| 402 | Cl | Cl | SCH(CH₃)CO₂ | H |
| 403 | Cl | Cl | CO₂ | H |
| 404 | H | Cl | O | H |
| 405 | H | Cl | OCH₂CO₂ | H |
| 406 | H | Cl | OCH(CH₃)CO₂ | H |
| 407 | H | Cl | CH=C(Cl)CO₂ | H |
| 408 | H | Cl | CH₂CH(Cl)CO₂ | H |
| 409 | H | Cl | S | H |
| 410 | H | Cl | SCH₂CO₂ | H |
| 411 | H | Cl | SCH(CH₃)CO₂ | H |
| 412 | H | Cl | CH=C(Cl)CO₂ | H |
| 413 | H | Cl | CH₂CH(Cl)CO₂ | H |
| 414 | H | Cl | CO₂ | H |

TABLE 4-continued

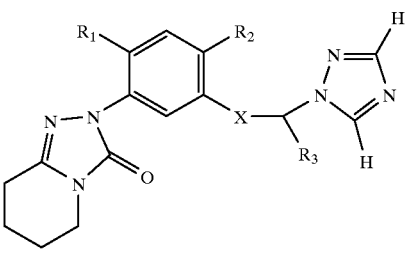

where A = B = N, R₄ = R₅ = H and Q = Q2 in a compound of formula I

| No | R₁ | R₂ | X | R₃ |
|---|---|---|---|---|
| 415 | F | Cl | OCH₂CO₂ | Ph-4-F |
| 416 | F | Cl | SCH₂CO₂ | Ph-4-F |

TABLE 5

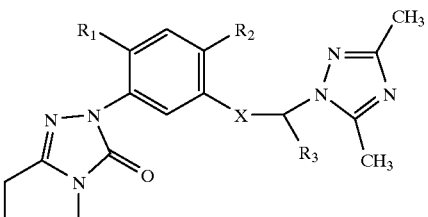

where A = N, B = CH, R₄ = R₅ = CH₃, Q = Q2 in a compound of formula I

| No | R₁ | R₂ | X | R₃ |
|---|---|---|---|---|
| 417 | F | Cl | CO₂ | H |
| 418 | F | Cl | CO₂ | CH₃ |
| 419 | F | Cl | CO₂ | C₂H₅ |
| 420 | F | Cl | CO₂ | Ph |
| 421 | F | Cl | CO₂ | CH₂Ph |
| 422 | F | Cl | CO₂ | Ph-4-Cl |
| 423 | F | Cl | CO₂ | CN |
| 424 | F | Cl | CO₂ | 3-Py |
| 425 | F | Cl | OCH₂CO₂ | H |
| 426 | F | Cl | OCH₂CO₂ | CH₃ |
| 427 | F | Cl | OCH₂CO₂ | C₂H₅ |
| 428 | F | Cl | OCH₂CO₂ | Ph |
| 429 | F | Cl | OCH₂CO₂ | CH₂Ph |
| 430 | F | Cl | OCH₂CO₂ | Ph-4-Cl |
| 431 | F | Cl | OCH₂CO₂ | CH₂Ph-4-Cl |
| 432 | F | Cl | OCH₂CO₂ | 3-Py |
| 433 | F | Cl | OCH(CH₃)CO₂ | H |
| 434 | F | Cl | OCH(CH₃)CO₂ | CH₃ |
| 435 | F | Cl | OCH(CH₃)CO₂ | C₂H₅ |
| 436 | F | Cl | OCH(CH₃)CO₂ | Ph |
| 437 | F | Cl | OCH(CH₃)CO₂ | CH₂Ph |
| 438 | F | Cl | OCH(CH₃)CO₂ | Ph-4-Cl |
| 439 | F | Cl | OCH(CH₃)CO₂ | CN |
| 440 | F | Cl | OCH(CH₃)CO₂ | 3-Py |
| 441 | F | Cl | O | H |
| 442 | F | Cl | O | CH₃ |
| 443 | F | Cl | O | C₂H₅ |
| 444 | F | Cl | O | Ph |
| 445 | F | Cl | O | CH₂Ph |
| 446 | F | Cl | O | Ph-4-Cl |
| 447 | F | Cl | O | CH₂Ph-4-Cl |
| 448 | F | Cl | O | 3-Py |
| 449 | F | Cl | SCH₂CO₂ | H |
| 450 | F | Cl | SCH₂CO₂ | CH₃ |
| 451 | F | Cl | SCH₂CO₂ | C₂H₅ |
| 452 | F | Cl | SCH₂CO₂ | Ph |

TABLE 5-continued

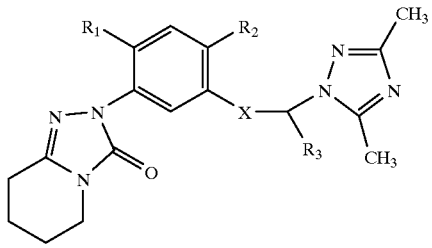

where A = N, B = CH, R₄ = R₅ = CH₃, Q = Q2 in a compound of formula I

| No | R₁ | R₂ | X | R₃ |
|---|---|---|---|---|
| 453 | F | Cl | SCH₂CO₂ | CH₂Ph |
| 454 | F | Cl | SCH₂CO₂ | Ph-4-Cl |
| 455 | F | Cl | SCH₂CO₂ | CH₂Ph-4-Cl |
| 456 | F | Cl | SCH₂CO₂ | 3-Py |
| 457 | F | Cl | SCH(CH₃)CO₂ | H |
| 458 | F | Cl | SCH(CH₃)CO₂ | CH₃ |
| 459 | F | Cl | SCH(CH₃)CO₂ | C₂H₅ |
| 460 | F | Cl | SCH(CH₃)CO₂ | Ph |
| 461 | F | Cl | SCH(CH₃)CO₂ | CH₂Ph |
| 462 | F | Cl | SCH(CH₃)CO₂ | Ph-4-Cl |
| 463 | F | Cl | SCH(CH₃)CO₂ | CH₂Ph-4-Cl |
| 464 | F | Cl | SCH(CH₃)CO₂ | 3-Py |
| 465 | F | Cl | S | H |
| 466 | F | Cl | S | CH₃ |
| 467 | F | Cl | S | C₂H₅ |
| 468 | F | Cl | S | Ph |
| 469 | F | Cl | S | CH₂Ph |
| 470 | F | Cl | S | Ph-4-Cl |
| 471 | F | Cl | S | CH₂Ph-4-Cl |
| 472 | F | Cl | S | 3-Py |
| 473 | Cl | Cl | O | H |
| 474 | Cl | Cl | OCH₂CO₂ | H |
| 475 | Cl | Cl | S | H |
| 476 | Cl | Cl | SCH₂CO₂ | H |
| 477 | Cl | Cl | SCH(CH₃)CO₂ | H |
| 478 | Cl | Cl | CO₂ | H |
| 479 | H | Cl | O | H |
| 480 | H | Cl | OCH₂CO₂ | H |
| 481 | H | Cl | S | H |
| 482 | H | Cl | SCH₂CO₂ | H |
| 483 | H | Cl | CO₂ | H |

TABLE 6

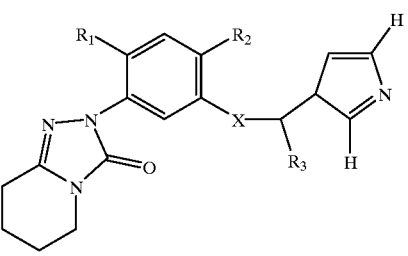

where A = CH, B = N, R₄ = R₅ = H, Q = Q2 in a compound of formula I

| No | R₁ | R₂ | X | R₃ |
|---|---|---|---|---|
| 484 | F | Cl | CO₂ | H |
| 485 | F | Cl | CO₂ | CH₃ |
| 486 | F | Cl | CO₂ | C₂H₅ |
| 487 | F | Cl | CO₂ | Ph |
| 488 | F | Cl | CO₂ | CH₂Ph |
| 489 | F | Cl | CO₂ | Ph-4-Cl |
| 490 | F | Cl | CO₂ | CH₂Ph-4-Cl |
| 491 | F | Cl | CO₂ | 3-Py |
| 492 | F | Cl | OCH₂CO₂ | H |
| 493 | F | Cl | OCH₂CO₂ | CH₃ |
| 494 | F | Cl | OCH₂CO₂ | C₂H₅ |
| 495 | F | Cl | OCH₂CO₂ | Ph |
| 496 | F | Cl | OCH₂CO₂ | CH₂Ph |
| 497 | F | Cl | OCH₂CO₂ | CN |
| 498 | F | Cl | OCH₂CO₂ | CH₂Ph-4-Cl |
| 499 | F | Cl | OCH₂CO₂ | 3-Py |
| 500 | F | Cl | OCH(CH₃)CO₂ | H |
| 501 | F | Cl | OCH(CH₃)CO₂ | CH₃ |
| 502 | F | Cl | OCH(CH₃)CO₂ | C₂H₅ |
| 503 | F | Cl | OCH(CH₃)CO₂ | Ph |
| 504 | F | Cl | OCH(CH₃)CO₂ | CH₂Ph |
| 505 | F | Cl | OCH(CH₃)CO₂ | Ph-4-Cl |
| 506 | F | Cl | OCH(CH₃)CO₂ | CH₂Ph-4-Cl |
| 507 | F | Cl | OCH(CH₃)CO₂ | 3-Py |
| 508 | F | Cl | O | H |
| 509 | F | Cl | O | CH₃ |
| 510 | F | Cl | O | C₂H₅ |
| 511 | F | Cl | O | Ph |
| 512 | F | Cl | O | CH₂Ph |
| 513 | F | Cl | O | Ph-4-Cl |
| 514 | F | Cl | O | CH₂Ph-4-Cl |
| 515 | F | Cl | O | 3-Py |
| 516 | F | Cl | SCH₂CO₂ | H |
| 517 | F | Cl | SCH₂CO₂ | CH₃ |
| 518 | F | Cl | SCH₂CO₂ | C₂H₅ |
| 519 | F | Cl | SCH₂CO₂ | Ph |
| 520 | F | Cl | SCH₂CO₂ | CH₂Ph |
| 521 | F | Cl | SCH₂CO₂ | Ph-4-Cl |
| 522 | F | Cl | SCH₂CO₂ | CH₂Ph-4-Cl |
| 523 | F | Cl | SCH₂CO₂ | 3-Py |
| 524 | F | Cl | SCH(CH₃)CO₂ | H |
| 525 | F | Cl | SCH(CH₃)CO₂ | CH₃ |
| 526 | F | Cl | SCH(CH₃)CO₂ | C₂H₅ |
| 527 | F | Cl | SCH(CH₃)CO₂ | Ph |
| 528 | F | Cl | SCH(CH₃)CO₂ | CH₂Ph |
| 529 | F | Cl | SCH(CH₃)CO₂ | Ph-4-Cl |
| 530 | F | Cl | SCH(CH₃)CO₂ | CH₂Ph-4-Cl |
| 531 | F | Cl | SCH(CH₃)CO₂ | 3-Py |
| 532 | F | Cl | S | H |
| 533 | F | Cl | S | CH₃ |
| 534 | F | Cl | S | C₂H₅ |
| 535 | F | Cl | S | Ph |
| 536 | F | Cl | S | CH₂Ph |
| 537 | F | Cl | S | Ph-4-Cl |
| 538 | F | Cl | S | CH₂Ph-4-Cl |
| 539 | F | Cl | S | 3-Py |
| 540 | Cl | Cl | O | H |
| 541 | Cl | Cl | OCH₂CO₂ | H |
| 542 | Cl | Cl | S | H |
| 543 | Cl | Cl | SCH₂CO₂ | H |
| 544 | Cl | Cl | SCH(CH₃)CO₂ | H |
| 545 | Cl | Cl | CO₂ | H |
| 546 | H | Cl | O | H |
| 547 | H | Cl | OCH₂CO₂ | H |
| 548 | H | Cl | S | H |
| 549 | H | Cl | SCH₂CO₂ | H |
| 550 | H | Cl | CO₂ | H |

TABLE 7

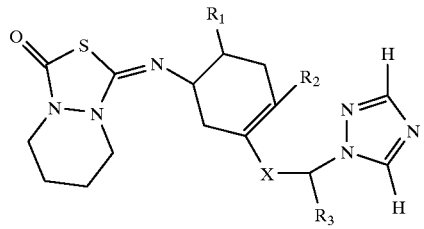

where A = B = N, R4 = R5 = H, Q = Q3 in a compound of formula I

| No | R1 | R2 | X | R3 |
|---|---|---|---|---|
| 551 | F | Cl | $CO_2$ | H |
| 552 | F | Cl | $CO_2$ | $CH_3$ |
| 553 | F | Cl | $CO_2$ | $C_2H_5$ |
| 554 | F | Cl | $CO_2$ | Ph |
| 555 | F | Cl | $CO_2$ | $CH_2Ph$ |
| 556 | F | Cl | $CO_2$ | Ph-4-Cl |
| 557 | F | Cl | $CO_2$ | CN |
| 558 | F | Cl | $CO_2$ | 3-Py |
| 559 | F | Cl | $OCH_2CO_2$ | H |
| 560 | F | Cl | $OCH_2CO_2$ | $CH_3$ |
| 561 | F | Cl | $OCH_2CO_2$ | $C_2H_5$ |
| 562 | F | Cl | $OCH_2CO_2$ | Ph |
| 563 | F | Cl | $OCH_2CO_2$ | $CH_2Ph$ |
| 564 | F | Cl | $OCH_2CO_2$ | Ph-4-Cl |
| 565 | F | Cl | $OCH_2CO_2$ | CN |
| 566 | F | Cl | $OCH_2CO_2$ | 3-Py |
| 567 | F | Cl | $OCH(CH_3)CO_2$ | H |
| 568 | F | Cl | $OCH(CH_3)CO_2$ | $CH_3$ |
| 569 | F | Cl | $OCH(CH_3)CO_2$ | $C_2H_5$ |
| 570 | F | Cl | $OCH(CH_3)CO_2$ | Ph |
| 571 | F | Cl | $OCH(CH_3)CO_2$ | $CH_2Ph$ |
| 572 | F | Cl | $OCH(CH_3)CO_2$ | Ph-4-Cl |
| 573 | F | Cl | $OCH(CH_3)CO_2$ | CN |
| 574 | F | Cl | $OCH(CH_3)CO_2$ | 3-Py |
| 575 | F | Cl | O | H |
| 576 | F | Cl | O | $CH_3$ |
| 577 | F | Cl | O | $C_2H_5$ |
| 578 | F | Cl | O | Ph |
| 579 | F | Cl | O | $CH_2Ph$ |
| 580 | F | Cl | O | Ph-4-Cl |
| 581 | F | Cl | O | $CH_2Ph$-4-Cl |
| 582 | F | Cl | O | 3-Py |
| 583 | F | Cl | $SCH_2CO_2$ | H |
| 584 | F | Cl | $SCH_2CO_2$ | $CH_3$ |
| 585 | F | Cl | $SCH_2CO_2$ | $C_2H_5$ |
| 586 | F | Cl | $SCH_2CO_2$ | Ph |
| 587 | F | Cl | $SCH_2CO_2$ | $CH_2Ph$ |
| 588 | F | Cl | $SCH_2CO_2$ | Ph-4-Cl |
| 589 | F | Cl | $SCH_2CO_2$ | $CH_2Ph$-4-Cl |
| 590 | F | Cl | $SCH_2CO_2$ | 3-Py |
| 591 | F | H | $SCH(CH_3)CO_2$ | H |
| 592 | F | Cl | $SCH(CH_3)CO_2$ | $CH_3$ |
| 593 | F | Cl | $SCH(CH_3)CO_2$ | $C_2H_5$ |
| 594 | F | Cl | $SCH(CH_3)CO_2$ | Ph |
| 595 | F | Cl | $SCH(CH_3)CO_2$ | $CH_2Ph$ |
| 596 | F | Cl | $SCH(CH_3)CO_2$ | Ph-4-Cl |
| 597 | F | Cl | $SCH(CH_3)CO_2$ | $CH_2Ph$-4-Cl |
| 598 | F | Cl | $SCH(CH_3)CO_2$ | 3-Py |
| 599 | F | Cl | S | H |
| 600 | F | Cl | S | $CH_3$ |
| 601 | F | Cl | S | $C_2H_5$ |
| 602 | F | Cl | S | Ph |
| 603 | F | Cl | S | $CH_2Ph$ |
| 604 | F | Cl | S | Ph-4-Cl |
| 605 | F | Cl | S | $CH_2Ph$-4-Cl |
| 606 | F | Cl | S | 3-Py |
| 607 | F | Cl | $CH{=}C(Cl)CO_2$ | H |
| 608 | F | Cl | $CH_2CH(Cl)CO_2$ | H |
| 609 | Cl | Cl | O | H |
| 610 | Cl | Cl | $OCH_2CO_2$ | H |
| 611 | Cl | Cl | $CH{=}C(Cl)CO_2$ | H |
| 612 | Cl | Cl | $CH_2CH(Cl)CO_2$ | H |

TABLE 7-continued

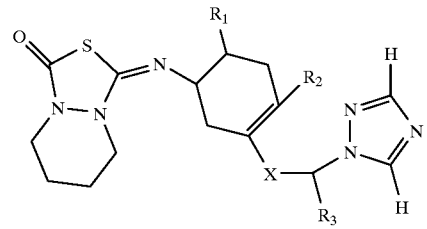

where A = B = N, R4 = R5 = H, Q = Q3 in a compound of formula I

| No | R1 | R2 | X | R3 |
|---|---|---|---|---|
| 613 | Cl | Cl | $SCH_2CO_2$ | H |
| 614 | Cl | Cl | $SCH(CH_3)CO_2$ | H |
| 615 | Cl | Cl | $CO_2$ | H |
| 616 | H | Cl | $OCH_2CO_2$ | H |
| 617 | H | Cl | $CH{=}C(Cl)CO_2$ | H |
| 618 | H | Cl | $CH_2CH(Cl)CO_2$ | H |
| 619 | H | Cl | S | H |
| 620 | H | Cl | $SCH_2CO_2$ | H |
| 621 | H | Cl | $SCH(CH_3)CO_2$ | H |
| 622 | H | Cl | $CO_2$ | H |
| 623 | F | Cl | $OCH_2CO_2$ | Ph-4-F |
| 624 | F | Cl | $SCH_2CO_2$ | Ph-4-F |

TABLE 8

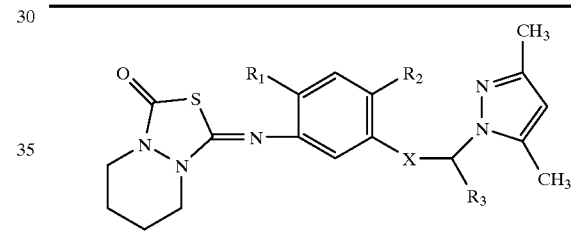

where A = N, B = CH, R4 = R5 = $CH_3$, Q = Q3 in a compound of formula I

| No | R1 | R2 | X | R3 |
|---|---|---|---|---|
| 625 | F | Cl | $CO_2$ | H |
| 626 | F | Cl | $CO_2$ | $CH_3$ |
| 627 | F | Cl | $CO_2$ | $C_2H_5$ |
| 628 | F | Cl | $CO_2$ | Ph |
| 629 | F | Cl | $CO_2$ | $CH_2Ph$ |
| 630 | F | Cl | $CO_2$ | Ph-4-Cl |
| 631 | F | Cl | $CO_2$ | $CH_2Ph$-4-Cl |
| 632 | F | Cl | $CO_2$ | 3-Py |
| 633 | F | Cl | $OCH_2CO_2$ | H |
| 634 | F | Cl | $OCH_2CO_2$ | $CH_3$ |
| 635 | F | Cl | $OCH_2CO_2$ | $C_2H_5$ |
| 636 | F | Cl | $OCH_2CO_2$ | Ph |
| 637 | F | Cl | $OCH_2CO_2$ | $CH_2Ph$ |
| 638 | F | Cl | $OCH_2CO_2$ | Ph-4-Cl |
| 639 | F | Cl | $OCH_2CO_2$ | $CH_2Ph$-4-Cl |
| 640 | F | Cl | $OCH_2CO_2$ | 3-Py |
| 641 | F | Cl | $OCH(CH_3)CO_2$ | H |
| 642 | F | Cl | $OCH(CH_3)CO_2$ | $CH_3$ |
| 643 | F | Cl | $OCH(CH_3)CO_2$ | $C_2H_5$ |
| 644 | F | Cl | $OCH(CH_3)CO_2$ | Ph |
| 645 | F | Cl | $OCH(CH_3)CO_2$ | $CH_2Ph$ |
| 646 | F | Cl | $OCH(CH_3)CO_2$ | Ph-4-Cl |
| 647 | F | Cl | $OCH(CH_3)CO_2$ | $CH_2Ph$-4-Cl |
| 648 | F | Cl | $OCH(CH_3)CO_2$ | 3-Py |
| 649 | F | Cl | O | H |
| 650 | F | Cl | O | $CH_3$ |
| 651 | F | Cl | O | $C_2H_5$ |
| 652 | F | Cl | O | Ph |
| 653 | F | Cl | O | $CH_2Ph$ |

TABLE 8-continued

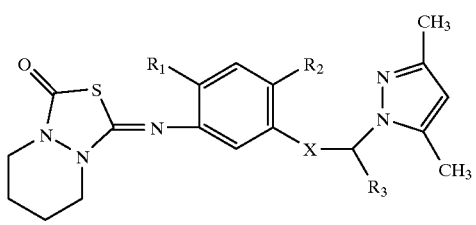

where A = N, B = CH, R$_4$ = R$_5$ = CH$_3$, Q = Q3 in a compound of formula I

| No | R$_1$ | R$_2$ | X | R$_3$ |
|---|---|---|---|---|
| 654 | F | Cl | O | Ph-4-Cl |
| 655 | F | Cl | O | CH$_2$Ph-4-Cl |
| 656 | F | Cl | O | 3-Py |
| 657 | F | Cl | SCH$_2$CO$_2$ | H |
| 658 | F | Cl | SCH$_2$CO$_2$ | CH$_3$ |
| 659 | F | Cl | SCH$_2$CO$_2$ | C$_2$H$_5$ |
| 660 | F | Cl | SCH$_2$CO$_2$ | Ph |
| 661 | F | Cl | SCH$_2$CO$_2$ | CH$_2$Ph |
| 662 | F | Cl | SCH$_2$CO$_2$ | Ph-4-Cl |
| 663 | F | Cl | SCH$_2$CO$_2$ | CH$_2$Ph-4-Cl |
| 664 | F | Cl | SCH$_2$CO$_2$ | 3-Py |
| 665 | F | Cl | SCH(CH$_3$)CO$_2$ | H |
| 666 | F | Cl | SCH(CH$_3$)CO$_2$ | CH$_3$ |
| 667 | F | Cl | SCH(CH$_3$)CO$_2$ | C$_2$H$_5$ |
| 668 | F | Cl | SCH(CH$_3$)CO$_2$ | Ph |
| 669 | F | Cl | SCH(CH$_3$)CO$_2$ | CH$_2$Ph |
| 670 | F | Cl | SCH(CH$_3$)CO$_2$ | Ph-4-Cl |
| 671 | F | Cl | SCH(CH$_3$)CO$_2$ | CH$_2$Ph-4-Cl |
| 672 | F | Cl | SCH(CH$_3$)CO$_2$ | 3-Py |
| 673 | F | Cl | S | H |
| 674 | F | Cl | S | CH$_3$ |
| 675 | F | Cl | S | C$_2$H$_5$ |
| 676 | F | Cl | S | Ph |
| 677 | F | Cl | S | CH$_2$Ph |
| 678 | F | Cl | S | Ph-4-Cl |
| 679 | F | Cl | S | CH$_2$Ph-4-Cl |
| 680 | F | Cl | S | 3-Py |

TABLE 9

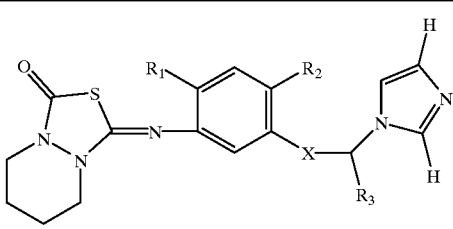

where A = CH, B = N, R$_4$ = R$_5$ = H, Q = Q3 in a compound of formula I

| No | R$_1$ | R$_2$ | X | R$_3$ |
|---|---|---|---|---|
| 681 | F | Cl | CO$_2$ | H |
| 682 | F | Cl | CO$_2$ | CH$_3$ |
| 683 | F | Cl | CO$_2$ | C$_2$H$_5$ |
| 684 | F | Cl | CO$_2$ | Ph |
| 685 | F | Cl | CO$_2$ | CH$_2$Ph |
| 686 | F | Cl | CO$_2$ | Ph-4-Cl |
| 687 | F | Cl | CO$_2$ | CH$_2$Ph-4-Cl |
| 688 | F | Cl | CO$_2$ | 3-Py |
| 689 | F | Cl | OCH$_2$CO$_2$ | H |
| 690 | F | Cl | OCH$_2$CO$_2$ | CH$_3$ |
| 691 | F | Cl | OCH$_2$CO$_2$ | C$_2$H$_5$ |
| 692 | F | Cl | OCH$_2$CO$_2$ | Ph |
| 693 | F | Cl | OCH$_2$CO$_2$ | CH$_2$Ph |
| 694 | F | Cl | OCH$_2$CO$_2$ | Ph-4-Cl |

TABLE 9-continued

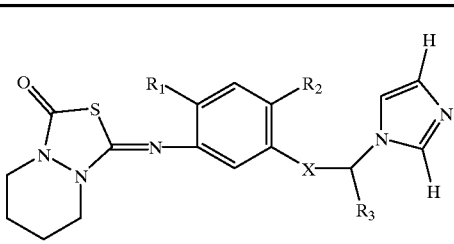

where A = CH, B = N, R$_4$ = R$_5$ = H, Q = Q3 in a compound of formula I

| No | R$_1$ | R$_2$ | X | R$_3$ |
|---|---|---|---|---|
| 695 | F | Cl | OCH$_2$CO$_2$ | CH$_2$Ph-4-Cl |
| 696 | F | Cl | OCH$_2$CO$_2$ | 3-Py |
| 697 | F | Cl | OCH(CH$_3$)CO$_2$ | H |
| 698 | F | Cl | OCH(CH$_3$)CO$_2$ | CH$_3$ |
| 699 | F | Cl | OCH(CH$_3$)CO$_2$ | C$_2$H$_5$ |
| 700 | F | Cl | OCH(CH$_3$)CO$_2$ | Ph |
| 701 | F | Cl | OCH(CH$_3$)CO$_2$ | CH$_2$Ph |
| 702 | F | Cl | OCH(CH$_3$)CO$_2$ | Ph-4-Cl |
| 703 | F | Cl | OCH(CH$_3$)CO$_2$ | CH$_2$Ph-4-Cl |
| 704 | F | Cl | OCH(CH$_3$)CO$_2$ | 3-Py |
| 705 | F | Cl | O | H |
| 706 | F | Cl | O | CH$_3$ |
| 707 | F | Cl | O | C$_2$H$_5$ |
| 708 | F | Cl | O | Ph |
| 709 | F | Cl | O | CH$_2$Ph |
| 710 | F | Cl | O | Ph-4-Cl |
| 711 | F | Cl | O | CH$_2$Ph-4-Cl |
| 712 | F | Cl | O | 3-Py |
| 713 | F | Cl | SCH$_2$CO$_2$ | H |
| 714 | F | Cl | SCH$_2$CO$_2$ | CH$_3$ |
| 715 | F | Cl | SCH$_2$CO$_2$ | C$_2$H$_5$ |
| 716 | F | Cl | SCH$_2$CO$_2$ | Ph |
| 717 | F | Cl | SCH$_2$CO$_2$ | CH$_2$Ph |
| 718 | F | Cl | SCH$_2$CO$_2$ | Ph-4-Cl |
| 719 | F | Cl | SCH$_2$CO$_2$ | CH$_2$Ph-4-Cl |
| 720 | F | Cl | SCH$_2$CO$_2$ | 3-Py |
| 721 | F | Cl | SCH(CH$_3$)CO$_2$ | H |
| 722 | F | Cl | SCH(CH$_3$)CO$_2$ | CH$_3$ |
| 723 | F | Cl | SCH(CH$_3$)CO$_2$ | C$_2$H$_5$ |
| 724 | F | Cl | SCH(CH$_3$)CO$_2$ | Ph |
| 725 | F | Cl | SCH(CH$_3$)CO$_2$ | CH$_2$Ph |
| 726 | F | Cl | SCH(CH$_3$)CO$_2$ | Ph-4-Cl |
| 727 | F | Cl | S | H |
| 728 | F | Cl | S | CH$_3$ |
| 729 | F | Cl | S | C$_2$H$_5$ |
| 730 | F | Cl | S | Ph |
| 731 | F | Cl | S | CH$_2$Ph |
| 732 | F | Cl | S | Ph-4-Cl |
| 733 | F | Cl | S | CH$_2$Ph-4-Cl |
| 734 | F | Cl | S | 3-Py |

TABLE 10

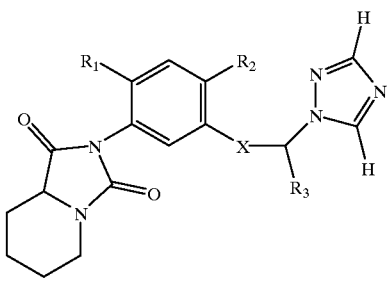

where A = B = N, R₄ = R₅ = H, Q = Q4 in a compound of formula I

| No | R₁ | R₂ | X | R₃ |
|---|---|---|---|---|
| 735 | F | Cl | $CO_2$ | H |
| 736 | F | Cl | $CO_2$ | $CH_3$ |
| 737 | F | Cl | $CO_2$ | $C_2H_5$ |
| 738 | F | Cl | $CO_2$ | Ph |
| 739 | F | Cl | $CO_2$ | $CH_2Ph$ |
| 740 | F | Cl | $CO_2$ | Ph-4-Cl |
| 741 | F | Cl | $CO_2$ | CN |
| 742 | F | Cl | $CO_2$ | 3-Py |
| 743 | F | Cl | $OCH_2CO_2$ | H |
| 744 | F | Cl | $OCH_2CO_2$ | $CH_3$ |
| 745 | F | Cl | $OCH_2CO_2$ | $C_2H_5$ |
| 746 | F | Cl | $OCH_2CO_2$ | Ph |
| 747 | F | Cl | $OCH_2CO_2$ | $CH_2Ph$ |
| 748 | F | Cl | $OCH_2CO_2$ | Ph-4-Cl |
| 749 | F | Cl | $OCH_2CO_2$ | CN |
| 750 | F | Cl | $OCH_2CO_2$ | 3-Py |
| 751 | F | Cl | $OCH(CH_3)CO_2$ | H |
| 752 | F | Cl | $OCH(CH_3)CO_2$ | $CH_3$ |
| 753 | F | Cl | $OCH(CH_3)CO_2$ | $C_2H_5$ |
| 754 | F | Cl | $OCH(CH_3)CO_2$ | Ph |
| 755 | F | Cl | $OCH(CH_3)CO_2$ | $CH_2Ph$ |
| 756 | F | Cl | $OCH(CH_3)CO_2$ | Ph-4-Cl |
| 757 | F | Cl | $OCH(CH_3)CO_2$ | CN |
| 758 | F | Cl | $OCH(CH_3)CO_2$ | 3-Py |
| 759 | F | Cl | O | H |
| 760 | F | Cl | O | $CH_3$ |
| 761 | F | Cl | O | $C_2H_5$ |
| 762 | F | Cl | O | Ph |
| 763 | F | Cl | O | $CH_2Ph$ |
| 764 | F | Cl | O | Ph-4-Cl |
| 765 | F | Cl | O | CN |
| 766 | F | Cl | O | 3-Py |
| 767 | F | Cl | $SCH_2CO_2$ | H |
| 768 | F | Cl | $SCH_2CO_2$ | $CH_3$ |
| 769 | F | Cl | $SCH_2CO_2$ | $C_2H_5$ |
| 770 | F | Cl | $SCH_2CO_2$ | Ph |
| 771 | F | Cl | $SCH_2CO_2$ | $CH_2Ph$ |
| 772 | F | Cl | $SCH_2CO_2$ | Ph-4-Cl |
| 773 | F | Cl | $SCH_2CO_2$ | CN |
| 774 | F | Cl | $SCH_2CO_2$ | 3-Py |
| 775 | F | H | $SCH(CH_3)CO_2$ | H |
| 776 | F | Cl | $SCH(CH_3)CO_2$ | $CH_3$ |
| 777 | F | Cl | $SCH(CH_3)CO_2$ | $C_2H_5$ |
| 778 | F | Cl | $SCH(CH_3)CO_2$ | Ph |
| 779 | F | Cl | $SCH(CH_3)CO_2$ | $CH_2Ph$ |
| 780 | F | Cl | $SCH(CH_3)CO_2$ | Ph-4-Cl |
| 781 | F | Cl | $SCH(CH_3)CO_2$ | $CH_2Ph$-4-Cl |
| 782 | F | Cl | $SCH(CH_3)CO_2$ | 3-Py |
| 783 | F | Cl | S | H |
| 784 | F | Cl | S | $CH_3$ |
| 785 | F | Cl | S | $C_2H_5$ |
| 786 | F | Cl | S | Ph |
| 787 | F | Cl | $CH=C(Cl)CO_2$ | CN |
| 788 | F | Cl | $CH_2CH(Cl)CO_2$ | CN |
| 789 | F | Cl | $CH=C(Cl)CO_2$ | H |
| 790 | F | Cl | $CH_2CH(Cl)CO_2$ | H |
| 791 | Cl | Cl | O | H |
| 792 | Cl | Cl | $OCH_2CO_2$ | H |
| 793 | Cl | Cl | $OCH(CH_3)CO_2$ | H |
| 794 | Cl | Cl | $SCH_2CO_2$ | H |

TABLE 10-continued

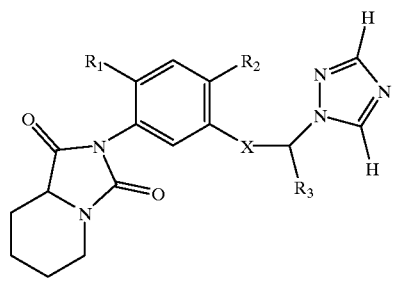

where A = B = N, R₄ = R₅ = H, Q = Q4 in a compound of formula I

| No | R₁ | R₂ | X | R₃ |
|---|---|---|---|---|
| 795 | Cl | Cl | $CH=C(Cl)CO_2$ | H |
| 796 | Cl | Cl | $CH_2CH(Cl)CO_2$ | H |
| 797 | Cl | Cl | $CO_2$ | H |
| 798 | H | Cl | O | H |
| 799 | H | Cl | $OCH_3CO_2$ | H |
| 800 | H | Cl | $OCH(CH_3)CO_2$ | H |
| 801 | H | Cl | $SCH_2CO_2$ | H |
| 802 | H | Cl | $CH=C(Cl)CO_2$ | H |
| 803 | H | Cl | $CH_2CH(Cl)CO_2$ | H |
| 804 | H | Cl | $CO_2$ | H |
| 805 | F | Cl | $OCH_2CO_2$ | Ph-4-F |
| 806 | F | Cl | $SCH_2CO_2$ | Ph-4-F |

TABLE 11

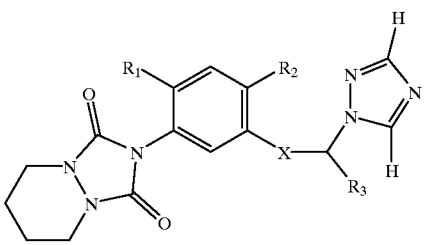

where A = B = N, R₄ = R₅ = H, Q = Q5 in a compound of formula I

| No | R₁ | R₂ | X | R₃ |
|---|---|---|---|---|
| 807 | F | Cl | $CO_2$ | H |
| 808 | F | Cl | $CO_2$ | $CH_3$ |
| 809 | F | Cl | $CO_2$ | $C_2H_5$ |
| 810 | F | Cl | $CO_2$ | Ph |
| 811 | F | Cl | $CO_2$ | $CH_2Ph$ |
| 812 | F | Cl | $CO_2$ | Ph-4-Cl |
| 813 | F | Cl | $CO_2$ | CN |
| 814 | F | Cl | $CO_2$ | 3-Py |
| 815 | F | Cl | $OCH_2CO_2$ | H |
| 816 | F | Cl | $OCH_2CO_2$ | $CH_3$ |
| 817 | F | Cl | $OCH_2CO_2$ | $C_2H_5$ |
| 818 | F | Cl | $OCH_2CO_2$ | Ph |
| 819 | F | Cl | $OCH_2CO_2$ | $CH_2Ph$ |
| 820 | F | Cl | $OCH_2CO_2$ | Ph-4-Cl |
| 821 | F | Cl | $OCH_2CO_2$ | CN |
| 822 | F | Cl | $OCH_2CO_2$ | 3-Py |
| 823 | F | Cl | $OCH(CH_3)CO_2$ | H |
| 824 | F | Cl | $OCH(CH_3)CO_2$ | $CH_3$ |
| 825 | F | Cl | $OCH(CH_3)CO_2$ | $C_2H_5$ |
| 826 | F | Cl | $OCH(CH_3)CO_2$ | Ph |
| 827 | F | Cl | $OCH(CH_3)CO_2$ | $CH_2Ph$ |
| 828 | F | Cl | $OCH(CH_3)CO_2$ | Ph-4-Cl |
| 829 | F | Cl | $OCH(CH_3)CO_2$ | CN |
| 830 | F | Cl | $OCH(CH_3)CO_2$ | 3-Py |
| 831 | F | Cl | O | H |
| 832 | F | Cl | O | $CH_3$ |

TABLE 11-continued

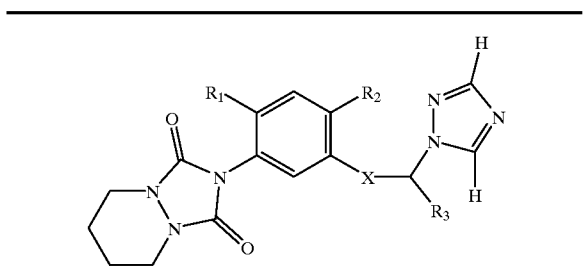

where A = B = N, R₄ = R₅ = H, Q = Q5 in a compound of formula I

| No | R₁ | R₂ | X | R₃ |
|---|---|---|---|---|
| 833 | F | Cl | O | C$_2$H$_5$ |
| 834 | F | Cl | O | Ph |
| 835 | F | Cl | O | CH$_2$Ph |
| 836 | F | Cl | O | Ph-4-Cl |
| 837 | F | Cl | O | CN |
| 838 | F | Cl | O | 3-Py |
| 839 | F | Cl | SCH$_2$CO$_2$ | H |
| 840 | F | Cl | SCH$_2$CO$_2$ | CH$_3$ |
| 841 | F | Cl | SCH$_2$CO$_2$ | C$_2$H$_5$ |
| 842 | F | Cl | SCH$_2$CO$_2$ | Ph |
| 843 | F | Cl | SCH$_2$CO$_2$ | CH$_2$Ph |
| 844 | F | Cl | SCH$_2$CO$_2$ | Ph-4-Cl |
| 845 | F | Cl | SCH$_2$CO$_2$ | CN |
| 846 | F | Cl | SCH$_2$CO$_2$ | 3-Py |
| 847 | F | H | SCH(CH$_3$)CO$_2$ | H |
| 848 | F | Cl | SCH(CH$_3$)CO$_2$ | CH$_3$ |
| 849 | F | Cl | SCH(CH$_3$)CO$_2$ | C$_2$H$_5$ |
| 850 | F | Cl | SCH(CH$_3$)CO$_2$ | Ph |
| 851 | F | Cl | SCH(CH$_3$)CO$_2$ | CH$_2$Ph |
| 852 | F | Cl | SCH(CH$_3$)CO$_2$ | Ph-4-Cl |
| 853 | F | Cl | SCH(CH$_3$)CO$_2$ | CN |
| 854 | F | Cl | SCH(CH$_3$)CO$_2$ | 3-Py |
| 855 | F | Cl | S | H |
| 856 | F | Cl | S | CH$_3$ |
| 857 | F | Cl | S | C$_2$H$_5$ |
| 858 | F | Cl | S | Ph |
| 859 | F | Cl | S | CH$_2$Ph |
| 860 | F | Cl | S | Ph-4-Cl |
| 861 | F | Cl | CH=C(Cl)CO$_2$ | H |
| 862 | F | Cl | CH$_2$CH(Cl)CO$_2$ | H |
| 863 | Cl | Cl | O | H |
| 864 | Cl | Cl | OCH$_2$CO$_2$ | H |
| 865 | Cl | Cl | OCH(CH$_3$)CO$_2$ | H |
| 866 | Cl | Cl | SCH$_2$CO$_2$ | H |
| 867 | Cl | Cl | CH=C(Cl)CO$_2$ | H |
| 868 | Cl | Cl | CH$_2$CH(Cl)CO$_2$ | H |
| 869 | Cl | Cl | CO$_2$ | H |
| 870 | H | Cl | O | H |
| 871 | H | Cl | OCH$_2$CO$_2$ | H |
| 872 | H | Cl | OCH(CH$_3$)CO$_2$ | H |
| 873 | H | Cl | SCH$_2$CO$_2$ | H |
| 874 | H | Cl | CH=C(Cl)CO$_2$ | H |
| 875 | H | Cl | CH$_2$CH(Cl)CO$_2$ | H |
| 876 | H | Cl | CO$_2$ | H |
| 877 | F | Cl | OCH$_2$CO$_2$ | Ph-4-F |
| 878 | F | Cl | SCH$_2$CO$_2$ | Ph-4-F |

TABLE 12

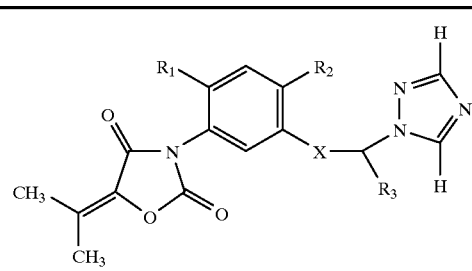

where A = B = N, R₄ = R₅ = H, Q = Q6 in a compound of formula I

| No | R₁ | R₂ | X | R₃ |
|---|---|---|---|---|
| 879 | F | Cl | CO$_2$ | H |
| 880 | F | Cl | CO$_2$ | CH$_3$ |
| 881 | F | Cl | CO$_2$ | C$_2$H$_5$ |
| 882 | F | Cl | CO$_2$ | Ph |
| 883 | F | Cl | CO$_2$ | CH$_2$Ph |
| 884 | F | Cl | CO$_2$ | Ph-4-Cl |
| 885 | F | Cl | CO$_2$ | CN |
| 886 | F | Cl | CO$_2$ | 3-Py |
| 887 | F | Cl | OCH$_2$CO$_2$ | H |
| 888 | F | Cl | OCH$_2$CO$_2$ | CH$_3$ |
| 889 | F | Cl | OCH$_2$CO$_2$ | C$_2$H$_5$ |
| 890 | F | Cl | OCH$_2$CO$_2$ | Ph |
| 891 | F | Cl | OCH$_2$CO$_2$ | CH$_2$Ph |
| 892 | F | Cl | OCH$_2$CO$_2$ | Ph-4-Cl |
| 893 | F | Cl | OCH$_2$CO$_2$ | CN |
| 894 | F | Cl | OCH$_2$CO$_2$ | 3-Py |
| 895 | F | Cl | OCH(CH$_3$)CO$_2$ | H |
| 896 | F | Cl | OCH(CH$_3$)CO$_2$ | CH$_3$ |
| 897 | F | Cl | OCH(CH$_3$)CO$_2$ | C$_2$H$_5$ |
| 898 | F | Cl | OCH(CH$_3$)CO$_2$ | Ph |
| 899 | F | Cl | OCH(CH$_3$)CO$_2$ | CH$_2$Ph |
| 900 | F | Cl | OCH(CH$_3$)CO$_2$ | Ph-4-Cl |
| 901 | F | Cl | OCH(CH$_3$)CO$_2$ | CH$_2$Ph-4-Cl |
| 902 | F | Cl | OCH(CH$_3$)CO$_2$ | 3-Py |
| 903 | F | Cl | O | H |
| 904 | F | Cl | O | CH$_3$ |
| 905 | F | Cl | O | C$_2$H$_5$ |
| 906 | F | Cl | O | Ph |
| 907 | F | Cl | O | CH$_2$Ph |
| 908 | F | Cl | O | Ph-4-Cl |
| 909 | F | Cl | O | CN |
| 910 | F | Cl | O | 3-Py |
| 911 | F | Cl | SCH$_2$CO$_2$ | H |
| 912 | F | Cl | SCH$_2$CO$_2$ | CH$_3$ |
| 913 | F | Cl | SCH$_2$CO$_2$ | C$_2$H$_5$ |
| 914 | F | Cl | SCH$_2$CO$_2$ | Ph |
| 915 | F | Cl | SCH$_2$CO$_2$ | CH$_2$Ph |
| 916 | F | Cl | SCH$_2$CO$_2$ | Ph-4-Cl |
| 917 | F | Cl | SCH$_2$CO$_2$ | CN |
| 918 | F | Cl | SCH$_2$CO$_2$ | 3-Py |
| 919 | F | H | SCH(CH$_3$)CO$_2$ | H |
| 920 | F | Cl | SCH(CH$_3$)CO$_2$ | CH$_3$ |
| 921 | F | Cl | SCH(CH$_3$)CO$_2$ | C$_2$H$_5$ |
| 922 | F | Cl | SCH(CH$_3$)CO$_2$ | Ph |
| 923 | F | Cl | SCH(CH$_3$)CO$_2$ | CH$_2$Ph |
| 924 | F | Cl | SCH(CH$_3$)CO$_2$ | Ph-4-Cl |
| 925 | F | Cl | SCH(CH$_3$)CO$_2$ | CH$_2$Ph-4-Cl |
| 926 | F | Cl | SCH(CH$_3$)CO$_2$ | 3-Py |
| 927 | F | Cl | S | H |
| 928 | F | Cl | S | CH$_3$ |
| 929 | F | Cl | S | C$_2$H$_5$ |
| 930 | F | Cl | S | Ph |
| 931 | F | Cl | S | CH$_2$Ph |
| 932 | F | Cl | S | Ph-4-Cl |
| 933 | F | Cl | CH=C(Cl)CO$_2$ | H |
| 934 | F | Cl | CH$_2$CH(Cl)CO$_2$ | H |
| 935 | Cl | Cl | O | H |
| 936 | Cl | Cl | OCH$_2$CO$_2$ | H |
| 937 | Cl | Cl | CH=C(Cl)CO$_2$ | H |
| 938 | Cl | Cl | CH$_2$CH(Cl)CO$_2$ | H |
| 939 | Cl | Cl | SCH$_2$CO$_2$ | H |

TABLE 12-continued

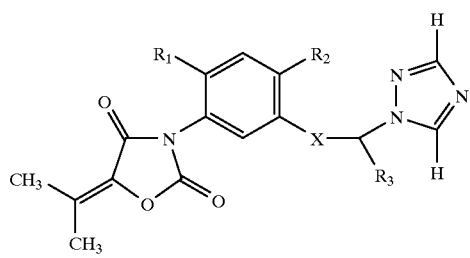

where A = B = N, R₄ = R₅ = H, Q = Q6 in a compound of formula I

| No | R₁ | R₂ | X | R₃ |
|---|---|---|---|---|
| 940 | Cl | Cl | SCH(CH₃)CO₂ | H |
| 941 | Cl | Cl | CO₂ | H |
| 942 | H | Cl | O | H |
| 943 | H | Cl | OCH₂CO₂ | H |
| 944 | H | Cl | OCH(CH₃)CO₂ | H |
| 945 | H | Cl | SCH₂CO₂ | H |
| 946 | H | Cl | CH=C(Cl)CO₂ | H |
| 947 | H | Cl | CH₂CH(Cl)CO₂ | H |
| 948 | H | Cl | CO₂ | H |
| 949 | F | Cl | OCH₂CO₂ | Ph-4-F |
| 950 | F | Cl | SCH₂CO₂ | Ph-4-F |

TABLE 13

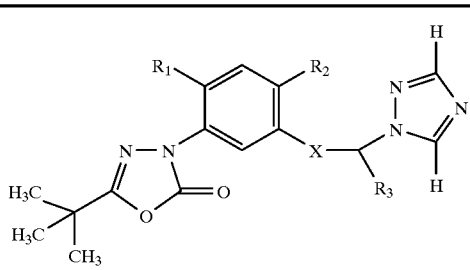

where A = B = N, R₄ = R₅ = H, Q = Q7 in a compound of formula I

| No | R₁ | R₂ | X | R₃ |
|---|---|---|---|---|
| 951 | F | Cl | CO₂ | H |
| 952 | F | Cl | CO₂ | CH₃ |
| 953 | F | Cl | CO₂ | C₂H₅ |
| 954 | F | Cl | CO₂ | Ph |
| 955 | F | Cl | CO₂ | CH₂Ph |
| 956 | F | Cl | CO₂ | Ph-4-Cl |
| 957 | F | Cl | CO₂ | CN |
| 958 | F | Cl | CO₂ | 3-Py |
| 959 | F | Cl | OCH₂CO₂ | H |
| 960 | F | Cl | OCH₂CO₂ | CH₃ |
| 961 | F | Cl | OCH₂CO₂ | C₂H₅ |
| 962 | F | Cl | OCH₂CO₂ | Ph |
| 963 | F | Cl | OCH₂CO₂ | CH₂Ph |
| 964 | F | Cl | OCH₂CO₂ | Ph-4-Cl |
| 965 | F | Cl | OCH₂CO₂ | CN |
| 966 | F | Cl | OCH₂CO₂ | 3-Py |
| 967 | F | Cl | OCH(CH₃)CO₂ | H |
| 968 | F | Cl | OCH(CH₃)CO₂ | CH₃ |
| 969 | F | Cl | OCH(CH₃)CO₂ | C₂H₅ |
| 970 | F | Cl | OCH(CH₃)CO₂ | Ph |
| 971 | F | Cl | OCH(CH₃)CO₂ | CH₂Ph |
| 972 | F | Cl | OCH(CH₃)CO₂ | Ph-4-Cl |
| 973 | F | Cl | OCH(CH₃)CO₂ | CH₂Ph-4-Cl |
| 974 | F | Cl | OCH(CH₃)CO₂ | 3-Py |
| 975 | F | Cl | O | H |
| 976 | F | Cl | O | CH₃ |
| 977 | F | Cl | O | C₂H₅ |
| 978 | F | Cl | O | Ph |

TABLE 13-continued

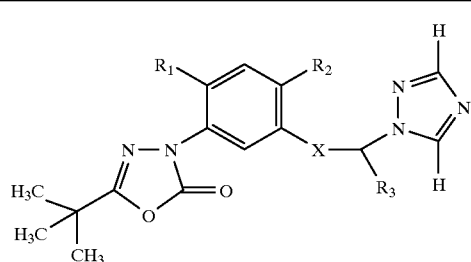

where A = B = N, R₄ = R₅ = H, Q = Q7 in a compound of formula I

| No | R₁ | R₂ | X | R₃ |
|---|---|---|---|---|
| 979 | F | Cl | O | CH₂Ph |
| 980 | F | Cl | O | Ph-4-Cl |
| 981 | F | Cl | O | CN |
| 982 | F | Cl | O | 3-Py |
| 983 | F | Cl | SCH₂CO₂ | H |
| 984 | F | Cl | SCH₂CO₂ | CH₃ |
| 985 | F | Cl | SCH₂CO₂ | C₂H₅ |
| 986 | F | Cl | SCH₂CO₂ | Ph |
| 987 | F | Cl | SCH₂CO₂ | CH₂Ph |
| 988 | F | Cl | SCH₂CO₂ | Ph-4-Cl |
| 989 | F | Cl | SCH₂CO₂ | CN |
| 990 | F | Cl | SCH₂CO₂ | 3-Py |
| 991 | F | H | SCH(CH₃)CO₂ | H |
| 992 | F | Cl | SCH(CH₃)CO₂ | CH₃ |
| 993 | F | Cl | SCH(CH₃)CO₂ | C₂H₅ |
| 994 | F | Cl | SCH(CH₃)CO₂ | Ph |
| 995 | F | Cl | SCH(CH₃)CO₂ | CH₂Ph |
| 996 | F | Cl | SCH(CH₃)CO₂ | Ph-4-Cl |
| 997 | F | Cl | SCH(CH₃)CO₂ | CH₂Ph-4-Cl |
| 998 | F | Cl | SCH(CH₃)CO₂ | 3-Py |
| 999 | F | Cl | S | H |
| 1000 | F | Cl | S | CH₃ |
| 1001 | F | Cl | S | C₂H₅ |
| 1002 | F | Cl | S | Ph |
| 1003 | F | Cl | S | CH₂Ph |
| 1004 | F | Cl | S | Ph-4-Cl |
| 1005 | F | Cl | CH=C(Cl)CO₂ | H |
| 1006 | F | Cl | CH₂CH(Cl)CO₂ | H |
| 1007 | Cl | Cl | O | H |
| 1008 | Cl | Cl | OCH₂CO₂ | H |
| 1009 | Cl | Cl | CH=C(Cl)CO₂ | H |
| 1010 | Cl | Cl | CH₂CH(Cl)CO₂ | H |
| 1011 | Cl | Cl | SCH₂CO₂ | H |
| 1012 | Cl | Cl | SCH(CH₃)CO₂ | H |
| 1013 | Cl | Cl | CO₂ | H |
| 1014 | H | Cl | O | H |
| 1015 | H | Cl | OCH₂CO₂ | H |
| 1016 | H | Cl | OCH(CH₃)CO₂ | H |
| 1017 | H | Cl | SCH₂CO₂ | H |
| 1018 | H | Cl | CH=C(Cl)CO₂ | H |
| 1019 | H | Cl | CH₂CH(Cl)CO₂ | H |
| 1020 | H | Cl | CO₂ | H |
| 1021 | F | Cl | OCH₂CO₂ | Ph-4-F |
| 1022 | F | Cl | SCH₂CO₂ | Ph-4-F |

TABLE 14

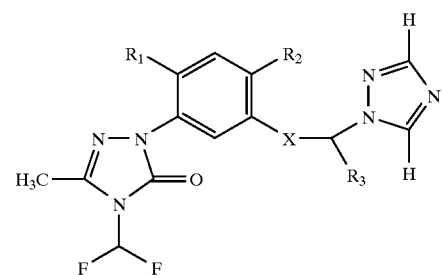

where A = B = N, R₄ = R₅ = H, Q = Q8 in a compound of formula I

| No | R₁ | R₂ | X | R₃ |
|---|---|---|---|---|
| 1023 | F | Cl | CO$_2$ | H |
| 1024 | F | Cl | CO$_2$ | CH$_3$ |
| 1025 | F | Cl | CO$_2$ | C$_2$H$_5$ |
| 1026 | F | Cl | CO$_2$ | Ph |
| 1027 | F | Cl | CO$_2$ | CH$_2$Ph |
| 1028 | F | Cl | CO$_2$ | Ph-4-Cl |
| 1029 | F | Cl | CO$_2$ | CN |
| 1030 | F | Cl | CO$_2$ | 3-Py |
| 1031 | F | Cl | OCH$_2$CO$_2$ | H |
| 1032 | F | Cl | OCH$_2$CO$_2$ | CH$_3$ |
| 1033 | F | Cl | OCH$_2$CO$_2$ | C$_2$H$_5$ |
| 1034 | F | Cl | OCH$_2$CO$_2$ | Ph |
| 1035 | F | Cl | OCH$_2$CO$_2$ | CH$_2$Ph |
| 1036 | F | Cl | OCH$_2$CO$_2$ | Ph-4-Cl |
| 1037 | F | Cl | OCH$_2$CO$_2$ | CN |
| 1038 | F | Cl | OCH$_2$CO$_2$ | 3-Py |
| 1039 | F | Cl | OCH(CH$_3$)CO$_2$ | H |
| 1040 | F | Cl | OCH(CH$_3$)CO$_2$ | CH$_3$ |
| 1041 | F | Cl | OCH(CH$_3$)CO$_2$ | C$_2$H$_5$ |
| 1042 | F | Cl | OCH(CH$_3$)CO$_2$ | Ph |
| 1043 | F | Cl | OCH(CH$_3$)CO$_2$ | CH$_2$Ph |
| 1044 | F | Cl | OCH(CH$_3$)CO$_2$ | Ph-4-Cl |
| 1045 | F | Cl | OCH(CH$_3$)CO$_2$ | CH$_2$Ph-4-Cl |
| 1046 | F | Cl | OCH(CH$_3$)CO$_2$ | 3-Py |
| 1047 | F | Cl | O | H |
| 1048 | F | Cl | O | CH$_3$ |
| 1049 | F | Cl | O | C$_2$H$_5$ |
| 1050 | F | Cl | O | Ph |
| 1051 | F | Cl | O | CH$_2$Ph |
| 1052 | F | Cl | O | Ph-4-Cl |
| 1053 | F | Cl | O | CH$_2$Ph-4-Cl |
| 1054 | F | Cl | O | 3-Py |
| 1055 | F | Cl | SCH$_2$CO$_2$ | H |
| 1056 | F | Cl | SCH$_2$CO$_2$ | CH$_3$ |
| 1057 | F | Cl | SCH$_2$CO$_2$ | C$_2$H$_5$ |
| 1058 | F | Cl | SCH$_2$CO$_2$ | Ph |
| 1059 | F | Cl | SCH$_2$CO$_2$ | CH$_2$Ph |
| 1060 | F | Cl | SCH$_2$CO$_2$ | Ph-4-Cl |
| 1061 | F | Cl | SCH$_2$CO$_2$ | CN |
| 1062 | F | Cl | SCH$_2$CO$_2$ | 3-Py |
| 1063 | F | H | SCH(CH$_3$)CO$_2$ | H |
| 1064 | F | Cl | SCH(CH$_3$)CO$_2$ | CH$_3$ |
| 1065 | F | Cl | SCH(CH$_3$)CO$_2$ | C$_2$H$_5$ |
| 1066 | F | Cl | SCH(CH$_3$)CO$_2$ | Ph |
| 1067 | F | Cl | SCH(CH$_3$)CO$_2$ | CH$_2$Ph |
| 1068 | F | Cl | CH=C(Cl)CO$_2$ | CN |
| 1069 | F | Cl | CH$_2$CH(Cl)CO$_2$ | CN |
| 1070 | F | Cl | SCH(CH$_3$)CO$_2$ | 3-Py |
| 1071 | F | Cl | S | H |
| 1072 | F | Cl | S | CH$_3$ |
| 1073 | F | Cl | S | C$_2$H$_5$ |
| 1074 | F | Cl | S | Ph |
| 1075 | F | Cl | S | CH$_2$Ph |
| 1076 | F | Cl | S | Ph-4-Cl |
| 1077 | F | Cl | CH=C(Cl)CO$_2$ | H |
| 1078 | F | Cl | CH$_2$CH(Cl)CO$_2$ | H |
| 1079 | Cl | Cl | O | H |
| 1080 | Cl | Cl | OCH$_2$CO$_2$ | H |
| 1081 | Cl | Cl | CH=C(Cl)CO$_2$ | H |
| 1082 | Cl | Cl | CH$_2$CH(Cl)CO$_2$ | H |

TABLE 14-continued

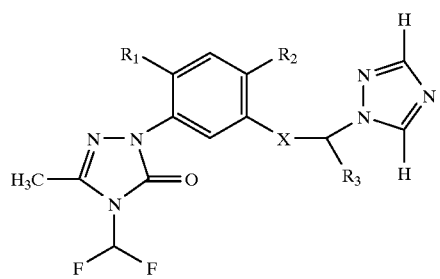

where A = B = N, R₄ = R₅ = H, Q = Q8 in a compound of formula I

| No | R₁ | R₂ | X | R₃ |
|---|---|---|---|---|
| 1083 | Cl | Cl | SCH$_2$CO$_2$ | H |
| 1084 | Cl | Cl | SCH(CH$_3$)CO$_2$ | H |
| 1085 | Cl | Cl | CO$_2$ | H |
| 1086 | H | Cl | O | H |
| 1087 | H | Cl | OCH$_2$CO$_2$ | H |
| 1088 | H | Cl | OCH(CH$_3$)CO$_2$ | H |
| 1089 | H | Cl | SCH$_2$CO$_2$ | H |
| 1090 | H | Cl | CH=C(Cl)CO$_2$ | H |
| 1091 | H | Cl | CH$_2$CH(Cl)CO$_2$ | H |
| 1092 | H | Cl | CO$_2$ | H |
| 1093 | F | Cl | OCH$_2$CO$_2$ | Ph-4-F |
| 1094 | F | Cl | SCH$_2$CO$_2$ | Ph-4-F |

TABLE 15

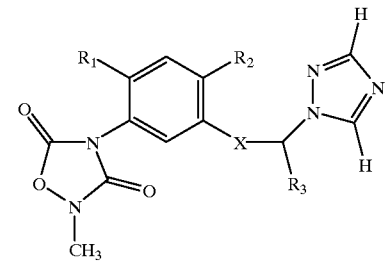

where A = B = N, R₄ = R₅ = H, Q = Q9 in a compound of formula I

| No | R₁ | R₂ | X | R₃ |
|---|---|---|---|---|
| 1095 | F | Cl | CO$_2$ | H |
| 1096 | F | Cl | CO$_2$ | CH$_3$ |
| 1097 | F | Cl | CO$_2$ | C$_2$H$_5$ |
| 1098 | F | Cl | CO$_2$ | Ph |
| 1099 | F | Cl | CO$_2$ | CH$_2$Ph |
| 1100 | F | Cl | CO$_2$ | Ph-4-Cl |
| 1101 | F | Cl | CO$_2$ | CN |
| 1102 | F | Cl | CO$_2$ | 3-Py |
| 1103 | F | Cl | OCH$_2$CO$_2$ | H |
| 1104 | F | Cl | OCH$_2$CO$_2$ | CH$_3$ |
| 1105 | F | Cl | OCH$_2$CO$_2$ | C$_2$H$_5$ |
| 1106 | F | Cl | OCH$_2$CO$_2$ | Ph |
| 1107 | F | Cl | OCH$_2$CO$_2$ | CH$_2$Ph |
| 1108 | F | Cl | OCH$_2$CO$_2$ | Ph-4-Cl |
| 1109 | F | Cl | OCH$_2$CO$_2$ | CN |
| 1110 | F | Cl | OCH$_2$CO$_2$ | 3-Py |
| 1111 | F | Cl | OCH(CH$_3$)CO$_2$ | H |
| 1112 | F | Cl | OCH(CH$_3$)CO$_2$ | CH$_3$ |
| 1113 | F | Cl | OCH(CH$_3$)CO$_2$ | C$_2$H$_5$ |
| 1114 | F | Cl | OCH(CH$_3$)CO$_2$ | Ph |
| 1115 | F | Cl | OCH(CH$_3$)CO$_2$ | CH$_2$Ph |
| 1116 | F | Cl | OCH(CH$_3$)CO$_2$ | Ph-4-Cl |
| 1117 | F | Cl | OCH(CH$_3$)CO$_2$ | CN |
| 1118 | F | Cl | OCH(CH$_3$)CO$_2$ | 3-Py |
| 1119 | F | Cl | O | H |
| 1120 | F | Cl | O | CH$_3$ |

TABLE 15-continued where A = B = N, R$_4$ = R$_5$ = H, Q = Q9 in a compound of formula I

| No | R$_1$ | R$_2$ | X | R$_3$ |
|---|---|---|---|---|
| 1121 | F | Cl | O | C$_2$H$_5$ |
| 1122 | F | Cl | O | Ph |
| 1123 | F | Cl | O | CH$_2$Ph |
| 1124 | F | Cl | O | Ph-4-Cl |
| 1125 | F | Cl | O | CN |
| 1126 | F | Cl | O | 3-Py |
| 1127 | F | Cl | SCH$_2$CO$_2$ | H |
| 1128 | F | Cl | SCH$_2$CO$_2$ | CH$_3$ |
| 1129 | F | Cl | SCH$_2$CO$_2$ | C$_2$H$_5$ |
| 1130 | F | Cl | SCH$_2$CO$_2$ | Ph |
| 1131 | F | Cl | SCH$_2$CO$_2$ | CH$_2$Ph |
| 1132 | F | Cl | SCH$_2$CO$_2$ | Ph-4-Cl |
| 1133 | F | Cl | SCH$_2$CO$_2$ | CN |
| 1134 | F | Cl | SCH$_2$CO$_2$ | 3-Py |
| 1135 | F | H | SCH(CH$_3$)CO$_2$ | H |
| 1136 | F | Cl | SCH(CH$_3$)CO$_2$ | CH$_3$ |
| 1137 | F | Cl | SCH(CH$_3$)CO$_2$ | C$_2$H$_5$ |
| 1138 | F | Cl | SCH(CH$_3$)CO$_2$ | Ph |
| 1139 | F | Cl | SCH(CH$_3$)CO$_2$ | CH$_2$Ph |
| 1140 | F | Cl | SCH(CH$_3$)CO$_2$ | Ph-4-Cl |
| 1141 | F | Cl | SCH(CH$_3$)CO$_2$ | CH$_2$Ph-4-Cl |
| 1142 | F | Cl | SCH(CH$_3$)CO$_2$ | 3-Py |
| 1143 | F | Cl | S | H |
| 1144 | F | Cl | S | CH$_3$ |
| 1145 | F | Cl | S | C$_2$H$_5$ |
| 1146 | F | Cl | S | Ph |
| 1147 | F | Cl | S | CH$_2$Ph |
| 1148 | F | Cl | S | Ph-4-Cl |
| 1149 | F | Cl | CH=C(Cl)CO$_2$ | H |
| 1150 | F | Cl | CH$_2$CH(Cl)CO$_2$ | H |
| 1151 | Cl | Cl | O | H |
| 1152 | Cl | Cl | OCH$_2$CO$_2$ | H |
| 1153 | Cl | Cl | CH=C(Cl)CO$_2$ | H |
| 1154 | Cl | Cl | CH$_2$CH(Cl)CO$_2$ | H |
| 1155 | Cl | Cl | SCH$_2$CO$_2$ | H |
| 1156 | Cl | Cl | SCH(CH$_3$)CO$_2$ | H |
| 1157 | Cl | Cl | CO$_2$ | H |
| 1158 | H | Cl | O | H |
| 1159 | H | Cl | OCH$_2$CO$_2$ | H |
| 1160 | H | Cl | OCH(CH$_3$)CO$_2$ | H |
| 1161 | H | Cl | SCH$_2$CO$_2$ | H |
| 1162 | H | Cl | CH=C(Cl)CO$_2$ | H |
| 1163 | H | Cl | CH$_2$CH(Cl)CO$_2$ | H |
| 1164 | H | Cl | CO$_2$ | H |
| 1165 | F | Cl | OCH$_2$CO$_2$ | Ph-4-F |
| 1166 | F | Cl | SCH$_2$CO$_2$ | Ph-4-F |

TABLE 16

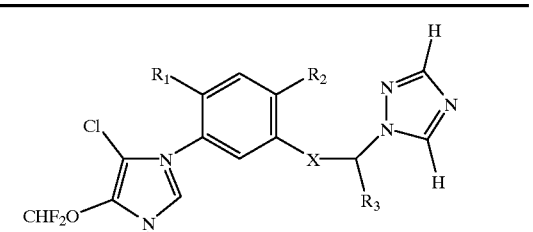

where A = B = N, R$_4$ = R$_5$ = H, Q = Q10 in a compound of formula I

| No | R$_1$ | R$_2$ | X | R$_3$ |
|---|---|---|---|---|
| 1167 | F | Cl | CO$_2$ | H |
| 1168 | F | Cl | CO$_2$ | CH$_3$ |
| 1169 | F | Cl | CO$_2$ | C$_2$H$_5$ |
| 1170 | F | Cl | CO$_2$ | Ph |
| 1171 | F | Cl | CO$_2$ | CH$_2$Ph |
| 1172 | F | Cl | CO$_2$ | Ph-4-Cl |
| 1173 | F | Cl | CO$_2$ | CH$_2$Ph-4-Cl |
| 1174 | F | Cl | CO$_2$ | 3-Py |
| 1175 | F | Cl | OCH$_2$CO$_2$ | H |
| 1176 | F | Cl | OCH$_2$CO$_2$ | CH$_3$ |
| 1177 | F | Cl | OCH$_2$CO$_2$ | C$_2$H$_5$ |
| 1178 | F | Cl | OCH$_2$CO$_2$ | Ph |
| 1179 | F | Cl | OCH$_2$CO$_2$ | CH$_2$Ph |
| 1180 | F | Cl | OCH$_2$CO$_2$ | Ph-4-Cl |
| 1181 | F | Cl | OCH$_2$CO$_2$ | CH$_2$Ph-4-Cl |
| 1182 | F | Cl | OCH$_2$CO$_2$ | 3-Py |
| 1183 | F | Cl | OCH(CH$_3$)CO$_2$ | H |
| 1184 | F | Cl | OCH(CH$_3$)CO$_2$ | CH$_3$ |
| 1185 | F | Cl | OCH(CH$_3$)CO$_2$ | C$_2$H$_5$ |
| 1186 | F | Cl | OCH(CH$_3$)CO$_2$ | Ph |
| 1187 | F | Cl | OCH(CH$_3$)CO$_2$ | CH$_2$Ph |
| 1188 | F | Cl | OCH(CH$_3$)CO$_2$ | Ph-4-Cl |
| 1189 | F | Cl | OCH(CH$_3$)CO$_2$ | CH$_2$Ph-4-Cl |
| 1190 | F | Cl | OCH(CH$_3$)CO$_2$ | 3-Py |
| 1191 | F | Cl | O | H |
| 1192 | F | Cl | O | CH$_3$ |
| 1193 | F | Cl | O | C$_2$H$_5$ |
| 1194 | F | Cl | O | Ph |
| 1195 | F | Cl | O | CH$_2$Ph |
| 1196 | F | Cl | O | Ph-4-Cl |
| 1197 | F | Cl | O | CH$_2$Ph-4-Cl |
| 1198 | F | Cl | O | 3-Py |
| 1199 | F | Cl | SCH$_2$CO$_2$ | H |
| 1200 | F | Cl | SCH$_2$CO$_2$ | CH$_3$ |
| 1201 | F | Cl | SCH$_2$CO$_2$ | C$_2$H$_5$ |
| 1202 | F | Cl | SCH$_2$CO$_2$ | Ph |
| 1203 | F | Cl | SCH$_2$CO$_2$ | CH$_2$Ph |
| 1204 | F | Cl | SCH$_2$CO$_2$ | Ph-4-Cl |
| 1205 | F | Cl | SCH$_2$CO$_2$ | CH$_2$Ph-4-Cl |
| 1206 | F | Cl | SCH$_2$CO$_2$ | 3-Py |
| 1207 | F | H | SCH(CH$_3$)CO$_2$ | H |
| 1208 | F | Cl | SCH(CH$_3$)CO$_2$ | CH$_3$ |
| 1209 | F | Cl | SCH(CH$_3$)CO$_2$ | C$_2$H$_5$ |
| 1210 | F | Cl | SCH(CH$_3$)CO$_2$ | Ph |
| 1211 | F | Cl | SCH(CH$_3$)CO$_2$ | CH$_2$Ph |
| 1212 | F | Cl | SCH(CH$_3$)CO$_2$ | Ph-4-Cl |
| 1213 | F | Cl | SCH(CH$_3$)CO$_2$ | CH$_2$Ph-4-Cl |
| 1214 | F | Cl | SCH(CH$_3$)CO$_2$ | 3-Py |
| 1215 | F | Cl | S | H |
| 1216 | F | Cl | S | CH$_3$ |
| 1217 | F | Cl | S | C$_2$H$_5$ |
| 1218 | F | Cl | S | Ph |
| 1219 | F | Cl | S | CH$_2$Ph |
| 1220 | F | Cl | S | Ph-4-Cl |
| 1221 | F | Cl | CH=C(Cl)CO$_2$ | H |
| 1222 | F | Cl | CH$_2$CH(Cl)CO$_2$ | H |
| 1223 | Cl | Cl | O | H |
| 1224 | Cl | Cl | OCH$_2$CO$_2$ | H |
| 1225 | Cl | Cl | CH=C(Cl)CO$_2$ | H |
| 1226 | Cl | Cl | CH$_2$CH(Cl)CO$_2$ | H |
| 1227 | Cl | Cl | SCH$_2$CO$_2$ | H |

TABLE 16-continued

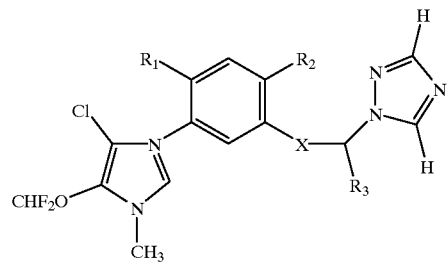

where A = B = N, R_4 = R_5 = H, Q = Q10 in a compound of formula I

| No | $R_1$ | $R_2$ | X | $R_3$ |
|---|---|---|---|---|
| 1228 | Cl | Cl | SCH(CH$_3$)CO$_2$ | H |
| 1229 | Cl | Cl | CO$_2$ | H |
| 1230 | H | Cl | O | H |
| 1231 | H | Cl | OCH$_2$CO$_2$ | H |
| 1232 | H | Cl | OCH(CH$_3$)CO$_2$ | H |
| 1233 | H | Cl | SCH$_2$CO$_2$ | H |
| 1234 | H | Cl | CH=C(Cl)CO$_2$ | H |
| 1235 | H | Cl | CH$_2$CH(Cl)CO$_2$ | H |
| 1236 | H | Cl | CO$_2$ | H |
| 1237 | F | Cl | OCH$_2$CO$_2$ | Ph-4-F |
| 1238 | F | Cl | SCH$_2$CO$_2$ | Ph-4-F |

TABLE 17

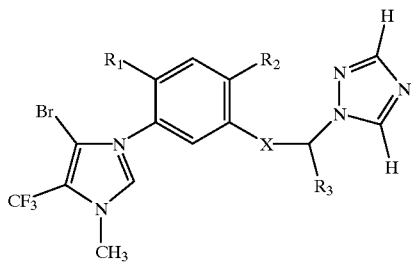

where A = B = N, R_4 = R_5 = H, Q = Q11 in a compound of formula I

| No | $R_1$ | $R_2$ | X | $R_3$ |
|---|---|---|---|---|
| 1239 | F | Cl | CO$_2$ | H |
| 1240 | F | Cl | CO$_2$ | CH$_3$ |
| 1241 | F | Cl | CO$_2$ | C$_2$H$_5$ |
| 1242 | F | Cl | CO$_2$ | Ph |
| 1243 | F | Cl | CO$_2$ | CH$_2$Ph |
| 1244 | F | Cl | CO$_2$ | Ph-4-Cl |
| 1245 | F | Cl | CO$_2$ | CH$_2$Ph-4-Cl |
| 1246 | F | Cl | CO$_2$ | 3-Py |
| 1247 | F | Cl | OCH$_2$CO$_2$ | H |
| 1248 | F | Cl | OCH$_2$CO$_2$ | CH$_3$ |
| 1249 | F | Cl | OCH$_2$CO$_2$ | C$_2$H$_5$ |
| 1250 | F | Cl | OCH$_2$CO$_2$ | Ph |
| 1251 | F | Cl | OCH$_2$CO$_2$ | CH$_2$Ph |
| 1252 | F | Cl | OCH$_2$CO$_2$ | Ph-4-Cl |
| 1253 | F | Cl | OCH$_2$CO$_2$ | CH$_2$Ph-4-Cl |
| 1254 | F | Cl | OCH$_2$CO$_2$ | 3-Py |
| 1255 | F | Cl | OCH(CH$_3$)CO$_2$ | H |
| 1256 | F | Cl | OCH(CH$_3$)CO$_2$ | CH$_3$ |
| 1257 | F | Cl | OCH(CH$_3$)CO$_2$ | C$_2$H$_5$ |
| 1258 | F | Cl | OCH(CH$_3$)CO$_2$ | Ph |
| 1259 | F | Cl | OCH(CH$_3$)CO$_2$ | CH$_2$Ph |
| 1260 | F | Cl | OCH(CH$_3$)CO$_2$ | Ph-4-Cl |
| 1261 | F | Cl | OCH(CH$_3$)CO$_2$ | CH$_2$Ph-4-Cl |
| 1262 | F | Cl | OCH(CH$_3$)CO$_2$ | 3-Py |
| 1263 | F | Cl | O | H |
| 1264 | F | Cl | O | CH$_3$ |
| 1265 | F | Cl | O | C$_2$H$_5$ |

TABLE 17-continued

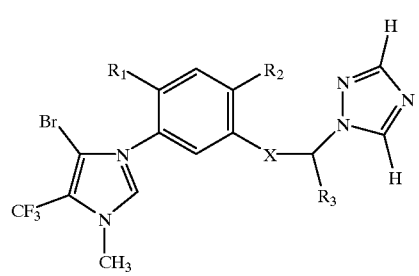

where A = B = N, R_4 = R_5 = H, Q = Q11 in a compound of formula I

| No | $R_1$ | $R_2$ | X | $R_3$ |
|---|---|---|---|---|
| 1266 | F | Cl | O | Ph |
| 1267 | F | Cl | O | CH$_2$Ph |
| 1268 | F | Cl | O | Ph-4-Cl |
| 1269 | F | Cl | O | CH$_2$Ph-4-Cl |
| 1270 | F | Cl | O | 3-Py |
| 1271 | F | Cl | SCH$_2$CO$_2$ | H |
| 1272 | F | Cl | SCH$_2$CO$_2$ | CH$_3$ |
| 1273 | F | Cl | SCH$_2$CO$_2$ | C$_2$H$_5$ |
| 1274 | F | Cl | SCH$_2$CO$_2$ | Ph |
| 1275 | F | Cl | SCH$_2$CO$_2$ | CH$_2$Ph |
| 1276 | F | Cl | SCH$_2$CO$_2$ | Ph-4-Cl |
| 1277 | F | Cl | SCH$_2$CO$_2$ | CH$_2$Ph-4-Cl |
| 1278 | F | Cl | SCH$_2$CO$_2$ | 3-Py |
| 1279 | F | H | SCH(CH$_3$)CO$_2$ | H |
| 1280 | F | Cl | SCH(CH$_3$)CO$_2$ | CH$_3$ |
| 1281 | F | Cl | SCH(CH$_3$)CO$_2$ | C$_2$H$_5$ |
| 1282 | F | Cl | SCH(CH$_3$)CO$_2$ | Ph |
| 1283 | F | Cl | SCH(CH$_3$)CO$_2$ | CH$_2$Ph |
| 1284 | F | Cl | SCH(CH$_3$)CO$_2$ | Ph-4-Cl |
| 1285 | F | Cl | SCH(CH$_3$)CO$_2$ | CH$_2$Ph-4-Cl |
| 1286 | F | Cl | SCH(CH$_3$)CO$_2$ | 3-Py |
| 1287 | F | Cl | S | H |
| 1288 | F | Cl | S | CH$_3$ |
| 1289 | F | Cl | S | C$_2$H$_5$ |
| 1290 | F | Cl | S | Ph |
| 1291 | F | Cl | S | CH$_2$Ph |
| 1292 | F | Cl | S | Ph-4-Cl |
| 1293 | F | Cl | CH=C(Cl)CO$_2$ | H |
| 1294 | F | Cl | CH$_2$CH(Cl)CO$_2$ | H |
| 1295 | Cl | Cl | O | H |
| 1296 | Cl | Cl | OCH$_2$CO$_2$ | H |
| 1297 | Cl | Cl | CH=C(Cl)CO$_2$ | H |
| 1298 | Cl | Cl | CH$_2$CH(Cl)CO$_2$ | H |
| 1299 | Cl | Cl | SCH$_2$CO$_2$ | H |
| 1300 | Cl | Cl | SCH(CH$_3$)CO$_2$ | H |
| 1301 | Cl | Cl | CO$_2$ | H |
| 1302 | H | Cl | O | H |
| 1303 | H | Cl | OCH$_2$CO$_2$ | H |
| 1304 | H | Cl | OCH(CH$_3$)CO$_2$ | H |
| 1305 | H | Cl | SCH$_2$CO$_2$ | H |
| 1306 | H | Cl | CH=C(Cl)CO$_2$ | H |
| 1307 | H | Cl | CH$_2$CH(Cl)CO$_2$ | H |
| 1308 | H | Cl | CO$_2$ | H |
| 1309 | F | Cl | OCH$_2$CO$_2$ | Ph-4-F |
| 1310 | F | Cl | SCH$_2$CO$_2$ | Ph-4-F |

TABLE 18

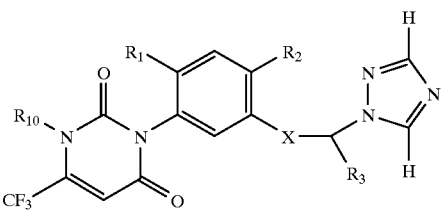

where A = B = N, R$_4$ = R$_5$ = H, Q = Q12 in a compound of formula I

| No | R$_1$ | R$_2$ | X | R$_3$ | R$_{10}$ |
|---|---|---|---|---|---|
| 1311 | F | Cl | CO$_2$ | H | CH$_3$ |
| 1312 | F | Cl | CO$_2$ | CH$_3$ | CH$_3$ |
| 1313 | F | Cl | CO$_2$ | C$_2$H$_5$ | CH$_3$ |
| 1314 | F | Cl | CO$_2$ | H | NH$_2$ |
| 1315 | F | Cl | CO$_2$ | CH$_3$ | NH$_2$ |
| 1316 | F | Cl | CO$_2$ | C$_2$H$_5$ | NH$_2$ |
| 1317 | F | Cl | CO$_2$ | CN | NH$_2$ |
| 1318 | F | Cl | CO$_2$ | CN | CH$_3$ |
| 1319 | F | Cl | OCH$_2$CO$_2$ | H | CH$_3$ |
| 1320 | F | Cl | OCH$_2$CO$_2$ | CH$_3$ | CH$_3$ |
| 1321 | F | Cl | OCH$_2$CO$_2$ | C$_2$H$_5$ | CH$_3$ |
| 1322 | F | Cl | OCH$_2$CO$_2$ | H | NH$_2$ |
| 1323 | F | Cl | OCH$_2$CO$_2$ | CH$_3$ | NH$_2$ |
| 1324 | F | Cl | OCH$_2$CO$_2$ | C$_2$H$_5$ | NH$_2$ |
| 1325 | F | Cl | OCH$_2$CO$_2$ | CN | NH$_2$ |
| 1326 | F | Cl | OCH$_2$CO$_2$ | CN | CH$_3$ |
| 1327 | F | Cl | OCH(CH$_3$)CO$_2$ | H | CH$_3$ |
| 1328 | F | Cl | OCH(CH$_3$)CO$_2$ | CH$_3$ | CH$_3$ |
| 1329 | F | Cl | OCH(CH$_3$)CO$_2$ | C$_2$H$_5$ | CH$_3$ |
| 1330 | F | Cl | OCH(CH$_3$)CO$_2$ | H | NH$_2$ |
| 1331 | F | Cl | OCH(CH$_3$)CO$_2$ | CH$_3$ | NH$_2$ |
| 1332 | F | Cl | OCH(CH$_3$)CO$_2$ | C$_2$H$_5$ | NH$_2$ |
| 1333 | F | Cl | OCH(CH$_3$)CO$_2$ | CN | NH$_2$ |
| 1334 | F | Cl | O | H | H |
| 1335 | F | Cl | O | H | CH$_3$ |
| 1336 | F | Cl | O | CH$_3$ | CH$_3$ |
| 1337 | F | Cl | O | C$_2$H$_5$ | CH$_3$ |
| 1338 | F | Cl | O | H | NH$_2$ |
| 1339 | F | Cl | O | CH$_3$ | NH$_2$ |
| 1340 | F | Cl | O | C$_2$H$_5$ | NH$_2$ |
| 1341 | F | Cl | O | CN | NH$_2$ |
| 1342 | F | Cl | O | CN | CH$_3$ |
| 1343 | F | Cl | SCH$_2$CO$_2$ | H | CH$_3$ |
| 1344 | F | Cl | SCH$_2$CO$_2$ | CH$_3$ | CH$_3$ |
| 1345 | F | Cl | SCH$_2$CO$_2$ | C$_2$H$_5$ | CH$_3$ |
| 1346 | F | Cl | SCH$_2$CO$_2$ | H | NH$_2$ |
| 1347 | F | Cl | SCH$_2$CO$_2$ | CH$_3$ | NH$_2$ |
| 1348 | F | Cl | SCH$_2$CO$_2$ | C$_2$H$_5$ | NH$_2$ |
| 1349 | F | Cl | SCH$_2$CO$_2$ | CN | NH$_2$ |
| 1350 | F | Cl | SCH$_2$CO$_2$ | CN | CH$_3$ |
| 1351 | F | H | SCH(CH$_3$)CO$_2$ | H | CH$_3$ |
| 1352 | F | Cl | SCH(CH$_3$)CO$_2$ | CH$_3$ | CH$_3$ |
| 1353 | F | Cl | SCH(CH$_3$)CO$_2$ | C$_2$H$_5$ | CH$_3$ |
| 1354 | F | Cl | SCH(CH$_3$)CO$_2$ | H | NH$_2$ |
| 1355 | F | Cl | SCH(CH$_3$)CO$_2$ | CH$_3$ | NH$_2$ |
| 1356 | F | Cl | SCH(CH$_3$)CO$_2$ | C$_2$H$_5$ | NH$_2$ |
| 1357 | F | Cl | CH=C(Cl)CO$_2$ | H | NH$_2$ |
| 1358 | F | Cl | CH$_2$CH(Cl)CO$_2$ | H | NH$_2$ |
| 1359 | F | Cl | CH=C(Cl)CO$_2$ | CN | NH$_2$ |
| 1360 | F | Cl | CH$_2$CH(Cl)CO$_2$ | CN | NH$_2$ |
| 1361 | F | Cl | S | H | CH$_3$ |
| 1362 | F | Cl | S | H | NH$_2$ |
| 1363 | F | Cl | CH=C(Cl)CO$_2$ | H | CH$_3$ |
| 1364 | F | Cl | CH$_2$CH(Cl)CO$_2$ | H | CH$_3$ |
| 1365 | F | Cl | CH=C(Cl)CO$_2$ | CN | CH$_3$ |
| 1366 | F | Cl | CH$_2$CH(Cl)CO$_2$ | CN | CH$_3$ |
| 1367 | Cl | Cl | O | H | NH$_2$ |
| 1368 | Cl | Cl | OCH$_2$CO$_2$ | H | CH$_3$ |
| 1369 | Cl | Cl | OCH(CH$_3$)CO$_2$ | H | CH$_3$ |
| 1370 | Cl | Cl | SCH$_2$CO$_2$ | H | CH$_3$ |
| 1371 | Cl | Cl | CH=C(Cl)CO$_2$ | H | CH$_3$ |
| 1372 | Cl | Cl | CH$_2$CH(Cl)CO$_2$ | H | CH$_3$ |
| 1373 | Cl | Cl | CO$_2$ | H | CH$_3$ |
| 1374 | H | Cl | O | H | CH$_3$ |
| 1375 | H | Cl | OCH$_2$CO$_2$ | H | CH$_3$ |
| 1376 | H | Cl | OCH(CH$_3$)CO$_2$ | H | CH$_3$ |
| 1377 | H | Cl | SCH$_2$CO$_2$ | H | CH$_3$ |
| 1378 | H | Cl | CH=C(Cl)CO$_2$ | H | NH$_2$ |
| 1379 | H | Cl | CH$_2$CH(Cl)CO$_2$ | H | NH$_2$ |
| 1380 | H | Cl | CO$_2$ | H | NH$_2$ |
| 1381 | H | Cl | OCH$_2$CO$_2$ | H | NH$_2$ |
| 1382 | H | Cl | SCH$_2$CO$_2$ | H | NH$_2$ |

TABLE 19

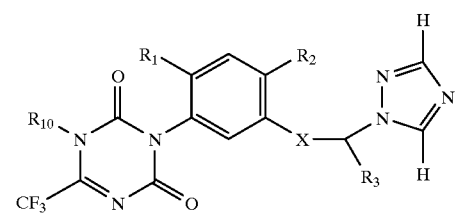

where A = B = N, R$_4$ = R$_5$ = H, Q = Q13 in a compound of formula I

| No | R$_1$ | R$_2$ | X | R$_3$ | R$_{10}$ |
|---|---|---|---|---|---|
| 1383 | F | Cl | CO$_2$ | H | CH$_3$ |
| 1384 | F | Cl | CO$_2$ | CH$_3$ | CH$_3$ |
| 1385 | F | Cl | CO$_2$ | C$_2$H$_5$ | CH$_3$ |
| 1386 | F | Cl | CO$_2$ | H | NH$_2$ |
| 1387 | F | Cl | CO$_2$ | CH$_3$ | NH$_2$ |
| 1388 | F | Cl | CO$_2$ | C$_2$H$_5$ | NH$_2$ |
| 1389 | F | Cl | CO$_2$ | CN | NH$_2$ |
| 1390 | F | Cl | CO$_2$ | CN | CH$_3$ |
| 1391 | F | Cl | OCH$_2$CO$_2$ | H | CH$_3$ |
| 1392 | F | Cl | OCH$_2$CO$_2$ | CH$_3$ | CH$_3$ |
| 1393 | F | Cl | OCH$_2$CO$_2$ | C$_2$H$_5$ | CH$_3$ |
| 1394 | F | Cl | OCH$_2$CO$_2$ | H | NH$_2$ |
| 1395 | F | Cl | OCH$_2$CO$_2$ | CH$_3$ | NH$_2$ |
| 1396 | F | Cl | OCH$_2$CO$_2$ | C$_2$H$_5$ | NH$_2$ |
| 1397 | F | Cl | OCH$_2$CO$_2$ | CN | NH$_2$ |
| 1398 | F | Cl | OCH$_2$CO$_2$ | CN | CH$_3$ |
| 1399 | F | Cl | OCH(CH$_3$)CO$_2$ | H | CH$_3$ |
| 1400 | F | Cl | OCH(CH$_3$)CO$_2$ | CH$_3$ | CH$_3$ |
| 1401 | F | Cl | OCH(CH$_3$)CO$_2$ | C$_2$H$_5$ | CH$_3$ |
| 1402 | F | Cl | OCH(CH$_3$)CO$_2$ | H | NH$_2$ |
| 1403 | F | Cl | OCH(CH$_3$)CO$_2$ | CH$_3$ | NH$_2$ |
| 1404 | F | Cl | OCH(CH$_3$)CO$_2$ | C$_2$H$_5$ | NH$_2$ |
| 1405 | F | Cl | OCH(CH$_3$)CO$_2$ | CN | NH$_2$ |
| 1406 | F | Cl | OCH(CH$_3$)CO$_2$ | CN | CH$_3$ |
| 1407 | F | Cl | O | H | CH$_3$ |
| 1408 | F | Cl | O | CH$_3$ | CH$_3$ |
| 1409 | F | Cl | O | C$_2$H$_5$ | CH$_3$ |
| 1410 | F | Cl | O | H | NH$_2$ |
| 1411 | F | Cl | O | CH$_3$ | NH$_2$ |
| 1412 | F | Cl | O | C$_2$H$_5$ | NH$_2$ |
| 1413 | F | Cl | O | CN | NH$_2$ |
| 1414 | F | Cl | O | CN | CH$_3$ |
| 1415 | F | Cl | SCH$_2$CO$_2$ | H | CH$_3$ |
| 1416 | F | Cl | SCH$_2$CO$_2$ | CH$_3$ | CH$_3$ |

TABLE 19-continued

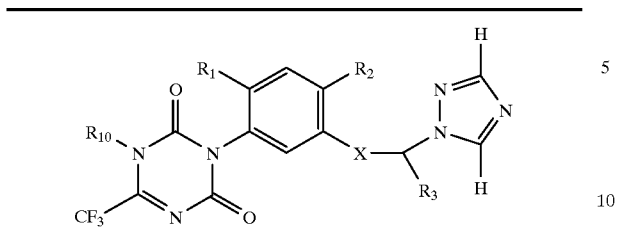

where A = B = N, $R_4 = R_5$ = H, Q = Q13 in a compound of formula I

| No | $R_1$ | $R_2$ | X | $R_3$ | $R_{10}$ |
|---|---|---|---|---|---|
| 1417 | F | Cl | $SCH_2CO_2$ | $C_2H_5$ | $CH_3$ |
| 1418 | F | Cl | $SCH_2CO_2$ | H | $NH_2$ |
| 1419 | F | Cl | $SCH_2CO_2$ | $CH_3$ | $NH_2$ |
| 1420 | F | Cl | $SCH_2CO_2$ | $C_2H_5$ | $NH_2$ |
| 1421 | F | Cl | $SCH_2CO_2$ | CN | $NH_2$ |
| 1422 | F | Cl | $SCH_2CO_2$ | CN | $CH_3$ |
| 1423 | F | H | $SCH(CH_3)CO_2$ | H | $CH_3$ |
| 1424 | F | Cl | $SCH(CH_3)CO_2$ | $CH_3$ | $CH_3$ |
| 1425 | F | Cl | $SCH(CH_3)CO_2$ | $C_2H_5$ | $CH_3$ |
| 1426 | F | Cl | $SCH(CH_3)CO_2$ | H | $NH_2$ |
| 1427 | F | Cl | $SCH(CH_3)CO_2$ | $CH_3$ | $NH_2$ |
| 1428 | F | Cl | $SCH(CH_3)CO_2$ | $C_2H_5$ | $NH_2$ |
| 1429 | F | Cl | $CH=C(Cl)CO_2$ | H | $NH_2$ |
| 1430 | F | Cl | $CH_2CH(Cl)CO_2$ | H | $NH_2$ |
| 1431 | F | Cl | $CH=C(Cl)CO_2$ | CN | $NH_2$ |
| 1432 | F | Cl | $CH_2CH(Cl)CO_2$ | CN | $NH_2$ |
| 1433 | F | Cl | S | H | $CH_3$ |
| 1434 | F | Cl | S | H | $NH_2$ |
| 1435 | F | Cl | $CH=C(Cl)CO_2$ | H | $CH_3$ |
| 1436 | F | Cl | $CH_2CH(Cl)CO_2$ | H | $CH_3$ |
| 1437 | F | Cl | $CH=C(Cl)CO_2$ | CN | $CH_3$ |
| 1438 | F | Cl | $CH_2CH(Cl)CO_2$ | CN | $CH_3$ |
| 1439 | Cl | Cl | O | H | $NH_2$ |
| 1440 | Cl | Cl | $OCH_2CO_2$ | H | $CH_3$ |
| 1441 | Cl | Cl | $OCH(CH_3)CO_2$ | H | $CH_3$ |
| 1442 | Cl | Cl | $SCH_2CO_2$ | H | $CH_3$ |
| 1443 | Cl | Cl | $CH=C(Cl)CO_2$ | H | $CH_3$ |
| 1444 | Cl | Cl | $CH_2CH(Cl)CO_2$ | H | $CH_3$ |
| 1445 | Cl | Cl | $CO_2$ | H | $CH_3$ |
| 1446 | H | Cl | O | H | $CH_3$ |
| 1447 | H | Cl | $OCH_2CO_2$ | H | $CH_3$ |
| 1448 | H | Cl | $OCH(CH_3)CO_2$ | H | $CH_3$ |
| 1449 | H | Cl | $SCH_2CO_2$ | H | $CH_3$ |
| 1450 | H | Cl | $CH=C(Cl)CO_2$ | H | $NH_2$ |
| 1451 | H | Cl | $CH_2CH(Cl)CO_2$ | H | $NH_2$ |
| 1452 | H | Cl | $CO_2$ | H | $NH_2$ |
| 1453 | H | Cl | $OCH_2CO_2$ | H | $NH_2$ |
| 1454 | H | Cl | $SCH_2CO_2$ | H | $NH_2$ |

TABLE 20

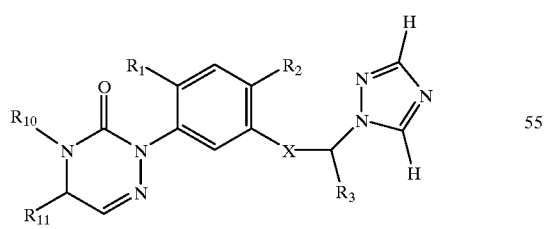

where A = B = N, $R_4 = R_5$ = H, $R_{11}$ = $CH_3$, Q = Q14 in a compound of formula I

| No | $R_1$ | $R_2$ | X | $R_3$ | $R_{10}$ |
|---|---|---|---|---|---|
| 1455 | F | Cl | $CO_2$ | H | $CH_3$ |
| 1456 | F | Cl | $CO_2$ | $CH_3$ | $CH_3$ |
| 1457 | F | Cl | $CO_2$ | $C_2H_5$ | $CH_3$ |

TABLE 20-continued

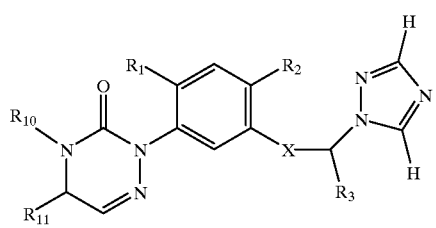

where A = B = N, $R_4 = R_5$ = H, $R_{11}$ = $CH_3$, Q = Q14 in a compound of formula I

| No | $R_1$ | $R_2$ | X | $R_3$ | $R_{10}$ |
|---|---|---|---|---|---|
| 1458 | F | Cl | $CO_2$ | H | $NH_2$ |
| 1459 | F | Cl | $CO_2$ | $CH_3$ | $NH_2$ |
| 1460 | F | Cl | $CO_2$ | $C_2H_5$ | $NH_2$ |
| 1461 | F | Cl | $CO_2$ | CN | $NH_2$ |
| 1462 | F | Cl | $CO_2$ | CN | $CH_3$ |
| 1463 | F | Cl | $OCH_2CO_2$ | H | $CH_3$ |
| 1464 | F | Cl | $OCH_2CO_2$ | $CH_3$ | $CH_3$ |
| 1465 | F | Cl | $OCH_2CO_2$ | $C_2H_5$ | $CH_3$ |
| 1466 | F | Cl | $OCH_2CO_2$ | H | $NH_2$ |
| 1467 | F | Cl | $OCH_2CO_2$ | $CH_3$ | $NH_2$ |
| 1468 | F | Cl | $OCH_2CO_2$ | $C_2H_5$ | $NH_2$ |
| 1469 | F | Cl | $OCH_2CO_2$ | CN | $NH_2$ |
| 1470 | F | Cl | $OCH_2CO_2$ | CN | $CH_3$ |
| 1471 | F | Cl | $OCH(CH_3)CO_2$ | H | $CH_3$ |
| 1472 | F | Cl | $OCH(CH_3)CO_2$ | $CH_3$ | $CH_3$ |
| 1473 | F | Cl | $OCH(CH_3)CO_2$ | $C_2H_5$ | $CH_3$ |
| 1474 | F | Cl | $OCH(CH_3)CO_2$ | H | $NH_2$ |
| 1475 | F | Cl | $OCH(CH_3)CO_2$ | $CH_3$ | $NH_2$ |
| 1476 | F | Cl | $OCH(CH_3)CO_2$ | $C_2H_5$ | $NH_2$ |
| 1477 | F | Cl | $OCH(CH_3)CO_2$ | CN | $NH_2$ |
| 1478 | F | Cl | $OCH(CH_3)CO_2$ | CN | $CH_3$ |
| 1479 | F | Cl | O | H | $CH_3$ |
| 1480 | F | Cl | O | $CH_3$ | $CH_3$ |
| 1481 | F | Cl | O | $C_2H_5$ | $CH_3$ |
| 1482 | F | Cl | O | H | $NH_2$ |
| 1483 | F | Cl | O | $CH_3$ | $NH_2$ |
| 1484 | F | Cl | O | $C_2H_5$ | $NH_2$ |
| 1485 | F | Cl | O | CN | $NH_2$ |
| 1486 | F | Cl | O | CN | $CH_3$ |
| 1487 | F | Cl | $SCH_2CO_2$ | H | $CH_3$ |
| 1488 | F | Cl | $SCH_2CO_2$ | $CH_3$ | $CH_3$ |
| 1489 | F | Cl | $SCH_2CO_2$ | $C_2H_5$ | $CH_3$ |
| 1490 | F | Cl | $SCH_2CO_2$ | H | $NH_2$ |
| 1491 | F | Cl | $SCH_2CO_2$ | $CH_3$ | $NH_2$ |
| 1492 | F | Cl | $SCH_2CO_2$ | $C_2H_5$ | $NH_2$ |
| 1493 | F | Cl | $SCH_2CO_2$ | CN | $NH_2$ |
| 1494 | F | Cl | $SCH_2CO_2$ | CN | $CH_3$ |
| 1495 | F | H | $SCH(CH_3)CO_2$ | H | $CH_3$ |
| 1496 | F | Cl | $SCH(CH_3)CO_2$ | $CH_3$ | $CH_3$ |
| 1497 | F | Cl | $SCH(CH_3)CO_2$ | $C_2H_5$ | $CH_3$ |
| 1498 | F | Cl | $SCH(CH_3)CO_2$ | H | $NH_2$ |
| 1499 | F | Cl | $SCH(CH_3)CO_2$ | $CH_3$ | $NH_2$ |
| 1500 | F | Cl | $SCH(CH_3)CO_2$ | $C_2H_5$ | $NH_2$ |
| 1501 | F | Cl | $CH=C(Cl)CO_2$ | H | $NH_2$ |
| 1502 | F | Cl | $CH_2CH(Cl)CO_2$ | H | $NH_2$ |
| 1503 | F | Cl | $CH=C(Cl)CO_2$ | CN | $NH_2$ |
| 1504 | F | Cl | $CH_2CH(Cl)CO_2$ | CN | $NH_2$ |
| 1505 | F | Cl | S | H | $CH_3$ |
| 1506 | F | Cl | S | H | $NH_2$ |
| 1507 | F | Cl | $CH=C(Cl)CO_2$ | H | $CH_3$ |
| 1508 | F | Cl | $CH_2CH(Cl)CO_2$ | H | $CH_3$ |
| 1509 | F | Cl | $CH=C(Cl)CO_2$ | CN | $CH_3$ |
| 1510 | F | Cl | $CH_2CH(Cl)CO_2$ | CN | $CH_3$ |
| 1511 | Cl | Cl | O | H | $NH_2$ |
| 1512 | Cl | Cl | $OCH_2CO_2$ | H | $CH_3$ |
| 1513 | Cl | Cl | $OCH(CH_3)CO_2$ | H | $CH_3$ |
| 1514 | Cl | Cl | $SCH_2CO_2$ | H | $CH_3$ |
| 1515 | Cl | Cl | $CH=C(Cl)CO_2$ | H | $CH_3$ |
| 1516 | Cl | Cl | $CH_2CH(Cl)CO_2$ | H | $CH_3$ |
| 1517 | Cl | Cl | $CO_2$ | H | $CH_3$ |
| 1518 | H | Cl | O | H | $CH_3$ |
| 1519 | H | Cl | $OCH_2CO_2$ | H | $CH_3$ |

TABLE 20-continued where A = B = N, R$_4$ = R$_5$ = H, R$_{11}$ = CH$_3$, Q = Q14 in a compound of formula I

| No | R$_1$ | R$_2$ | X | R$_3$ | R$_{10}$ |
|---|---|---|---|---|---|
| 1520 | H | Cl | OCH(CH$_3$)CO$_2$ | H | CH$_3$ |
| 1521 | H | Cl | SCH$_2$CO$_2$ | H | CH$_3$ |
| 1522 | H | Cl | CH=C(Cl)CO$_2$ | H | NH$_2$ |
| 1523 | H | Cl | CH$_2$CH(Cl)CO$_2$ | H | NH$_2$ |
| 1524 | H | Cl | CO$_2$ | H | NH$_2$ |
| 1525 | H | Cl | OCH$_2$CO$_2$ | H | NH$_2$ |
| 1526 | H | Cl | SCH$_2$CO$_2$ | H | NH$_2$ |

TABLE 21 where A = B = N, R$_4$ = R$_5$ = H, Q = Q15 in a compound of formula I

| No | R$_1$ | R$_2$ | X | R$_3$ | R$_{10}$ |
|---|---|---|---|---|---|
| 1527 | F | Cl | CO$_2$ | H | CH$_3$ |
| 1528 | F | Cl | CO$_2$ | CH$_3$ | CH$_3$ |
| 1529 | F | Cl | CO$_2$ | C$_2$H$_5$ | CH$_3$ |
| 1530 | F | Cl | CO$_2$ | H | NH$_2$ |
| 1531 | F | Cl | CO$_2$ | CH$_3$ | NH$_2$ |
| 1532 | F | Cl | CO$_2$ | C$_2$H$_5$ | NH$_2$ |
| 1533 | F | Cl | CO$_2$ | CN | NH$_2$ |
| 1534 | F | Cl | CO$_2$ | CN | CH$_3$ |
| 1535 | F | Cl | OCH$_2$CO$_2$ | H | CH$_3$ |
| 1536 | F | Cl | OCH$_2$CO$_2$ | CH$_3$ | CH$_3$ |
| 1537 | F | Cl | OCH$_2$CO$_2$ | C$_2$H$_5$ | CH$_3$ |
| 1538 | F | Cl | OCH$_2$CO$_2$ | H | NH$_2$ |
| 1539 | F | Cl | OCH$_2$CO$_2$ | CH$_3$ | NH$_2$ |
| 1540 | F | Cl | OCH$_2$CO$_2$ | C$_2$H$_5$ | NH$_2$ |
| 1541 | F | Cl | OCH$_2$CO$_2$ | CN | NH$_2$ |
| 1542 | F | Cl | OCH$_2$CO$_2$ | CN | CH$_3$ |
| 1543 | F | Cl | OCH(CH$_3$)CO$_2$ | H | CH$_3$ |
| 1544 | F | Cl | OCH(CH$_3$)CO$_2$ | CH$_3$ | CH$_3$ |
| 1545 | F | Cl | OCH(CH$_3$)CO$_2$ | C$_2$H$_5$ | CH$_3$ |
| 1546 | F | Cl | OCH(CH$_3$)CO$_2$ | H | NH$_2$ |
| 1547 | F | Cl | OCH(CH$_3$)CO$_2$ | CH$_3$ | NH$_2$ |
| 1548 | F | Cl | OCH(CH$_3$)CO$_2$ | C$_2$H$_5$ | NH$_2$ |
| 1549 | F | Cl | OCH(CH$_3$)CO$_2$ | CN | NH$_2$ |
| 1550 | F | Cl | OCH(CH$_3$)CO$_2$ | CN | CH$_3$ |
| 1551 | F | Cl | O | H | CH$_3$ |
| 1552 | F | Cl | O | CH$_3$ | CH$_3$ |
| 1553 | F | Cl | O | C$_2$H$_5$ | CH$_3$ |
| 1554 | F | Cl | O | H | NH$_2$ |
| 1555 | F | Cl | O | CH$_3$ | NH$_2$ |
| 1556 | F | Cl | O | C$_2$H$_5$ | NH$_2$ |
| 1557 | F | Cl | O | CN | NH$_2$ |
| 1558 | F | Cl | O | CN | CH$_3$ |
| 1559 | F | Cl | SCH$_2$CO$_2$ | H | CH$_3$ |
| 1560 | F | Cl | SCH$_2$CO$_2$ | CH$_3$ | CH$_3$ |
| 1561 | F | Cl | SCH$_2$CO$_2$ | C$_2$H$_5$ | CH$_3$ |
| 1562 | F | Cl | SCH$_2$CO$_2$ | H | NH$_2$ |
| 1563 | F | Cl | SCH$_2$CO$_2$ | CH$_3$ | NH$_2$ |
| 1564 | F | Cl | SCH$_2$CO$_2$ | C$_2$H$_5$ | NH$_2$ |
| 1565 | F | Cl | SCH$_2$CO$_2$ | CN | NH$_2$ |
| 1566 | F | Cl | SCH$_2$CO$_2$ | CN | CH$_3$ |
| 1567 | F | H | SCH(CH$_3$)CO$_2$ | H | CH$_3$ |
| 1568 | F | Cl | SCH(CH$_3$)CO$_2$ | CH$_3$ | CH$_3$ |
| 1569 | F | Cl | SCH(CH$_3$)CO$_2$ | C$_2$H$_5$ | CH$_3$ |
| 1570 | F | Cl | SCH(CH$_3$)CO$_2$ | H | NH$_2$ |
| 1571 | F | Cl | SCH(CH$_3$)CO$_2$ | CH$_3$ | NH$_2$ |
| 1572 | F | Cl | SCH(CH$_3$)CO$_2$ | C$_2$H$_5$ | NH$_2$ |
| 1573 | F | Cl | CH=C(Cl)CO$_2$ | H | NH$_2$ |
| 1574 | F | Cl | CH$_2$CH(Cl)CO$_2$ | H | NH$_2$ |
| 1575 | F | Cl | CH=C(Cl)CO$_2$ | CN | NH$_2$ |
| 1576 | F | Cl | CH$_2$CH(Cl)CO$_2$ | CN | NH$_2$ |
| 1577 | F | Cl | S | H | CH$_3$ |
| 1578 | F | Cl | S | H | NH$_2$ |
| 1579 | F | Cl | CH=C(Cl)CO$_2$ | H | CH$_3$ |
| 1580 | F | Cl | CH$_2$CH(Cl)CO$_2$ | H | CH$_3$ |
| 1581 | F | Cl | CH=C(Cl)CO$_2$ | CN | CH$_3$ |
| 1582 | F | Cl | CH$_2$CH(Cl)CO$_2$ | CN | CH$_3$ |
| 1583 | Cl | Cl | O | H | NH$_2$ |
| 1584 | Cl | Cl | OCH$_2$CO$_2$ | H | CH$_3$ |
| 1585 | Cl | Cl | OCH(CH$_3$)CO$_2$ | H | CH$_3$ |
| 1586 | Cl | Cl | SCH$_2$CO$_2$ | H | CH$_3$ |
| 1587 | Cl | Cl | CH=C(Cl)CO$_2$ | H | CH$_3$ |
| 1588 | Cl | Cl | CH$_2$CH(Cl)CO$_2$ | H | CH$_3$ |
| 1589 | Cl | Cl | CO$_2$ | H | CH$_3$ |
| 1590 | H | Cl | O | H | CH$_3$ |
| 1591 | H | Cl | OCH$_2$CO$_2$ | H | CH$_3$ |
| 1592 | H | Cl | OCH(CH$_3$)CO$_2$ | H | CH$_3$ |
| 1593 | H | Cl | SCH$_2$CO$_2$ | H | CH$_3$ |
| 1594 | H | Cl | CH=C(Cl)CO$_2$ | H | NH$_2$ |
| 1595 | H | Cl | CH$_2$CH(Cl)CO$_2$ | H | NH$_2$ |
| 1596 | H | Cl | CO$_2$ | H | NH$_2$ |
| 1597 | H | Cl | OCH$_2$CO$_2$ | H | NH$_2$ |
| 1598 | H | Cl | SCH$_2$CO$_2$ | H | NH$_2$ |

TABLE 22 where A = B = N, R$_4$ = R$_5$ = H, Q = Q16 in a compound of formula I

| No | R$_1$ | R$_2$ | X | R$_3$ |
|---|---|---|---|---|
| 1599 | F | Cl | CO$_2$ | H |
| 1600 | F | Cl | CO$_2$ | CH$_3$ |

TABLE 22-continued

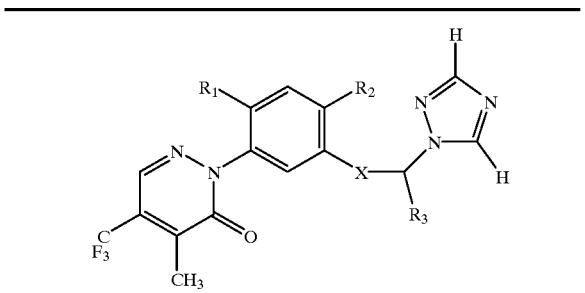

where A = B = N, $R_4 = R_5$ = H, Q = Q16 in a compound of formula I

| No | $R_1$ | $R_2$ | X | $R_3$ |
|---|---|---|---|---|
| 1601 | F | Cl | $CO_2$ | $C_2H_5$ |
| 1602 | F | Cl | $CO_2$ | Ph |
| 1603 | F | Cl | $CO_2$ | $CH_2Ph$ |
| 1604 | F | Cl | $CO_2$ | Ph-4-Cl |
| 1605 | F | Cl | $CO_2$ | $CH_2Ph$-4-Cl |
| 1606 | F | Cl | $CO_2$ | 3-Py |
| 1607 | F | Cl | $OCH_2CO_2$ | H |
| 1608 | F | Cl | $OCH_2CO_2$ | $CH_3$ |
| 1609 | F | Cl | $OCH_2CO_2$ | $C_2H_5$ |
| 1610 | F | Cl | $OCH_2CO_2$ | Ph |
| 1611 | F | Cl | $OCH_2CO_2$ | $CH_2Ph$ |
| 1612 | F | Cl | $OCH_2CO_2$ | Ph-4-Cl |
| 1613 | F | Cl | $OCH_2CO_2$ | $CH_2Ph$-4-Cl |
| 1614 | F | Cl | $OCH_2CO_2$ | 3-Py |
| 1615 | F | Cl | $OCH(CH_3)CO_2$ | H |
| 1616 | F | Cl | $OCH(CH_3)CO_2$ | $CH_3$ |
| 1617 | F | Cl | $OCH(CH_3)CO_2$ | $C_2H_5$ |
| 1618 | F | Cl | $OCH(CH_3)CO_2$ | Ph |
| 1619 | F | Cl | $OCH(CH_3)CO_2$ | $CH_2Ph$ |
| 1620 | F | Cl | $OCH(CH_3)CO_2$ | Ph-4-Cl |
| 1621 | F | Cl | $OCH(CH_3)CO_2$ | $CH_2Ph$-4-Cl |
| 1622 | F | Cl | $OCH(CH_3)CO_2$ | 3-Py |
| 1623 | F | Cl | O | H |
| 1624 | F | Cl | O | $CH_3$ |
| 1625 | F | Cl | O | $C_2H_5$ |
| 1626 | F | Cl | O | Ph |
| 1627 | F | Cl | O | $CH_2Ph$ |
| 1628 | F | Cl | O | Ph-4-Cl |
| 1629 | F | Cl | O | $CH_2Ph$-4-Cl |
| 1630 | F | Cl | O | 3-Py |
| 1631 | F | Cl | $SCH_2CO_2$ | H |
| 1632 | F | Cl | $SCH_2CO_2$ | $CH_3$ |
| 1633 | F | Cl | $SCH_2CO_2$ | $C_2H_5$ |
| 1634 | F | Cl | $SCH_2CO_2$ | Ph |
| 1635 | F | Cl | $SCH_2CO_2$ | $CH_2Ph$ |
| 1636 | F | Cl | $SCH_2CO_2$ | Ph-4-Cl |
| 1637 | F | Cl | $SCH_2CO_2$ | $CH_2Ph$-4-Cl |
| 1638 | F | Cl | $SCH_2CO_2$ | 3-Py |
| 1639 | F | H | $SCH(CH_3)CO_2$ | H |
| 1640 | F | Cl | $SCH(CH_3)CO_2$ | $CH_3$ |
| 1641 | F | Cl | $SCH(CH_3)CO_2$ | $C_2H_5$ |
| 1642 | F | Cl | $SCH(CH_3)CO_2$ | Ph |
| 1643 | F | Cl | $SCH(CH_3)CO_2$ | $CH_2Ph$ |
| 1644 | F | Cl | $SCH(CH_3)CO_2$ | Ph-4-Cl |
| 1645 | F | Cl | $SCH(CH_3)CO_2$ | $CH_2Ph$-4-Cl |
| 1646 | F | Cl | $SCH(CH_3)CO_2$ | 3-Py |
| 1647 | F | Cl | S | H |
| 1648 | F | Cl | S | $CH_3$ |
| 1649 | F | Cl | S | $C_2H_5$ |
| 1650 | F | Cl | S | Ph |
| 1651 | F | Cl | S | $CH_2Ph$ |
| 1652 | F | Cl | S | Ph-4-Cl |
| 1653 | F | Cl | $CH=C(Cl)CO_2$ | H |
| 1654 | F | Cl | $CH_2CH(Cl)CO_2$ | H |
| 1655 | Cl | Cl | O | H |
| 1656 | Cl | Cl | $OCH_2CO_2$ | H |
| 1657 | Cl | Cl | $CH=C(Cl)CO_2$ | H |
| 1658 | Cl | Cl | $CH_2CH(Cl)CO_2$ | H |
| 1659 | Cl | Cl | $SCH_2CO_2$ | H |
| 1660 | Cl | Cl | $SCH(CH_3)CO_2$ | H |

TABLE 22-continued

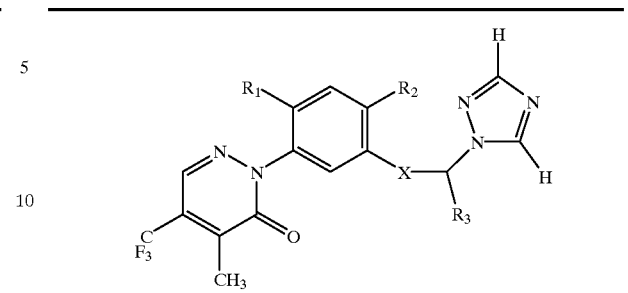

where A = B = N, $R_4 = R_5$ = H, Q = Q16 in a compound of formula I

| No | $R_1$ | $R_2$ | X | $R_3$ |
|---|---|---|---|---|
| 1661 | Cl | Cl | $CO_2$ | H |
| 1662 | H | Cl | O | H |
| 1663 | H | Cl | $OCH_2CO_2$ | H |
| 1664 | H | Cl | $OCH(CH_3)CO_2$ | H |
| 1665 | H | Cl | $SCH_2CO_2$ | H |
| 1666 | H | Cl | $CH=C(Cl)CO_2$ | H |
| 1667 | H | Cl | $CH_2CH(Cl)CO_2$ | H |
| 1668 | H | Cl | $CO_2$ | H |
| 1669 | F | Cl | $OCH_2CO_2$ | Ph-4-F |
| 1670 | F | Cl | $SCH_2CO_2$ | Ph-4-F |

TABLE 23 where A = $R_4 = R_5$ = H, A = B = N, $R_{10}$ = $CH_3$,
$R_{11}$ = $CH_3$, Z = O in a compound of formula I

| No | $R_1$ | $R_2$ | X | Q |
|---|---|---|---|---|
| 1671 | F | Cl | $OCH(CH_3)CO$ | Q1 |
| 1672 | F | Cl | $OCH(CH_3)CO$ | Q2 |
| 1673 | F | Cl | $OCH(CH_3)CO$ | Q3 |
| 1674 | F | Cl | $OCH(CH_3)CO$ | Q4 |
| 1675 | F | Cl | $OCH(CH_3)CO$ | Q5 |
| 1676 | F | Cl | $OCH(CH_3)CO$ | Q6 |
| 1677 | F | Cl | $OCH(CH_3)CO$ | Q7 |
| 1678 | F | Cl | $OCH(CH_3)CO$ | Q8 |
| 1679 | F | Cl | $OCH(CH_3)CO$ | Q9 |
| 1680 | F | Cl | $OCH(CH_3)CO$ | Q10 |
| 1681 | F | Cl | $OCH(CH_3)CO$ | Q11 |
| 1682 | F | Cl | $OCH(CH_3)CO$ | Q12 |
| 1683 | F | Cl | $OCH(CH_3)CO$ | Q13 |
| 1684 | F | Cl | $OCH(CH_3)CO$ | Q14 |
| 1685 | F | Cl | $OCH(CH_3)CO$ | Q16 |
| 1686 | F | Cl | $OCH_2CO$ | Q1 |
| 1687 | F | Cl | $OCH_2CO$ | Q2 |
| 1688 | F | Cl | $OCH_2CO$ | Q3 |
| 1689 | F | Cl | $OCH_2CO$ | Q4 |
| 1690 | F | Cl | $OCH_2CO$ | Q5 |
| 1691 | F | Cl | $OCH_2CO$ | Q6 |
| 1692 | F | Cl | $OCH_2CO$ | Q7 |
| 1693 | F | Cl | $OCH_2CO$ | Q8 |
| 1694 | F | Cl | $OCH_2CO$ | Q9 |
| 1695 | F | Cl | $OCH_2CO$ | Q10 |
| 1696 | F | Cl | $OCH_2CO$ | Q11 |
| 1697 | F | Cl | $OCH_2CO$ | Q12 |
| 1698 | F | Cl | $OCH_2CO$ | Q13 |
| 1699 | F | Cl | $OCH_2CO$ | Q14 |
| 1700 | F | Cl | $OCH_2CO$ | Q16 |
| 1701 | F | Cl | $CH_2CH(Cl)CO$ | Q1 |

TABLE 23-continued where A = R$_4$ = R$_5$ = H, A = B = N, R$_{10}$ = CH$_3$,
R$_{11}$ = CH$_3$, Z = O in a compound of formula I

| No | R$_1$ | R$_2$ | X | Q |
|---|---|---|---|---|
| 1702 | F | Cl | CH$_2$CH(Cl)CO | Q2 |
| 1703 | F | Cl | CH$_2$CH(Cl)CO | Q3 |
| 1704 | F | Cl | CH$_2$CH(Cl)CO | Q4 |
| 1705 | F | Cl | CH$_2$CH(Cl)CO | Q5 |
| 1706 | F | Cl | CH$_2$CH(Cl)CO | Q6 |
| 1707 | F | Cl | CH$_2$CH(Cl)CO | Q7 |
| 1708 | F | Cl | CH$_2$CH(Cl)CO | Q8 |
| 1709 | F | Cl | CH$_2$CH(Cl)CO | Q9 |
| 1710 | F | Cl | CH$_2$CH(Cl)CO | Q10 |
| 1711 | F | Cl | CH$_2$CH(Cl)CO | Q11 |
| 1712 | F | Cl | CH$_2$CH(Cl)CO | Q12 |
| 1713 | F | Cl | CH$_2$CH(Cl)CO | Q13 |
| 1714 | F | Cl | CH$_2$CH(Cl)CO | Q14 |
| 1715 | F | Cl | CH$_2$CH(Cl)CO | Q16 |
| 1716 | F | Cl | CH=C(Cl)CO | Q1 |
| 1717 | F | Cl | CH=C(Cl)CO | Q2 |
| 1718 | F | Cl | CH=C(Cl)CO | Q3 |
| 1719 | F | Cl | CH=C(Cl)CO | Q4 |
| 1720 | F | Cl | CH=C(Cl)CO | Q5 |
| 1721 | F | Cl | CH=C(Cl)CO | Q6 |
| 1722 | F | Cl | CH=C(Cl)CO | Q7 |
| 1723 | F | Cl | CH=C(Cl)CO | Q8 |
| 1724 | F | Cl | CH=C(Cl)CO | Q9 |
| 1725 | F | Cl | CH=C(Cl)CO | Q10 |
| 1726 | F | Cl | CH=C(Cl)CO | Q11 |
| 1727 | F | Cl | CH=C(Cl)CO | Q12 |
| 1728 | F | Cl | CH=C(Cl)CO | Q13 |
| 1729 | F | Cl | CH=C(Cl)CO | Q14 |
| 1730 | F | Cl | CH=C(Cl)CO | Q16 |
| 1731 | F | Cl | CO | Q1 |
| 1732 | F | Cl | CO | Q2 |
| 1733 | F | Cl | CO | Q3 |
| 1734 | F | Cl | CO | Q4 |
| 1735 | F | Cl | CO | Q5 |
| 1736 | F | Cl | CO | Q6 |
| 1737 | F | Cl | CO | Q7 |
| 1738 | F | Cl | CO | Q8 |
| 1739 | F | Cl | CO | Q9 |
| 1740 | F | Cl | CO | Q10 |
| 1741 | F | Cl | CO | Q11 |
| 1742 | F | Cl | CO | Q12 |
| 1743 | F | Cl | CO | Q13 |
| 1744 | F | Cl | CO | Q14 |
| 1745 | F | Cl | CO | Q16 |
| 1746 | F | Cl | SCH$_2$CO | Q1 |
| 1747 | F | Cl | SCH$_2$CO | Q2 |
| 1748 | F | Cl | SCH$_2$CO | Q3 |
| 1749 | F | Cl | SCH$_2$CO | Q4 |
| 1750 | F | Cl | SCH$_2$CO | Q5 |
| 1751 | F | Cl | SCH$_2$CO | Q6 |
| 1752 | F | Cl | SCH$_2$CO | Q7 |
| 1753 | F | Cl | SCH$_2$CO | Q8 |
| 1754 | F | Cl | SCH$_2$CO | Q9 |
| 1755 | F | Cl | SCH$_2$CO | Q10 |
| 1756 | F | Cl | SCH$_2$CO | Q11 |
| 1757 | F | Cl | SCH$_2$CO | Q12 |
| 1758 | F | Cl | SCH$_2$CO | Q13 |
| 1759 | F | Cl | SCH$_2$CO | Q14 |
| 1760 | F | Cl | SCH$_2$CO | Q16 |
| 1761 | Cl | Cl | CH=C(Cl)CO | Q1 |
| 1762 | Cl | Cl | CH=C(Cl)CO | Q3 |
| 1763 | Cl | Cl | CH=C(Cl)CO | Q6 |
| 1764 | Cl | Cl | CH=C(Cl)CO | Q7 |
| 1765 | Cl | Cl | CH=C(Cl)CO | Q8 |
| 1766 | Cl | Cl | CH=C(Cl)CO | Q10 |
| 1767 | Cl | Cl | CH=C(Cl)CO | Q11 |
| 1768 | Cl | Cl | CH=C(Cl)CO | Q12 |
| 1769 | Cl | Cl | CH=C(Cl)CO | Q16 |
| 1770 | Cl | Cl | CH$_2$CH(Cl)CO | Q1 |
| 1771 | Cl | Cl | CH$_2$CH(Cl)CO | Q3 |
| 1772 | Cl | Cl | CH$_2$CH(Cl)CO | Q6 |
| 1773 | Cl | Cl | CH$_2$CH(Cl)CO | Q7 |
| 1774 | Cl | Cl | CH$_2$CH(Cl)CO | Q8 |
| 1775 | Cl | Cl | CH$_2$CH(Cl)CO | Q10 |
| 1776 | Cl | Cl | CH$_2$CH(Cl)CO | Q11 |
| 1777 | Cl | Cl | CH$_2$CH(Cl)CO | Q12 |
| 1778 | Cl | Cl | CH$_2$CH(Cl)CO | Q16 |
| 1779 | Cl | Cl | OCH$_2$CO | Q1 |
| 1780 | Cl | Cl | OCH$_2$CO | Q3 |
| 1781 | Cl | Cl | OCH$_2$CO | Q6 |
| 1782 | Cl | Cl | OCH$_2$CO | Q7 |
| 1783 | Cl | Cl | OCH$_2$CO | Q8 |
| 1784 | Cl | Cl | OCH$_2$CO | Q10 |
| 1785 | Cl | Cl | OCH$_2$CO | Q11 |
| 1786 | Cl | Cl | OCH$_2$CO | Q12 |
| 1787 | Cl | Cl | OCH$_2$CO | Q16 |
| 1788 | Cl | Cl | SCH$_2$CO | Q1 |
| 1789 | Cl | Cl | SCH$_2$CO | Q3 |
| 1790 | Cl | Cl | SCH$_2$CO | Q6 |
| 1791 | Cl | Cl | SCH$_2$CO | Q7 |
| 1792 | Cl | Cl | SCH$_2$CO | Q8 |
| 1793 | Cl | Cl | SCH$_2$CO | Q10 |
| 1794 | Cl | Cl | SCH$_2$CO | Q11 |
| 1795 | Cl | Cl | SCH$_2$CO | Q12 |
| 1796 | Cl | Cl | SCH$_2$CO | Q16 |
| 1797 | Cl | Cl | CO | Q1 |
| 1798 | Cl | Cl | CO | Q3 |
| 1799 | Cl | Cl | CO | Q6 |
| 1800 | Cl | Cl | CO | Q7 |
| 1801 | Cl | Cl | CO | Q8 |
| 1802 | Cl | Cl | CO | Q10 |
| 1803 | Cl | Cl | CO | Q11 |
| 1804 | Cl | Cl | CO | Q12 |
| 1805 | Cl | Cl | CO | Q16 |
| 1806 | Cl | Cl | OCH(CH$_3$)CO | Q1 |
| 1807 | Cl | Cl | OCH(CH$_3$)CO | Q3 |
| 1808 | Cl | Cl | OCH(CH$_3$)CO | Q6 |
| 1809 | Cl | Cl | OCH(CH$_3$)CO | Q7 |
| 1810 | Cl | Cl | OCH(CH$_3$)CO | Q8 |
| 1811 | Cl | Cl | OCH(CH$_3$)CO | Q10 |
| 1812 | Cl | Cl | OCH(CH$_3$)CO | Q11 |
| 1813 | Cl | Cl | OCH(CH$_3$)CO | Q12 |
| 1814 | Cl | Cl | OCH(CH$_3$)CO | Q16 |
| 1815 | H | Cl | CH=C(Cl)CO | Q1 |
| 1816 | H | Cl | CH=C(Cl)CO | Q3 |
| 1818 | H | Cl | CH=C(Cl)CO | Q6 |
| 1818 | H | Cl | CH=C(Cl)CO | Q7 |
| 1819 | H | Cl | CH=C(Cl)CO | Q8 |
| 1820 | H | Cl | CH=C(Cl)CO | Q10 |
| 1821 | H | Cl | CH=C(Cl)CO | Q11 |
| 1822 | H | Cl | CH=C(Cl)CO | Q12 |
| 1823 | H | Cl | CH=C(Cl)CO | Q16 |
| 1824 | H | Cl | CH$_2$CH(Cl)CO | Q1 |
| 1825 | H | Cl | CH$_2$CH(Cl)CO | Q3 |
| 1826 | H | Cl | CH$_2$CH(Cl)CO | Q6 |
| 1827 | H | Cl | CH$_2$CH(Cl)CO | Q7 |
| 1828 | H | Cl | CH$_2$CH(Cl)CO | Q8 |
| 1829 | H | Cl | CH$_2$CH(Cl)CO | Q10 |

TABLE 23-continued

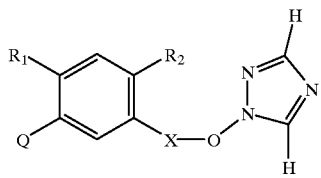

where A = R$_4$ = R$_5$ = H, A = B = N, R$_{10}$ = CH$_3$,
R$_{11}$ = CH$_3$, Z = O in a compound of formula I

| No | R$_1$ | R$_2$ | X | Q |
|---|---|---|---|---|
| 1830 | H | Cl | CH$_2$CH(Cl)CO | Q11 |
| 1831 | H | Cl | CH$_2$CH(Cl)CO | Q12 |
| 1832 | H | Cl | CH$_2$CH(Cl)CO | Q16 |
| 1833 | H | Cl | OCH$_2$CO | Q1 |
| 1834 | H | Cl | OCH$_2$CO | Q3 |
| 1835 | H | Cl | OCH$_2$CO | Q6 |
| 1836 | H | Cl | OCH$_2$CO | Q7 |
| 1837 | H | Cl | OCH$_2$CO | Q8 |
| 1838 | H | Cl | OCH$_2$CO | Q10 |
| 1839 | H | Cl | OCH$_2$CO | Q11 |
| 1840 | H | Cl | OCH$_2$CO | Q12 |
| 1841 | H | Cl | OCH$_2$CO | Q16 |
| 1842 | H | Cl | SCH$_2$CO | Q1 |
| 1843 | H | Cl | SCH$_2$CO | Q3 |
| 1844 | H | Cl | SCH$_2$CO | Q6 |
| 1845 | H | Cl | SCH$_2$CO | Q7 |
| 1846 | H | Cl | SCH$_2$CO | Q8 |
| 1847 | H | Cl | SCH$_2$CO | Q10 |
| 1848 | H | Cl | SCH$_2$CO | Q11 |
| 1849 | H | Cl | SCH$_2$CO | Q12 |
| 1850 | H | Cl | SCH$_2$CO | Q16 |
| 1851 | H | Cl | CO | Q1 |
| 1852 | H | Cl | CO | Q3 |
| 1853 | H | Cl | CO | Q6 |
| 1854 | H | Cl | CO | Q7 |
| 1855 | H | Cl | CO | Q8 |
| 1856 | H | Cl | CO | Q10 |
| 1857 | H | Cl | CO | Q11 |
| 1858 | H | Cl | CO | Q12 |
| 1859 | H | Cl | CO | Q16 |
| 1860 | H | Cl | OCH(CH$_3$)CO | Q1 |
| 1861 | H | Cl | OCH(CH$_3$)CO | Q3 |
| 1862 | H | Cl | OCH(CH$_3$)CO | Q6 |
| 1863 | H | Cl | OCH(CH$_3$)CO | Q7 |
| 1864 | H | Cl | OCH(CH$_3$)CO | Q8 |
| 1865 | H | Cl | OCH(CH$_3$)CO | Q10 |
| 1866 | H | Cl | OCH(CH$_3$)CO | Q11 |
| 1867 | H | Cl | OCH(CH$_3$)CO | Q12 |
| 1868 | H | Cl | OCH(CH$_3$)CO | Q16 |

TABLE 24

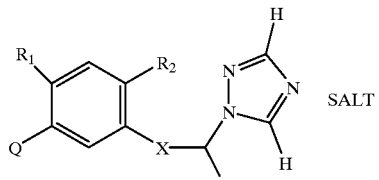

where R$_3$ = R$_4$ = R$_5$ = H, A = B = N, R$_{10}$ = CH$_3$
in a compound of formula I

| No | R$_1$ | R$_2$ | X | Q | Salt |
|---|---|---|---|---|---|
| 1869 | F | Cl | O | Q1 | HCl |
| 1870 | F | Cl | OCH$_2$CO$_2$ | Q1 | HCl |
| 1871 | F | Cl | SCH$_2$CO$_2$ | Q1 | HCl |
| 1872 | F | Cl | CO$_2$ | Q1 | HCl |

TABLE 24-continued

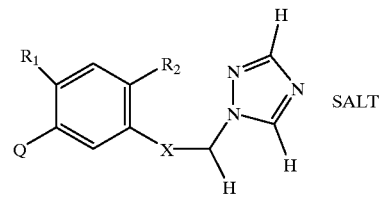

where R$_3$ = R$_4$ = R$_5$ = H, A = B = N, R$_{10}$ = CH$_3$
in a compound of formula I

| No | R$_1$ | R$_2$ | X | Q | Salt |
|---|---|---|---|---|---|
| 1873 | F | Cl | CH$_2$CH(Cl)CO$_2$ | Q1 | HCl |
| 1874 | F | Cl | CH=C(Cl)CO$_2$ | Q1 | HCl |
| 1875 | F | Cl | OCH$_2$CO$_2$ | Q1 | H$_3$PO$_4$ |
| 1876 | F | Cl | OCH$_2$CO$_2$ | Q1 | CH$_3$CO$_2$H |
| 1877 | F | Cl | OCH$_2$CO$_2$ | Q1 | HCO$_2$CO$_2$H |
| 1878 | F | Cl | SCH$_2$CO$_2$ | Q1 | HCO$_2$CO$_2$H |
| 1879 | F | Cl | CO$_2$ | Q1 | HCO$_2$CO$_2$H |
| 1880 | F | Cl | CH$_2$CH(Cl)CO$_2$ | Q1 | HCO$_2$CO$_2$H |
| 1881 | F | Cl | CH=C(Cl)CO$_2$ | Q1 | HCO$_2$CO$_2$H |
| 1882 | Cl | Cl | O | Q1 | HCl |
| 1883 | Cl | Cl | OCH$_2$CO$_2$ | Q1 | HCl |
| 1884 | Cl | Cl | SCH$_2$CO$_2$ | Q1 | HCl |
| 1885 | Cl | Cl | CO$_2$ | Q1 | HCl |
| 1886 | Cl | Cl | CH$_2$CH(Cl)CO$_2$ | Q1 | HCl |
| 1887 | Cl | Cl | CH=C(Cl)CO$_2$ | Q1 | HCl |
| 1888 | Cl | Cl | O | Q1 | HCO$_2$CO$_2$H |
| 1889 | Cl | Cl | OCH$_2$CO$_2$ | Q1 | HCO$_2$CO$_2$H |
| 1890 | Cl | Cl | SCH$_2$CO$_2$ | Q1 | HCO$_2$CO$_2$H |
| 1891 | Cl | Cl | CO$_2$ | Q1 | HCO$_2$CO$_2$H |
| 1892 | Cl | Cl | CH$_2$CH(Cl)CO$_2$ | Q1 | HCO$_2$CO$_2$H |
| 1893 | Cl | Cl | CH=C(Cl)CO$_2$ | Q1 | HCO$_2$CO$_2$H |
| 1894 | H | Cl | O | Q1 | HCl |
| 1895 | H | Cl | OCH$_2$CO$_2$ | Q1 | HCl |
| 1896 | H | Cl | SCH$_2$CO$_2$ | Q1 | HCl |
| 1897 | H | Cl | CO$_2$ | Q1 | HCl |
| 1898 | H | Cl | CH$_2$CH(Cl)CO$_2$ | Q1 | HCl |
| 1899 | H | Cl | CH=C(Cl)CO$_2$ | Q1 | HCl |
| 1900 | H | Cl | O | Q1 | HCO$_2$CO$_2$H |
| 1901 | H | Cl | OCH$_2$CO$_2$ | Q1 | HCO$_2$CO$_2$H |
| 1902 | H | Cl | SCH$_2$CO$_2$ | Q1 | HCO$_2$CO$_2$H |
| 1903 | H | Cl | CO$_2$ | Q1 | HCO$_2$CO$_2$H |
| 1904 | H | Cl | CH$_2$CH(Cl)CO$_2$ | Q1 | HCO$_2$CO$_2$H |
| 1905 | H | Cl | CH=C(Cl)CO$_2$ | Q1 | HCO$_2$CO$_2$H |
| 1906 | F | Cl | O | Q3 | HCl |
| 1907 | F | Cl | OCH$_2$CO$_2$ | Q3 | HCl |
| 1908 | F | Cl | SCH$_2$CO$_2$ | Q3 | HCl |
| 1909 | F | Cl | CO$_2$ | Q3 | HCl |
| 1910 | F | Cl | CH$_2$CH(Cl)CO$_2$ | Q3 | HCl |
| 1911 | F | Cl | CH=C(Cl)CO$_2$ | Q3 | HCl |
| 1912 | F | Cl | O | Q7 | HCl |
| 1913 | F | Cl | OCH$_2$CO$_2$ | Q7 | HCl |
| 1914 | F | Cl | SCH$_2$CO$_2$ | Q7 | HCl |
| 1915 | F | Cl | CO$_2$ | Q7 | HCl |
| 1916 | F | Cl | CH$_2$CH(Cl)CO$_2$ | Q7 | HCl |
| 1917 | F | Cl | CH=C(Cl)CO$_2$ | Q7 | HCl |
| 1918 | F | Cl | O | Q8 | HCl |
| 1919 | F | Cl | OCH$_2$CO$_2$ | Q8 | HCl |
| 1920 | F | Cl | SCH$_2$CO$_2$ | Q8 | HCl |
| 1921 | F | Cl | CO$_2$ | Q8 | HCl |
| 1922 | F | Cl | CH$_2$CH(Cl)CO$_2$ | Q8 | HCl |
| 1923 | F | Cl | CH=C(Cl)CO$_2$ | Q8 | HCl |
| 1924 | F | Cl | O | Q10 | HCl |
| 1925 | F | Cl | OCH$_2$CO$_2$ | Q10 | HCl |
| 1926 | F | Cl | SCH$_2$CO$_2$ | Q10 | HCl |
| 1927 | F | Cl | CO$_2$ | Q10 | HCl |
| 1928 | F | Cl | CH$_2$CH(Cl)CO$_2$ | Q10 | HCl |
| 1929 | F | Cl | CH=C(Cl)CO$_2$ | Q10 | HCl |
| 1930 | F | Cl | O | Q11 | HCl |
| 1931 | F | Cl | OCH$_2$CO$_2$ | Q11 | HCl |
| 1932 | F | Cl | SCH$_2$CO$_2$ | Q11 | HCl |
| 1933 | F | Cl | CO$_2$ | Q11 | HCl |
| 1934 | F | Cl | CH$_2$CH(Cl)CO$_2$ | Q11 | HCl |
| 1935 | F | Cl | CH=C(Cl)CO$_2$ | Q11 | HCl |

TABLE 24-continued

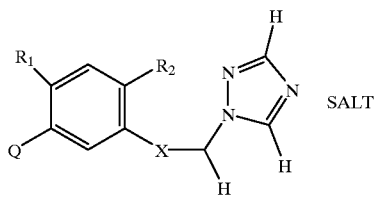

where $R_3 = R_4 = R_5 = H$, $A = B = N$, $R_{10} = CH_3$
in a compound of formula I

| No | $R_1$ | $R_2$ | X | Q | Salt |
|---|---|---|---|---|---|
| 1936 | Cl | Cl | O | Q12 | HCl |
| 1937 | Cl | Cl | $OCH_2CO_2$ | Q12 | HCl |
| 1938 | Cl | Cl | $SCH_2CO_2$ | Q12 | HCl |

TABLE 24-continued

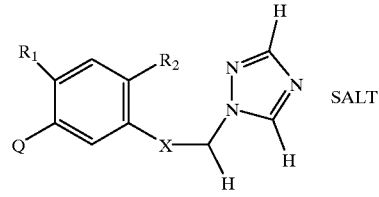

where $R_3 = R_4 = R_5 = H$, $A = B = N$, $R_{10} = CH_3$
in a compound of formula I

| No | $R_1$ | $R_2$ | X | Q | Salt |
|---|---|---|---|---|---|
| 1939 | Cl | Cl | $CO_2$ | Q12 | HCl |
| 1940 | Cl | Cl | $CH_2CH(Cl)CO_2$ | Q12 | HCl |
| 1941 | Cl | Cl | $CH{=}C(Cl)CO_2$ | Q12 | HCl |

TABLE 25

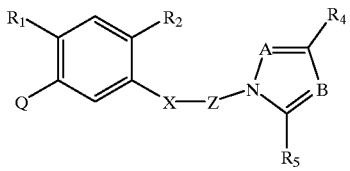

where $R_{10} = CH_3$ when Q is Q12 in a compound of formula I

| No | $R_1$ | $R_2$ | X | Z | $R_4$ | $R_5$ | Q | A | B |
|---|---|---|---|---|---|---|---|---|---|
| 1942 | F | Cl | NH | CO | H | H | Q1 | N | N |
| 1943 | F | Cl | NH | CO | $CH_3$ | $CH_3$ | Q1 | N | N |
| 1944 | F | Cl | NH | CO | H | $SCH_3$ | Q1 | N | N |
| 1945 | F | Cl | NH | CO | H | $CO_2CH_3$ | Q1 | N | N |
| 1946 | F | Cl | NH | CO | Ph-4-Cl | H | Q1 | N | N |
| 1947 | F | Cl | NH | CO | $CH_3$ | $CO_2CH_3$ | Q1 | N | N |
| 1948 | F | Cl | NH | CO | H | H | Q1 | N | CH |
| 1949 | F | Cl | NH | CO | $CH_3$ | $CH_3$ | Q1 | N | $CCO_2CH_3$ |
| 1950 | F | Cl | NH | CO | Cl | Cl | Q1 | N | $CCONMe_2$ |
| 1951 | F | Cl | NH | CO | $C_2H_5$ | $CO_2CH_3$ | Q1 | N | CH |
| 1952 | F | Cl | NH | CO | $CH_3$ | CONHPh | Q1 | N | CH |
| 1953 | F | Cl | NH | CO | Ph-4-Cl | $CO_2NMe_2$ | Q1 | N | CCl |
| 1954 | F | Cl | NH | CO | H | H | Q1 | CH | N |
| 1955 | F | Cl | $NSO_2CH_3$ | CO | H | H | Q1 | N | N |
| 1956 | F | Cl | $NSO_2CH_3$ | CO | H | H | Q1 | N | CH |
| 1957 | F | CN | $NSO_2CH_3$ | CO | H | H | Q1 | CH | N |
| 1958 | F | Cl | $NSO_2CF_3$ | CO | H | H | Q1 | N | N |
| 1959 | F | CN | $NSO_2CF_3$ | CO | H | H | Q1 | N | CH |
| 1960 | F | Cl | $NSO_2CF_3$ | CO | H | H | Q1 | CH | N |
| 1961 | F | Cl | $NSO_2CH_3$ | $CH_2$ | H | H | Q1 | N | N |
| 1962 | F | Cl | $NSO_2CH_3$ | $CH_2$ | H | H | Q1 | N | CH |
| 1963 | F | Cl | $NSO_2CH_3$ | $CH_2$ | H | H | Q1 | CH | N |
| 1964 | F | Cl | $NSO_2CF_3$ | $CH_2$ | H | H | Q1 | N | N |
| 1965 | F | Cl | $NSO_2CF_3$ | $CH_2$ | H | H | Q1 | N | CH |
| 1966 | F | Cl | $NSO_2CF_3$ | $CH_2$ | H | H | Q1 | CH | N |
| 1967 | F | Cl | $NSO_2CH_3$ | CO | H | H | Q2 | N | N |
| 1968 | F | CN | $NSO_2CH_3$ | CO | H | H | Q2 | N | CH |
| 1969 | F | Cl | $NSO_2CH_3$ | CO | H | H | Q2 | CH | N |
| 1970 | F | Cl | $NSO_2CF_3$ | CO | H | H | Q2 | N | N |
| 1971 | F | Cl | $NSO_2CF_3$ | CO | H | H | Q2 | N | CH |
| 1972 | F | CN | $NSO_2CF_3$ | CO | H | H | Q2 | CH | N |
| 1973 | F | Cl | $NSO_2CH_3$ | $CH_2$ | H | H | Q2 | N | N |
| 1974 | F | Cl | $NSO_2CH_3$ | $CH_2$ | H | H | Q2 | N | CH |
| 1975 | F | Cl | $NSO_2CH_3$ | $CH_2$ | H | H | Q2 | CH | N |
| 1976 | F | Cl | $NSO_2CF_3$ | $CH_2$ | H | H | Q2 | N | N |
| 1977 | F | CN | $NSO_2CF_3$ | $CH_2$ | H | H | Q2 | N | CH |

TABLE 25-continued

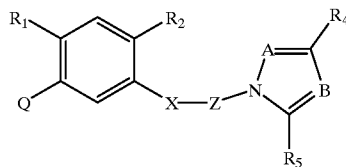

where $R_{10}$ = $CH_3$ when Q is Q12 in a compound of formula I

| No | $R_1$ | $R_2$ | X | Z | $R_4$ | $R_5$ | Q | A | B |
|---|---|---|---|---|---|---|---|---|---|
| 1978 | F | Cl | $NSO_2CF_3$ | $CH_2$ | H | H | Q2 | CH | N |
| 1979 | F | CN | $NSO_2CH_3$ | CO | H | H | Q3 | N | CH |
| 1980 | F | Cl | $NSO_2CF_3$ | CO | H | H | Q3 | CH | N |
| 1981 | F | Cl | $NSO_2CF_3$ | CO | H | H | Q3 | N | N |
| 1982 | F | Cl | $NSO_2CH_3$ | $CH_2$ | H | H | Q3 | N | N |
| 1983 | F | Cl | $NSO_2CH_3$ | $CH_2$ | H | H | Q3 | N | CH |
| 1984 | F | Cl | $NSO_2CH_3$ | $CH_2$ | H | H | Q3 | CH | N |
| 1985 | F | Cl | $NSO_2CH_3$ | CO | H | H | Q7 | N | CH |
| 1986 | F | Cl | $NSO_2CH_3$ | CO | H | H | Q7 | CH | N |
| 1987 | F | Cl | $NSO_2CH_3$ | CO | H | H | Q7 | N | N |
| 1988 | F | Cl | $NSO_2CH_3$ | $CH_2$ | H | H | Q7 | N | N |
| 1989 | F | Cl | $NSO_2CH_3$ | $CH_2$ | H | H | Q7 | N | CH |
| 1990 | F | Cl | $NSO_2CH_3$ | $CH_2$ | H | H | Q7 | CH | N |
| 1991 | F | Cl | $NSO_2CH_3$ | CO | H | H | Q8 | N | N |
| 1992 | F | Cl | $NSO_2CH_3$ | CO | H | H | Q8 | CH | N |
| 1993 | F | Cl | $NSO_2CH_3$ | CO | H | H | Q8 | N | CH |
| 1994 | F | Cl | $NSO_2CF_3$ | CO | H | H | Q8 | N | N |
| 1995 | F | Cl | $NSO_2CF_3$ | CO | H | H | Q8 | CH | N |
| 1996 | F | Cl | $NSO_2CF_3$ | CO | H | H | Q8 | N | CH |
| 1997 | F | Cl | $NSO_2Et$ | CO | $CH_3$ | $CH_3$ | Q8 | N | N |
| 1998 | F | Cl | $NSO_2Et$ | CO | $CH_3$ | $CH_3$ | Q8 | CH | N |
| 1999 | F | Cl | $NSO_2Et$ | CO | $CH_3$ | $CH_3$ | Q8 | N | CH |
| 2000 | Cl | Cl | $NSO_2CH_3$ | CO | H | H | Q8 | N | N |
| 2001 | Cl | Cl | $NSO_2CH_3$ | CO | H | H | Q8 | CH | N |
| 2002 | Cl | Cl | $NSO_2CH_3$ | CO | H | H | Q8 | N | CH |
| 2003 | Cl | Cl | $NSO_2CF_3$ | CO | H | H | Q8 | N | N |
| 2004 | Cl | Cl | $NSO_2CF_3$ | CO | H | H | Q8 | CH | N |
| 2005 | Cl | Cl | $NSO_2CF_3$ | CO | H | H | Q8 | N | CH |
| 2006 | Cl | Cl | $NSO_2Et$ | CO | $CH_3$ | $CH_3$ | Q8 | N | N |
| 2007 | Cl | Cl | $NSO_2Et$ | CO | $CH_3$ | $CH_3$ | Q8 | CH | N |
| 2008 | Cl | Cl | $NSO_2Et$ | CO | $CH_3$ | $CH_3$ | Q8 | N | CH |
| 2009 | F | Cl | $CH_2C(Cl)$ | CO | H | H | Q8 | N | N |
| 2010 | F | Cl | $CH_2C(Cl)$ | CO | H | H | Q8 | CH | N |
| 2011 | F | Cl | $CH_2C(Cl)$ | CO | H | H | Q8 | N | CH |
| 2012 | F | Cl | $CH_2C(Cl)$ | CO | H | H | Q1 | N | N |
| 2013 | F | Cl | $CH_2C(Cl)$ | CO | H | H | Q1 | CH | N |
| 2014 | F | Cl | $CH_2C(Cl)$ | CO | H | H | Q1 | N | CH |
| 2015 | H | Cl | $CH=C(Cl)$ | CO | H | H | Q1 | N | N |
| 2016 | F | Cl | $OCH_2$ | CO | H | H | Q1 | N | N |
| 2017 | F | Cl | $SCH_2$ | CO | H | H | Q3 | N | N |
| 2018 | F | Cl | $CH_2C(Cl)$ | CO | H | H | Q10 | N | CH |
| 2019 | H | Cl | $CH=C(Cl)$ | CO | H | H | Q10 | N | N |
| 2020 | F | Cl | $OCH_2$ | CO | H | H | Q10 | N | N |
| 2021 | F | Cl | $SCH_2$ | CO | H | H | Q10 | N | N |
| 2022 | F | Cl | $CH_2C(Cl)$ | CO | H | H | Q11 | N | CH |
| 2023 | H | Cl | $CH=C(Cl)$ | CO | H | H | Q11 | N | N |
| 2024 | F | Cl | $OCH_2$ | CO | H | H | Q11 | N | N |
| 2025 | F | Cl | $SCH_2$ | CO | H | H | Q11 | N | N |
| 2026 | F | Cl | $CH_2C(Cl)$ | CO | H | H | Q12 | N | CH |
| 2027 | H | Cl | $CH=C(Cl)$ | CO | H | H | Q12 | N | N |
| 2028 | F | Cl | $OCH_2$ | CO | H | H | Q12 | N | N |
| 2029 | F | Cl | $SCH_2$ | CO | H | H | Q12 | N | N |
| 2030 | F | Cl | $CH_2C(Cl)$ | CO | H | H | Q16 | N | CH |
| 2031 | H | Cl | $CH=C(Cl)$ | CO | H | H | Q16 | N | N |
| 2032 | F | Cl | $OCH_2$ | CO | H | H | Q16 | N | N |
| 2033 | F | Cl | $SCH_2$ | CO | H | H | Q16 | N | N |
| 2034 | F | Cl | $NSO_2CH_3$ | CO | H | H | Q7 | N | N |
| 2035 | F | Cl | $NSO_2CH_3$ | CO | H | H | Q10 | N | N |
| 2036 | F | Cl | $NSO_2CH_3$ | CO | H | H | Q11 | N | N |
| 2037 | F | Cl | $NSO_2CH_3$ | CO | H | H | Q12 | N | N |
| 2038 | F | Cl | $NSO_2CH_3$ | CO | H | H | Q16 | N | N |
| 2039 | F | Cl | $NSO_2CH_3$ | $CH_2$ | H | H | Q7 | N | N |
| 2040 | F | Cl | $NSO_2CH_3$ | $CH_2$ | H | H | Q10 | N | N |
| 2041 | F | Cl | $NSO_2CH_3$ | $CH_2$ | H | H | Q11 | N | N |
| 2042 | F | Cl | $NSO_2CH_3$ | $CH_2$ | H | H | Q12 | N | N |

TABLE 25-continued

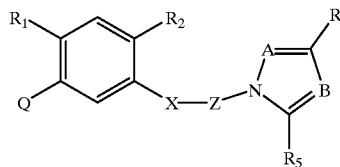

where $R_{10} = CH_3$ when Q is Q12 in a compound of formula I

| No | $R_1$ | $R_2$ | X | Z | $R_4$ | $R_5$ | Q | A | B |
|---|---|---|---|---|---|---|---|---|---|
| 2043 | F | Cl | $NSO_2CH_3$ | $CH_2$ | H | H | Q16 | N | N |
| 2044 | Cl | Cl | $NSO_2CH_3$ | CO | H | H | Q7 | N | N |
| 2045 | Cl | Cl | $NSO_2CH_3$ | CO | H | H | Q10 | N | N |
| 2046 | Cl | Cl | $NSO_2CH_3$ | CO | H | H | Q11 | N | N |
| 2047 | Cl | Cl | $NSO_2CH_3$ | CO | H | H | Q12 | N | N |
| 2048 | Cl | Cl | $NSO_2CH_3$ | CO | H | H | Q16 | N | N |
| 2049 | Cl | Cl | $NSO_2CH_3$ | $CH_2$ | H | H | Q7 | N | N |
| 2050 | Cl | Cl | $NSO_2CH_3$ | $CH_2$ | H | H | Q10 | N | N |
| 2051 | Cl | Cl | $NSO_2CH_3$ | $CH_2$ | H | H | Q11 | N | N |
| 2052 | Cl | Cl | $NSO_2CH_3$ | $CH_2$ | H | H | Q12 | N | N |
| 2053 | Cl | Cl | $NSO_2CH_3$ | $CH_2$ | H | H | Q16 | N | N |
| 2054 | H | Cl | $NSO_2CH_3$ | CO | H | H | Q7 | N | N |
| 2055 | H | Cl | $NSO_2CH_3$ | CO | H | H | Q10 | N | N |
| 2056 | H | Cl | $NSO_2CH_3$ | CO | H | H | Q11 | N | N |
| 2057 | H | Cl | $NSO_2CH_3$ | CO | H | H | Q12 | N | N |
| 2058 | H | Cl | $NSO_2CH_3$ | CO | H | H | Q16 | N | N |
| 2059 | H | Cl | $NSO_2CH_3$ | $CH_2$ | H | H | Q7 | N | N |
| 2060 | H | Cl | $NSO_2CH_3$ | $CH_2$ | H | H | Q10 | N | N |
| 2061 | H | Cl | $NSO_2CH_3$ | $CH_2$ | H | H | Q11 | N | N |
| 2062 | H | Cl | $NSO_2CH_3$ | $CH_2$ | H | H | Q12 | N | N |
| 2063 | H | Cl | $NSO_2CH_3$ | $CH_2$ | H | H | Q16 | N | N |
| 2064 | H | Cl | $NSO_2CH_3$ | CO | H | H | Q8 | N | N |
| 2065 | H | Cl | $NSO_2CH_3$ | CO | H | H | Q8 | CH | N |
| 2066 | H | Cl | $NSO_2CH_3$ | CO | H | H | Q8 | N | CH |
| 2067 | H | Cl | $NSO_2CF_3$ | CO | H | H | Q8 | N | N |
| 2068 | H | Cl | $NSO_2CF_3$ | CO | H | H | Q8 | CH | N |
| 2069 | H | Cl | $NSO_2CF_3$ | CO | H | H | Q8 | N | CH |
| 2070 | H | Cl | $NSO_2Et$ | CO | $CH_3$ | $CH_3$ | Q8 | N | N |
| 2071 | H | Cl | $NSO_2Et$ | CO | $CH_3$ | $CH_3$ | Q8 | CH | N |
| 2072 | H | Cl | $NSO_2Et$ | CO | $CH_3$ | $CH_3$ | Q8 | N | CH |

The compounds of formula I of the present invention can be prepared by the following processes:

Scheme 1

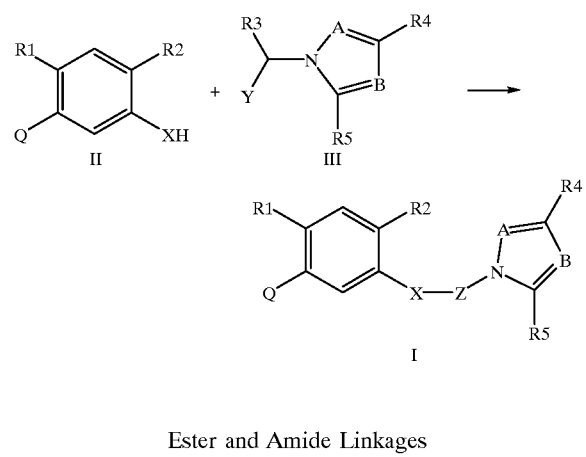

Ester and Amide Linkages

For structure II and III, where X is for example $CO_2$, $OCH(R_6)CO_2$, $SCH(R_6)CO_2$, $CH_2CH(Cl)CO_2$, $CH=C(Cl)CO_2$ and Y is for example OH, $NH_2$:

Compounds II or their sodium, potassium salts are reacted with the one of the following regents: $SOCl_2$, $(COCl)_2$, $COCl_2$, $PCl_3$ or $POCl_3$ in a solvent such as chloroform, dichloromethane, carbon tetrachloride, hexane, benzene, toluene, tetrahydrofuran, dioxane, acetone or methyl ethyl ketone to yield an acid chloride. This acid chloride then reacted with intermediate III, (optionally in the presence of the bases such as $Et_3N$, pyridine, NaOH, KOH, $Na_2CO_3$, $K_2CO_3$, $NaHCO_3$) at a temperature from $-40°$ C. to the boiling point of the solvent for 3 minutes to 8 hours to afford the final product I.

Intermediate II may be obtained from the ester (made by known methods such as those described in EP 0 083 055 A2) by reacting with $K_2CO_3$, NaOH, or KOH in ethanol, then with an inorganic acid such as hydrochloric acid.

Intermediate III (where $R_3$ is alkyl) may be obtained from the known reactions of an aldehyde with IV in the presence or absence of ammonium hydroxide.

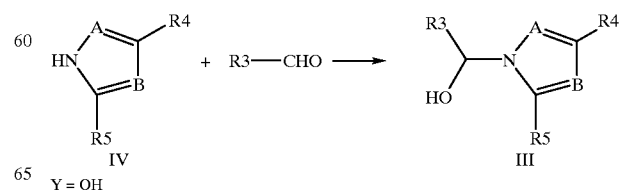

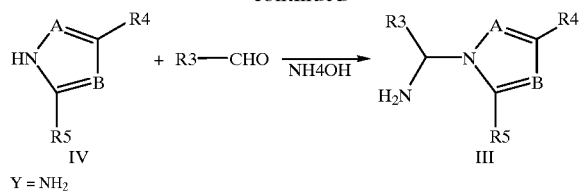

Y = NH$_2$

Ether, Thioether, Amine Linkages

For structure II (where X is O, S, NH) and structure III (where Y=Cl, OSO$_2$CH$_3$, etc.), compounds II are reacted with the intermediates III in the presence of bases such as Et$_3$N, pyridine, NaOH, KOH, Na$_2$CO$_3$, K$_2$CO$_3$, NaHCO$_3$, NaH, NaOCH$_3$, NaOC$_2$H$_5$, in a solvent such as tetrahydrofuran, dioxane, acetone, methyl ethyl ketone, acetonitrile, N,N-dimethylformamide at a temperature from −40° C. to the boiling point of the solvent for 30 minutes to 18 hours to afford the final product I.

Scheme 2

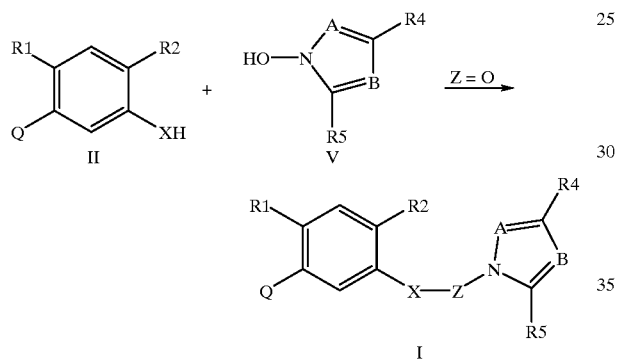

For structure II where X is for example CO$_2$, OCH(R$_6$)CO$_2$, SCH(R$_6$)CO$_2$, CH$_2$CH(Cl)CO$_2$ or CH=C(Cl)CO$_2$:

Compounds II or their sodium, potassium salts are reacted with the one of the following regents: SOCl$_2$, (COCl)$_2$, COCl$_2$, POCl$_3$ or POCl$_3$ in a solvent such as chloroform, dichloromethane, carbon tetrachloride, hexane, benzene, toluene, tetrahydrofuran, dioxane, acetone or methyl ethyl ketone to yield an acid chloride. This acid chloride then reacted with intermediate V, (optionally in the presence of the bases such as Et$_3$N, pyridine, NaOH, KOH, Na$_2$CO$_3$, K$_2$CO$_3$ or NaHCO$_3$) at a temperature from −40° C. to the boiling point of the solvent for 3 minutes to 8 hours to afford the final product I.

Intermediates V were prepared by known methods, for example see EP 0 567 827 A1.

Scheme 3

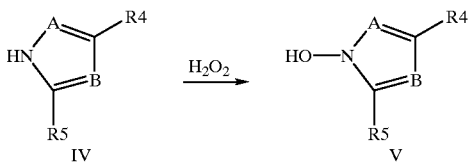

The preparation of the salts of formula I, for example, is straightforward as shown:

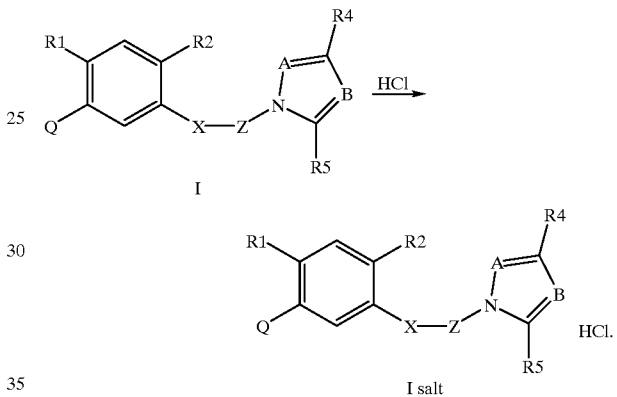

The salts of formula I can be prepared from I in ethanol or other solvent with HCl, CH$_3$CO$_2$H, H$_3$PO$_4$, HO$_2$CCO$_2$H etc. or other acids.

The present invention now will be described in further detail with reference to Examples in order to further guide its practitioner. However, it should be understood that the present invention is by no means restricted by these specific Examples.

PREPARATION EXAMPLE A (COMPOUND NO. 15)

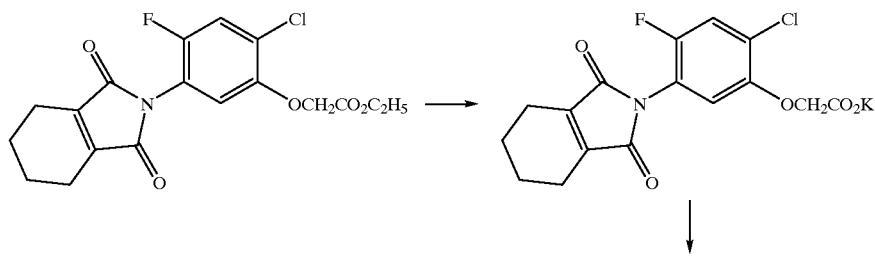

-continued

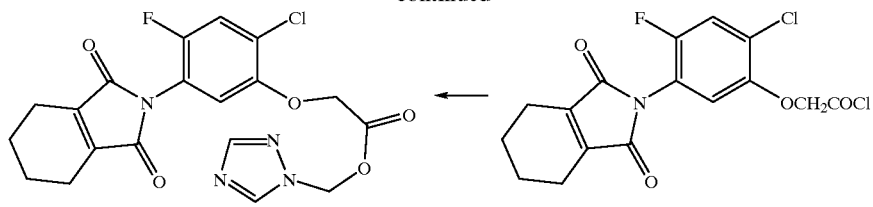

2-(4-Chloro-2-fluoro-5-ethoxycarbonylmethoxyphenyl)-4,5,6,7-tetrahydro-2H-isoindole-1,3-dione (4.0 g, made substantially by the methods described in EP 0 083 055 A2) and KOH (85%, 2.1 g) in 50 ml ethanol were stirred at room temperature for 1 hour and then evaporated to dryness. To the residue was added 100 ml chloroform and 8 ml $SOCl_2$. The reaction mixture was then heated to reflux for 2 hours. Potassium chloride was filtered and washed with fresh chloroform. The filtrate was evaporated to dryness. To the residue was added 50 ml chloroform and 1.5 g 1-hydroxymethyl-(1H)-1,2,4-triazole. The reaction mixture was then stirred at room temperature for 5 hours. Water was added to the mixture, the organic layer was separated and washed with water and brine, dried and concentrated. The residue was purified by silica gel column chromatography to give 2.1 g of 2-(4-chloro-2-fluoro-5-[(1,2,4-triazolylmethoxy)carbonylmethoxy]phenyl)-4,5,6,7-tetrahydro-2H-isoindole-1,3-dione (Compound No. 15). M.P. 151–154° C.

PREPARATION EXAMPLE B (COMPOUND NO. 43)

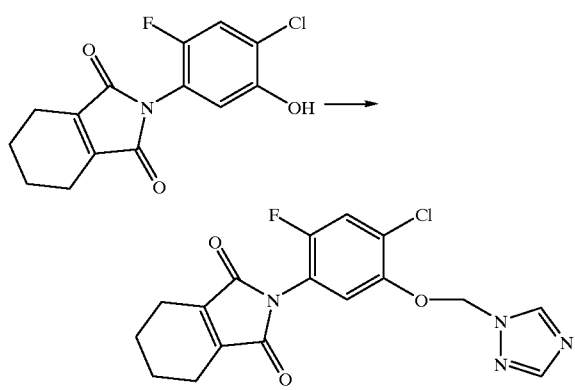

2-(4-Chloro-2-fluoro-5-hydroxyphenyl)-4,5,6,7-tetrahydro-2H-isoindole-1,3-dione (4.0 g, made by substantially following the methods of EP 0 083 055 A2), $K_2CO_3$ in 50 ml methyl ethyl ketone and 2.0 g chloromethyl-1,2,4-triazole hydrochloride and then the mixture were heated to reflux for 5 hrs. After cooling the mixture was filtered and evaporated. Water and ethyl acetate were added to the residue. The organic layer was separated and washed with water and brine, dried and concentrated. The residue was purified by silica gel column chromatography to give 2.6 g of 2-[4-chloro-2-fluoro-5-[(1,2,4-triazol-1H-yl)methoxy]phenyl] -4,5,6,7-tetrahydro-2H-isoindole-1,3-dione (Compound No. 43) as an oil.

$^1$H NMR ($CDCl_3$): 8.32(s,1H), 8.01(s,1H), 7.28(d,2H), 7.06(d,2H), 6.04(s,2H), 2.44(bs,4H), 1.83(bs,4H).

PREPARATION EXAMPLE C (COMPOUND NO. 1334)

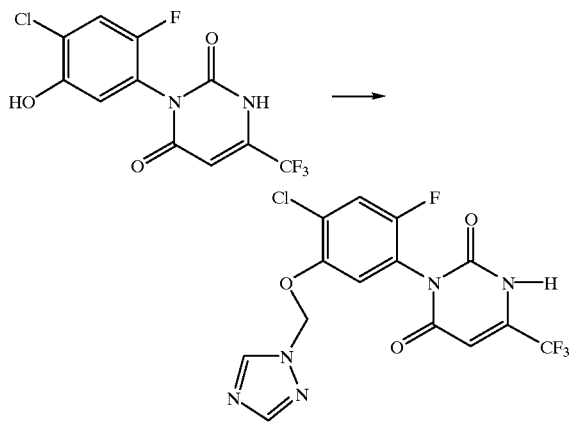

To a suspension of 60% NaH(0.5 g) in 5 ml N,N-dimethylformamide was added 0.8 g of 3-[4-chloro-2-fluoro-5-hydroxyphenyl]-6-trifluoromethyl-2,4-pyrimidione (made by substantially following the methods of EP 0 255 047 A1). After 10 minutes, 0.8 g chloromethyl-1,2,4-triazole hydrochloride was added and then the mixture was heated at the bath of 80° C. for 8 hrs. After cooling, water and ethyl acetate were added to the mixture. The organic layer was separated and washed with water and brine, dried and concentrated. The residue was purified by silica gel column chromatography to give 0.75 g of 3-[4-chloro-2-fluoro-5-[(1,2,4-triazol-1H-yl)-methoxy]phenyl]-6-trifluoromethyl-2,4-pyrimidione (compound 1334), mp. 216–219° C.

$^1$H NMR (acetone-$D_6$): 8.64(s,1H), 7.96(s,1H), 7.55(d, 2H), 7.52(d,2H), 6.36(s,1H), 6.27(s,2H).

PREPARATION EXAMPLE D (COMPOUND NO. 1335)

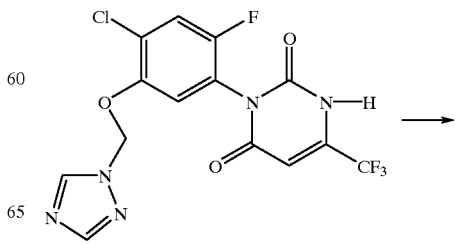

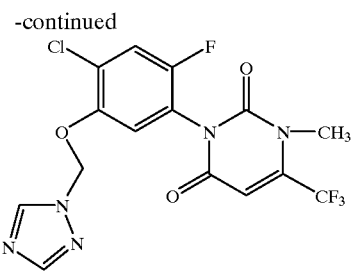

To a suspension of 60% NaH(0.08 g) in 5 ml N,N-dimethylformamide was added 0.5 g of 3-[4-chloro-2-fluoro-5-[(1,2,4-triazol-1H-yl)-methoxy]-phenyl]-6-trifluoromethyl-2,4-pyrimidione (compound 1334). After 10 minutes, 0.2 g of dimethyl sulfate was added and then the mixture was stirred at room temperature overnight. Water and ethyl acetate were added to the mixture. The organic layer was separated and washed with water and brine, dried and concentrated. The residue was purified by silica gel column chromatography to give 0.2 g of 1-methyl-3-[4-chloro-2-fluoro-5-[(1,2,4-triazol-1H-yl)methoxy]phenyl]-6-trifluoromethyl-2,4-pyrimidione (compound 1335).

$^1$H NMR (CDCl$_3$): 8.31(s,1H), 7.98(s,1H), 7.36(d,2H), 7.07(d,2H), 6.60(s,1H), 6.06(s,2H), 4.00(s,3H).

PREPARATION EXAMPLE E (COMPOUND NO. 1870)

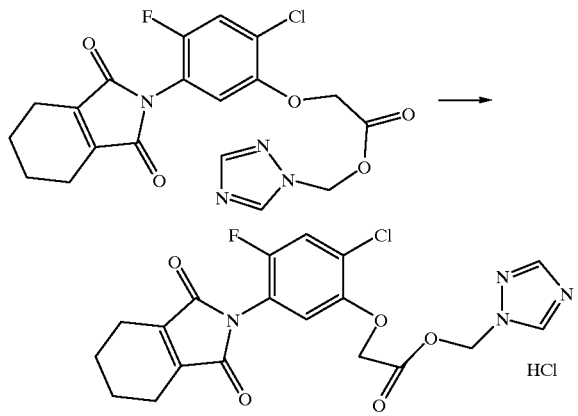

2-[4-Chloro-2-fluoro-5-[(1,2,4-triazol-1H-yl)-methoxy]phenyl]-4,5,6,7-tetrahydro-2H-isoindole-1,3-dione (2.0 g) and hydrochloride acid (36%, 0.7 g) in 20 ml ethanol were stirred at room temperature for 10 minutes and then evaporated to dryness. To the residue was added 5 ml acetone and the mixture was filtered and dried to obtain 1.6 g of the hydrochloride salt of 2-[4-chloro-2-fluoro-5-[(1,2,4-triazol-1H-yl)methoxy]phenyl]-4,5,6,7-tetrahydro-2H-isoindole-1,3-dione (Compound No. 1870) as a solid.

$^1$H NMR (DMSO-D$_6$, 300 MHz): 8.79(s,1H), 8.12(s,1H), 7.70(d,1H), 7.28(d,1H), 6.25(s,2H), 4.96(s,2H), 2.36(bs, 4H), 1.75(bs,4H).

The compounds of formula I are useful as an active ingredient for herbicides. When the compound of formula I of the present invention is used as a herbicide, the active ingredient can be used in a suitable formulation depending upon the particular purpose and by a suitable application method. Usually, the active ingredient is diluted with an inert liquid or solid carrier, and used in the form of a formulation such as a dust, a wettable powder, an emulsifiable concentrate, aqueous or oil suspension, pellets, granules, etc., If desirable one may also add a surfactant and/or other additive. Furthermore, one of ordinary skill in the art will recognize that the compound of the present invention may be used in combination with an insecticide, a nematocide, a fungicide, other herbicides, a plant growth controlling agent, a fertilizer, etc.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined. Compositions and formulations according to the present invention may also include known pesticidal compounds. This expands the spectrum of activity of the preparation and may give rise to synergism.

The formulations, contain from about 0.1% to 99% by weight of active ingredient(s) and at least one of (a) about 0.1% to 20% surfactant(s) and (b) about 1% to 99.9% solid or liquid diluent(s).

If the compound of formula(I) is formulated with an additional herbicide, the concentration of active ingredient (s) in the compositions can vary within a wide range, depending on the active compound, the applications for which they are destined, the environmental conditions and the kind of formulation. The concentration of active ingredient(s) in the compositions is generally between 1% to 95%, preferably between 5% to 60%.

The formulations now will be described in detail with reference to typical Formulation Examples and do not limit the scope of this invention. In the following Formulation Examples, "parts" means "parts by weight". The compound number of the active ingredient corresponds to the one in Tables 1–24.

FORMULATION EXAMPLES 1a–c

Compound No. 1, 15 or 43 (all 50 parts), 5 parts of polyoxyethylene alkylaryl ether, 5 parts of sodium dodecylbenzenesulfate and 40 parts of synthetic hydrated silicon dioxide are well mixed while being powdered in order to obtain a 50% wettable powder.

FORMULATION EXAMPLE 2

Compound No. 35 (10 parts), 6 parts of polyoxyethylene alkylaryl ether, 4 parts of sodium dodecylbenzenesulfate, 30 parts of xylene and 50 parts of cyclohexanone are well mixed while being powdered in order to obtain a 10% by weight emulsifiable concentrate.

FORMULATION EXAMPLE 3

Compound No. 15 (20 parts), 2 parts of synthetic hydrated silicon dioxide, 3 parts of polyoxyethylene sorbitan monooleate, 5 parts of carboxymethyl cellulose and 70 parts of water are well mixed and pulverized until the particle size of the active ingredient becomes less than 5 microns in order to obtain a 20% by weight granule.

FORMULATION EXAMPLE 4

Compound No. 15 (5 parts), 1 part of isopropyl acid phosphate, 64 parts of kaolin clay and 30 parts of talc are well mixed and pulverized until the particle size of the active ingredient becomes less than 5 microns in order to obtain a 5% by weight dust.

FORMULATION EXAMPLE 5

Compound No. 15 (25 parts), 3 parts of polyoxyethylene sorbitan monooleate, 2 parts of polyvinyl alcohol and 70 parts of water are well mixed and pulverized until the particle size of the active ingredient becomes less than 5 microns in order to obtain a 25% an aqueous suspension.

The effective dose of the compounds of the present invention is usually within a range of from 1 g/ha to 3 kg/ha, preferably from 5 g/ha to 500 g/ha.

Biological Testing

The herbicidal activity of compounds of formula (I) with respect to weeds such as *Bidens pilosa* (beggartick, BID), *Solanum nigrum* (nightshade, NS), *Polygonum lapathifolium* (smartweed, SMT), *Abutilon theophrasti* (velvetleaf, VEL) was evaluated.

For each compounds, the evaluation tests were carried out according to the following operating procedures.

For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of development. The test plants were selected for uniformity, size and stage of development. The test plants were then treated with the test compound, returned to the greenhouse and watered. The plants not treated with the compound under evaluation were used as a comparison.

The compound to be evaluated was dissolved in an appropriate solvent, usually acetone, or the formulation of the evaluated compounds was added to the water, and sprayed over the flats or pots using a carrier volume equivalent to 187 or 468 liters per hectare at the rate of application in grams per hectare (g/ha). About two or four week s after application of the test compounds, the state of the plant was observed. Each species was evaluated on a scale of 0–100 in which 0 equals no activity and 100 equals total control. Some of the test results are shown in Table 26.

TABLE 26

| Compound | Type | g/ha | BID | NS | SMT | VEL |
|---|---|---|---|---|---|---|
| 15 | POST | 150 | 60 | 100 | 40 | 100 |
| 43 | POST | 1200 | 100 | 100 | 100 | 100 |

We claim:
1. A compound represented by formula I

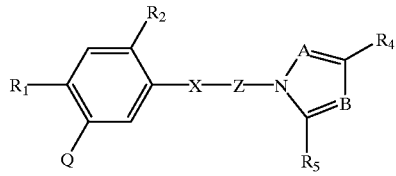

wherein
$R_1$ is selected from H, F, Br, Cl, $NO_2$ and CN;
$R_2$ is selected from F, Cl, Br, H and CN;
$R_3$ is selected from H and CN; and alkyl, alkenyl, alkynyl, haloalkyl, cycloalkyl, cycloalkanyl, haloalkenyl, haloalkynyl, alkoxy, alkylthio, alkylsulfonylalkyl, alkylsulfinylalkyl, alkylsulfonylcycloalkyl, alkylsulfinylcycloalkyl, aryl, arylalkyl, heteroaryl and heteroarylalkyl, all of which may be further substituted;
$R_4$ and $R_5$ are each independently selected from H, halo and CN; and alkyl, cycloalkyl, haloalkyl, alkoxy, alkylthio, alkylsulfonylalkyl, alkylsulfinylalkyl, alkylsulfonylcycloalkyl, alkylsulfinylcycloalkyl, $CO_2R_6$, $CONR_6R_{13}$, $OR_6$, $SR_6$, $SO_2R_6$, $NR_6R_{13}$, $SO_2NR_6R_{13}$, aryl, arylalkyl, heteroaryl and heteroarylalkyl, all of which may be further substituted;
$R_6$ is selected from H, alkyl, cycloalkyl, alkoxy, alkylthio, alkylsulfonylalkyl, alkylsulfinylalkyl, alkylsulfinylcycloalkyl, alkylsulfinylcycloalkyl, aryl and arylalkyl, all of which may be further substituted;
$R_7$ is selected from H, alkyl, alkenyl, alkynyl, haloalkyl, cycloalkyl, alkylsulfonylalkyl, alkylsulfinylalkyl, alkylsulfonylcycloalkyl, alkylsulfinylcycloalkyl and $COR_9$, all of which may be further substituted;
$R_8$ is selected from alkyl, haloalkyl, cycloalkyl, cycloalkenyl, alkylsulfonylalkyl, alkylsulfinylalkyl, alkylsulfonylcycloalkyl, alkylsulfinylcycloalkyl, aryl and arylalkyl;
$R_9$ is selected from H, alkyl, alkylsulfonylalkyl, alkylsulfinylalkyl, alkylsulfonylcycloalkyl, alkylsulfinylcycloalkyl, alkenyl, alkynyl, haloalkyl and cycloalkyl, all of which may be further substituted;
$R_{10}$ is selected from H, halo, $NH_2$, alkyl, alkylsulfonylalkyl, alkylsulfinylalkyl, alkylsulfonylcycloalkyl, alkylsulfinylcycloalkyl, haloalkyl, CN, $CO_2$(alkyl), CONH(alkyl), CON(alkyl)$_2$ wherein each alkyl may be the same or different, $CH_3CN$, $CH_2CH=CH_2$, $CH_2C\equiv CH$, $CH_2CO_2$(alkyl), $CH_2OCH_3$ and $CH_2$-1,2,4triazole, all of which may be further substituted;
$R_{11}$ is selected from H, CN, alkyl, haloalkyl and $CO_2$(alkyl);
$R_{12}$ is selected from H, alkyl, $CO_2R_6$, $CONR_6R_{13}$, $OR_6$, $SR_6$, $SO_2R_6$, $SO_3NR_6R_{13}$ and $NR_6R_{13}$;
$R_{13}$ is H, alkyl, aryl or arylalkyl;
A is N;
B is N;
Z is O, $CH(R_3)$, CO, CS, $CONR_{12}$ or $CSNR_{12}$;
X is selected from O, S, $NR_{12}$, $CO_2$, $OCH(R_6)CO_2$, $SCH(R_6)CO_2$, $CH=C$(halo)$CO_2$, $CH_2CH$(halo)$CO_2$, CONH, $OCH(R_6)CONH$, $SCH(R_6)CONH$, $CH=C$(halo)CONH and $CH_2CH$(halo)CONH when Z is $CH(R_3)$;

X is selected from CO, OCH($R_6$)CO, SCH($R_6$)CO, CH=C(halo)CO and $CH_2$CH(halo)CO when Z is O;

X is selected from O, S, CO, OCH($R_6$), CH=C(halo), $CH_2$CH(halo), CONH, OCH($R_6$)CONH, SCH($R_6$)CONH, CH=C(halo)CONH, $CH_2$CH(halo)CONH and $NR_{12}$ when Z is CO, CS, $CONR_{12}$ or $CSNR_{12}$; and Q is selected from $NR_7COR_8$, Q2, Q3, Q4, Q5, Q6, Q7, Q8, Q9, Q10, Q11, Q12, Q13, Q14, Q15 and Q16 wherein Q2 is 5,6,7,8-tetrahydro-1,2,4-triazolo[4,3-a]pyridin-3(2H)-one-1-yl, Q3 is 5,6,7,8-tetrahydro-1H,3H-[1,3,4]thiadiazolo[3,5-a]pyridazineimin-1-yl, Q4 is 4,3,5,6,7-tetrahydroimidazo[1,5-a]pyridine-1,3(2H, 5H)-dione-2yl, Q5 is 1,6,8-triazabicyclo[4,3,0]-nonane-7,9-dion-8-yl, Q6 is 5-(1-methyethylidene)-2,4oxazolidinedione-3-yl, Q7 is 5-(1,1-dimethylethyl)-1,3,4-oxadiazol-2(3H)-one-3-yl, Q8 is 4-difluoromethyl-4,5-dihydro-3-methyl-1,2,4-triazol-5(1H)-one-1-yl, Q9 is 2-methyl-1,2,4-oxadiazolidine-3,5-dione-4-yl, Q10 is 4-chloro-1-methyl-5-difluoromethoxy-1H-pyrazol-3-yl, Q11 is 4-bromo-1-methyl-5-trifluoromethyl-1H-pyrazol-3-yl, Q12 is 1-substituted-6-trifluoromethyl-2,4-pyrimidione-3-yl, Q13 is 1-substituted-6-trifluoromethyl-1,3,5-triazine-2,4-dione-1-yl, Q14 is 4,5-disubstituted-4,5-dihydro-1,2,4-triazine-3(2H)-one-2-yl, Q15 is 4-substituted-1,2,4-triazine-3,5(2H,4H)-dione-2-yl and Q16 is 5-methyl-6-oxo-4-(trifluoromethyl)-6H-pyridazin-1-yl; or the agronomically acceptable salts thereof.

2. The compound of claim 1 wherein $R_1$ is selected from H, F, Br, Cl, $NO_2$ and CN;

$R_2$ is selected from F, Cl, Br, H and CN;

$R_3$ is selected from H, CN and halo; and ($C_1$–$C_{12}$)alkyl, cyclo($C_3$–$C_8$)alkyl, ($C_2$–$C_{12}$)alkenyl, cyclo($C_3$–$C_8$) alkenyl, ($C_2$–$C_{12}$)alkynyl, halo($C_1$–$C_{12}$)alkyl, halo($C_2$–$C_{12}$)alkenyl, halo($C_2$–$C_{12}$)alkynyl, ($C_1$–$C_{12}$) alkoxy, ($C_1$–$C_{12}$)alkylthio, ($C_1$–$C_{12}$)alkylsulfonyl ($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$) alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo ($C_1$–$C_{12}$)alkoxy, halo($C_1$–$C_{12}$)alkylthio, halocyclo ($C_3$–$C_8$)alkyl, aryl, heteroaryl, aryl($C_1$–$C_{12}$)alkyl and heteroaryl($C_2$–$C_{12}$)alkyl, all of which may be further substituted with from one to three substituents independently selected from bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$) alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$) alkylsulfonyl, ($C_1$–$C_{12}$)alkylsulfinyl, phenyl, phen ($C_1$–$C_{12}$)alkyl, phen($C_2$–$C_{12}$)alkenyl, phen($C_2$–$C_{12}$) alkynyl, cyano, halo($C_1$–$C_{12}$)alkoxy, 1,3-dioxalan-2-yl and nitro;

$R_4$ and $R_5$ are each independently selected from H, halo and CN; and ($C_1$–$C_{12}$)alkyl, cyclo($C_3$–$C_8$)alkyl, halo ($C_1$–$C_{12}$)alkyl, ($C_1$–$C_{12}$)alkoxy, ($C_1$–$C_{12}$)alkylthio, ($C_1$–$C_{12}$)alkylsulfonyl ($C_1$–$C_{12}$)alkyl, ($C_1$–$C_{12}$) alkylsulfinyl($C_1$–$C_{12}$)alkyl, ($C_1$–$C_{12}$) alkylsulfonylcyclo($C_3$–$C_8$)alkyl, ($C_1$–$C_{12}$) alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo ($C_1$–$C_{12}$)alkoxy, halo($C_1$–$C_{12}$)alkylthio, halocyclo ($C_3$–$C_8$)alkyl, $CO_2R_6$, $CONHR_6$, CON(($C_1$–$C_{12}$)alkyl) $R_6$, $OR_6$, $SR_6$, $SO_2R_6$, $NHR_6$, N(($C_1$–$C_{12}$)alkyl)$R_6$, $SO_2$N(($C_1$–$C_{12}$)alkyl)$R_6$, aryl, heteroaryl, aryl($C_1$–$C_{12}$) alkyl and heteroaryl($C_2$–$C_{12}$)alkyl, all of which may be further substituted with from one to three substituents independently selected from bromo, chloro, fluoro, ($C_1$–$C_{12}$)alkyl, cyclo($C_3$–$C_8$)alkyl, ($C_2$–$C_{12}$)alkenyl, cyclo($C_3$–$C_8$)alkenyl, ($C_2$–$C_{12}$)alkynyl, halo($C_1$–$C_{12}$) alkyl, halo($C_2$–$C_{12}$)alkenyl, halo($C_2$–$C_{12}$)alkynyl, ($C_1$–$C_{12}$)alkoxy, ($C_1$–$C_{12}$)alkylthio, ($C_1$–$C_{12}$) alkylsulfonyl, ($C_1$–$C_{12}$)alkylsulfinyl, phenyl, phen ($C_1$–$C_{12}$)alkyl phen($C_2$–$C_{12}$)alkenyl, phen($C_2$–$C_{12}$) alkynyl, cyano, halo($C_1$–$C_{12}$)alkoxy, 1,3-dioxalan-2-yl and nitro;

$R_6$, is selected from H, ($C_1$–$C_{12}$)alkyl, ($C_1$–$C_{12}$) alkylsulfonyl($C_1$–$C_{12}$)alkyl, ($C_1$–$C_{12}$)alkylsulfinyl ($C_1$–$C_{12}$)alkyl, ($C_1$–$C_{12}$)alkylsulfonylcyclo($C_3$–$C_8$) alkyl, ($C_1$–$C_{12}$)alkylsulfinylcyclo($C_3$–$C_8$)alkyl, cyano ($C_1$–$C_{12}$)alkoxy, cyano($C_1$–$C_{12}$)alkyl, cyanocyclo ($C_3$–$C_8$)alkyl, halo($C_1$–$C_{12}$)alkoxy, halo($C_1$–$C_{12}$) alkylthio, halocyclo($C_3$–$C_8$)alkyl, aryl and aryl ($C_1$–$C_{12}$)alkyl;

$R_7$ is selected from H, ($C_1$–$C_{12}$)alkyl, cyclo($C_3$–$C_8$)alkyl, halo($C_1$–$C_{12}$)alkyl, ($C_1$–$C_{12}$)alkylsulfonyl($C_1$–$C_{12}$) alkyl, ($C_1$–$C_{12}$)alkylsulfinyl($C_1$–$C_{12}$)alkyl, ($C_1$–$C_{12}$) alkylsulfonylcyclo($C_3$–$C_8$)alkyl, ($C_1$–$C_{12}$) alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo ($C_1$–$C_{12}$)alkoxy, halo($C_1$–$C_{12}$)alkylthio, halocyclo ($C_3$–$C_8$)alkyl and $COR_9$;

$R_8$ is selected from ($C_1$–$C_{12}$)alkyl, cyclo($C_3$–$C_8$)alkyl, cyclo($C_3$–$C_8$)alkenyl, halo($C_1$–$C_{12}$)alkyl, ($C_1$–$C_{12}$) alkylsulfonyl ($C_1$–$C_{12}$)alkyl, ($C_1$–$C_{12}$)alkylsulfinyl ($C_1$–$C_{12}$)alkyl, ($C_1$–$C_{12}$)alkylsulfonylcyclo($C_3$–$C_8$) alkyl, ($C_1$–$C_{12}$)alkylsulfinylcyclo($C_3$–$C_8$)alkyl, cyano ($C_1$–$C_{12}$)alkoxy, cyano($C_1$–$C_{12}$)alkyl, cyanocyclo ($C_3$–$C_8$)alkyl, halo($C_1$–$C_{12}$)alkoxy, halo($C_1$–$C_{12}$) alkylthio, halocyclo($C_3$–$C_8$)alkyl, aryl and aryl ($C_1$–$C_{12}$)alkyl;

$R_9$ is selected from H, ($C_1$–$C_{12}$)alkyl, ($C_2$–$C_{12}$)alkenyl, cyclo($C_3$–$C_8$)alkyl, halo($C_1$–$C_{12}$)alkyl, ($C_1$–$C_{12}$) alkylsulfonyl($C_1$–$C_{12}$)alkyl, ($C_1$–$C_{12}$)alkylsulfinyl ($C_1$–$C_{12}$)alkyl, ($C_1$–$C_{12}$)alkylsulfonylcyclo($C_3$–$C_8$) alkyl, ($C_1$–$C_{12}$)alkylsulfinylcyclo($C_3$–$C_8$)alkyl, cyano ($C_1$–$C_{12}$)alkoxy, cyano($C_1$–$C_{12}$)alkyl, cyanocyclo ($C_3$–$C_8$)alkyl, halo($C_1$–$C_{12}$)alkoxy, halo($C_1$–$C_{12}$) alkylthio and halocyclo($C_3$–$C_8$)alkyl;

$R_{10}$ is selected from H, chloro, $NH_2$, ($C_1$–$C_{12}$)alkyl, halo($C_1$–$C_{12}$)alkyl, CN, ($C_1$–$C_{12}$)alkylsulfonyl ($C_1$–$C_{12}$)alkyl, ($C_1$–$C_{12}$)alkylsulfinyl($C_1$–$C_{12}$)alkyl, ($C_1$–$C_{12}$)alkylsulfonylcyclo($C_3$–$C_8$)alkyl, ($C_1$–$C_{12}$) alkylsulfinylcyclo($C_3$–$C_8$)alkyl, cyano($C_1$–$C_{12}$)alkoxy, cyano($C_1$–$C_{12}$)alkyl, cyanocyclo($C_3$–$C_8$)alkyl, halo ($C_1$–$C_{12}$)alkoxy, halo($C_1$–$C_{12}$)alkylthio, halocyclo ($C_3$–$C_8$)alkyl, $CO_2$($C_1$–$C_{12}$)alkyl, CONH($C_1$–$C_{12}$) alkyl, CON(($C_1$–$C_{12}$)alkyl)$_2$, $CH_2CN$, $CH_2CH=CH_2$, $CH_2C≡CH$, $CH_2CO_2$($C_1$–$C_{12}$)alkyl, $CH_2OCH_3$, $CH_2$-1,2,4-triazole;

$R_{11}$ is selected from H, CN, ($C_1$–$C_{12}$)alkyl, halo($C_1$–$C_{12}$) alkyl and $CO_2$($C_1$–$C_{12}$)alkyl;

$R_{12}$ is selected from H, $(C_1-C_{12})$alkyl, $CO_2R_6$, CON$(((C_1-C_{12})$alkyl$)R_6$, $OR_6$, $SR_6$, $SO_2R_6$, $SO_2N$$((C_1-C_{12})$alkyl$)R_{13}$, and $N((C_1-C_{12})$alkyl$)R_{13}$;

$R_{13}$ is H, $(C_1-C_{12})$alkyl, aryl or aryl$(C_1-C_{12})$alkyl;

A is N;

B is N;

Z is O, $CH(R_3)$, CO, CS, $CONR_{12}$ or $CSNR_{12}$;

X is selected from O, S, $NR_{12}$, $CO_2$, $OCH(R_6)CO_2$, $SCH(R_6)CO_2$, CH=C(Cl)$CO_2$, $CH_2CH(Cl)CO_2$, CONH, $OCH(R_6)$CONH, $SCH(R_6)$CONH, CH=C(Cl)CONH and $CH_2CH(Cl)$CONH when Z is $CH(R_9)$;

X is selected from CO, $OCH(R_6)$CO, $SCH(R_6)$CO, CH=C(Cl)CO, $CH_2CH(Cl)$CO when Z is O;

X is selected from O, S, CO, $OCH(R_6)$, CH=C(Cl), $CH_2CH(Cl)$, CONH, $OCH(R_6)$CONH, $SCH(R_6)$CONH, CH=C(Cl)CONH, $CH_2CH(Cl)$CONH and $NR_{12}$ when Z is CO, CS, $CONR_{12}$ or $CSNR_{12}$;

Q is selected from $NR_7COR_8$, Q2, Q3, Q4, Q5, Q6, Q7, Q8, Q9, Q10, Q11, Q12, Q13, Q14, Q15 and Q16;

or the agronomically acceptable salts thereof.

3. The compound of claim 2 wherein $R_1$ is H, F or Cl;

$R_2$ is Cl;

$R_3$ is selected from H, bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, aryl, heteroaryl, aryl$(C_1-C_{12})$alkyl and heteroaryl$(C_2 C_{12})$alkyl wherein the aryl or heteroaryl group is selected from furan, naphthalene, phenyl, pyrazole, pyridine, pyrimidine, thiophene and triazole, said aryl and heteroaryl group may be further substituted with from one to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_{12})$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl and nitro;

$R_4$ and $R_5$ are each independently selected from H, bromo, chloro, fluoro, CN, $(C_1-C_6)$alkyl, cyclo$(C_5-C_6)$alkyl, halo$(C_1-C_6)$alkyl, $(C_1-C_6)$alkoxy, $(C_1-C_6)$alkylthio, $CO_2R_6CONHR_6$, $CON((C_1-C_{12})$alkyl$)R_6$, $OR_6$, $SR_6$, $SO_2R_6$, $NHR_6$, $N((C_1-C_{12})$alkyl$)R_6$, $SO_2N((C_1-C_{12})$alkyl$)R_6$, aryl, heteroaryl, aryl$(C_1-C_{12})$alkyl and heteroaryl$(C_2-C_{12})$alkyl, wherein the aryl or heteroaryl group is selected from furan, naphthalene, phenyl, pyrazole, pyridine, pyrimidine, thiophene and triazole, said aryl and heteroaryl group may be further substituted with from one to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_{12})$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl and nitro;

$R_6$ is selected from H, $(C_1-C_{12})$alkyl, aryl and aryl$(C_1-C_6)$alkyl, where the aryl group is naphthyl or phenyl;

$R_7$ is selected from H, $(C_1-C_{12})$alkyl, cyclo$(C_3-C_8)$alkyl, halo$(C_1-C_{12})$alkyl and $COR_9$;

$R_8$ is selected from $(C_1-C_{12})$alkyl, cyclo$(C_3-C_8)$alkyl, cyclo$(C_3-C_8)$alkenyl, halo$(C_1-C_{12})$alkyl, aryl and aryl$(C_1-C_6)$alkyl;

$R_9$ is selected from H, $(C_1-C_6)$alkyl, $(C_2-C_{12})$alkenyl, $(C_2-C_6)$alkenyl, cyclo$(C_3-C_8)$alkyl, cyclo$(C_5-C_6)$alkyl, halo$(C_1-C_{12})$alkyl, halo$(C_1-C_6)$alkyl;

$R_{10}$ is selected from H, chloro, $NH_2$, $(C_1-C_6)$alkyl, halo$(C_1-C_{12})$alkyl, halo$(C_1-C_6)$alkyl, CN, $CO_2(C_1-C_{12})$alkyl, $CONH(C_1-C_{12})$alkyl, $CON((C_1-C_{12})$alkyl$)_2$, $CH_2CN$, $CH_2CH=CH_2$, $CH_2C\equiv CH$, $CH_2CO_2(C_1-C_{12})$alkyl, $CH_2OCH_3$, $CH_2$-1,2,4-triazole;

$R_{11}$ is selected from H, CN, $(C_1-C_6)$alkyl, halo$(C_1-C_{12})$alkyl, halo$(C_1-C_6)$alkyl and $CO_2(C_1-C_{12})$alkyl;

$R_{12}$ is selected from H, $(C_1-C_8)$alkyl, $CO_2R_6$, CON$((C_1-C_8)$alkyl$)R_6$, $OR_6$, $SR_6$, $SO_2R_6$, $SO_2N((C_1-C_8)$alkyl$)R_{13}$; and $N((C_1-C_8)$alkyl$)R_{13}$;

$R_{13}$ is H, $(C_1-C_8)$alkyl, aryl or aryl$(C_1-C_6)$alkyl where the aryl group is naphthyl or phenyl;

A is N;

B is N;

Z is O, $CH(R_3)$, CO, CS, $CONR_{12}$ or $CSNR_{12}$;

X is selected from O, S, NH, $CO_2$, $OCH(R_6)CO_2$, SCH$(R_6)CO_2$, CH=C(Cl)$CO_2$, $CH_2CH(Cl)CO_2$, CONH, $OCH(R_6)$CONH, $SCH(R_6)$CONH, CH=C(Cl)CONH and $CH_2CH(Cl)$CONH when Z is $CH(R_3)$;

X is selected from CO, $OCH(R_6)$CO, $SCH(R_6)$CO, CH=C(Cl)CO and $CH_2CH(Cl)$CO when Z is O;

X is selected from O, S, CO, $OCH(R_6)$, CH=C(Cl), $CH_2CH(Cl)$, CONH, $OCH(R_6)$CONH, $SCH(R_6)$CONH, CH=C(Cl)CONH, $CH_2CH(Cl)$CONH and $NR_{12}$ when Z is CO, CS, $CONR_{12}$ or $CSNR_{12}$;

Q is $NR_7COR_8$, or selected from Q2, Q3, Q4, Q5, Q6, Q7, Q8, Q9, Q10, Q11, Q12, Q13, Q14, Q15 and Q16;

or the agronomically acceptable salts thereof selected from those formed from hydrochloric acid, sulfuric acid, acetic acid, propionic acid, phosphoric acid and oxalic acid.

4. The compound of claim 3 wherein $R_1$ is H, F or Cl;

$R_2$ is Cl;

$R_3$ is selected from H, bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, 3-furyl, 4-chloro-2-furyl, 5-chloro-2-furyl, 5-chloro3-furyl, 2,5-dichloro-3-furyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,6-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro.3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2, 6-dichloro-4-pyridyl, 2-thienyl, 3-thienyl, 4-chloro-2-thienyl, 5-chloro-2-thienyl, 5-chloro-3-thienyl and 2,5-dichloro-3-thienyl;

$R_4$ and $R_5$ are each independently selected from H, bromo, chloro, fluoro, CN, $(C_1-C_6)$alkyl, cyclo$(C_5-C_6)$alkyl, halo$(C_1-C_6)$alkyl, $(C_1-C_6)$alkoxy, $(C_1-C_6)$alkylthio, $CO_2R_6$, $CONHR_6$, $CON((C_1-C_6)alkyl)R_6$, $OR_6$, $SR_6$, $SO_2R_6$, $NHR_6$, 3-furyl, 4-chloro-2-furyl, 5-chloro-2-furyl, 5-chloro-3-furyl, 2,5-dichloro-3-furyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4pyridyl 2,6-dichloro-4-pyridyl, 2-thienyl, 3-thienyl, 4-chloro-2-thienyl, 5-chloro-2-thienyl, 5-chloro-3-thienyl and 2,5-dichloro-3thienyl;

$R_6$ is selected from H, $(C_1-C_6)$alkyl, 1-naphthyl, 2-naphthyl, phenyl, 4-methylphenyl, 4-methoxyphenyl, 4-nitrophenyl, 4-fluorophenyl, 4-chlorophenyl, 4trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-6-trifluoromethylphenyl and 3,4,6-trifluorophenyl;

$R_7$ is selected from H, $(C_1-C_6)$alkyl, cyclo$(C_5-C_6)$alkyl, halo$(C_1-C_6)$alkyl and $COR_9$;

$R_8$ is $(C_1-C_6)$alkyl, cyclo$(C_5-C_6)$alkyl, halo$(C_1-C_{12})$alkyl, 1-naphthyl, 2-naphthyl, phenyl, 4-methylphenyl, 4-methoxyphenyl, 4-nitrophenyl, 4-fluorophenyl, 4-chlorophenyl, 4-trifluoromethylphenyl, 4-bromophenyl, 4-chlorophenyl, 3-fluorophenyl, 4-trifluoromethoxyphenyl, 4-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5trifluoromethylphenyl and 3,4,5-trifluorophenyl;

$R_9$ is selected from H, $(C_1-C_6)$alkyl, $(C_2-C_6)$alkenyl, cyclo$(C_5C_6)$alkyl and halo$(C_1-C_6)$alkyl;

$R_{10}$ is selected from H, chloro, $NH_2$, $(C_1-C_6)$alkyl, halo$(C_1-C_6)$alkyl, CN, $CO_2(C_1-C_6)$alkyl, $CONH(C_1-C_6)$alkyl, $CON((C_1-C_6)alkyl)_2$, $CH_2CN$, $CH_2CH=CH_2$, $CH_2C\equiv CH$, $CH_2CO_2(C_1-C_6)$alkyl, $CH_2OCH_3$ and $CH_2$-1,2,4-triazole;

$R_{11}$ is H, CN, $(C_1-C_6)$alkyl, halo$(C_1-C_6)$alkyl and $CO_2(C_1-C_6)$alkyl;

$R_{12}$ is selected from H, $(C_1-C_8)$alkyl, $CO_2(C_1-C_6)$alkyl, $CON((C_1-C_6)alkyl)_2$, $O(C_1-C_6)$alkyl, $S(C_1-C_6)$alkyl, $SO_2(C_1-C_6)$alkyl, $SO_2N((C_1-C_6)alkyl)_2$ and $N(C_1-C_8)$alkyl)$_2$;

$R_{13}$ is H, $(C_1-C_6)$alkyl, aryl or aryl$(C_1-C_4)$alkyl where the aryl group is naphthyl or phenyl;

A is N;

B is N;

Z is O, $CH(R_3)$, CO, CS, $CONR_{12}$ or $CSNR_{12}$;

X is selected from O, S, NH, $CO_2$, $OCH(R_6)CO_2$, $SCH(R_6)CO_2$, $CH=C(Cl)CO_2$, $CH_2CH(Cl)CO_2$, CONH, $OCH(R_6)CONH$, $SCH(R_6)CONH$, $CH=C(Cl)CONH$ and $CH_3CH(Cl)CONH$ when Z is $CH(R_3)$;

X is selected from CO, $OCH(R_6)CO$, $SCH(R_6)CO$, $CH=C(Cl)CO$ and $CH_2CH(Cl)CO$ when Z is O;

X is selected from O, S, CO, $OCH(R_6)$, $CH=C(Cl)$, $CH_2CH(Cl)$, CONH $OCH(R_6)CONH$, $SCH(R_6)CONH$, $CH=C(Cl)CONH$, $CH_2CH(Cl)CONH$ and $NR_{12}$ when Z is CO, CS, $CONR_{12}$ or $CSNR_{12}$;

Q is selected from Q2, Q3, Q4, Q5, Q6, Q7, Q8, Q9, Q10, Q11, Q12, Q13, Q14, Q15 and Q16;

or the agronomically acceptable salts thereof selected from those formed from hydrochloric acid, acetic acid, phosphoric acid and oxalic acid.

5. A herbicidal composition comprising a compound as in claim 1, 2, 3 or 4 and an agronomically acceptable carrier.

6. The composition of claim 5 which contains from about 0.1% to 99% by weight of said compound.

7. The composition of claim 6 further comprising a second pesticide or a fertilizer.

8. A method of controlling a weed comprising applying a herbicidally effective amount of a composition of claim 5 and an agronomically acceptable carrier to the weed, to the locus of the weed or to the growth medium of said weed.

* * * * *